(12) United States Patent
Metz, Jr. et al.

(10) Patent No.: US 7,923,466 B2
(45) Date of Patent: Apr. 12, 2011

(54) 3-SUBSTITUTED-5- AND 6-AMINOALKYL INDOLE-2-CARBOXYLIC ACID AMIDES AND RELATED ANALOGS AS INHIBITORS OF CASEIN KINASE I

(75) Inventors: William Arthur Metz, Jr., Bridgewater, NJ (US); Fa-Xiang Ding, Staten Island, NY (US)

(73) Assignee: Aventis Pharmaceuticals Inc., Bridgewater, NJ (US)

( * ) Notice: Subject to any disclaimer, the term of this patent is extended or adjusted under 35 U.S.C. 154(b) by 171 days.

(21) Appl. No.: 12/269,216

(22) Filed: Nov. 12, 2008

(65) Prior Publication Data

US 2009/0082340 A1    Mar. 26, 2009

Related U.S. Application Data

(60) Division of application No. 11/674,385, filed on Feb. 13, 2007, now Pat. No. 7,629,376, which is a continuation of application No. PCT/US2005/029053, filed on Aug. 16, 2005.

(60) Provisional application No. 60/603,380, filed on Aug. 19, 2004.

(51) Int. Cl.
*A61K 31/404* (2006.01)
(52) U.S. Cl. ........................ 514/421; 514/414
(58) Field of Classification Search .................. 514/414, 514/421
See application file for complete search history.

(56) References Cited

FOREIGN PATENT DOCUMENTS

| WO | WO 94/14851 | 2/1994 |
| WO | WO 2004/014851 | 2/2004 |
| WO | WO 2005/061498 | 7/2005 |

OTHER PUBLICATIONS

Takano et al. Neuropsychopharmacology 2004, 29, 1901-09.*
Veenstra-VanderWeele et al. Neuropsychopharmacology 2006, 31, 1056-63.*
Schafer et al. (Drug Discovery Today 2008, 13 (21/22), 913-916).*
Horig et al. Journal of Translational Medicine 2004, 2(44).*
Ning, K., et. al., Circadian Regulation of GABAA Receptor Function by CKI-Epsilon-CKI-delta in the rat Suprachiasmatic Nuclei, Nature Neuroscience, Nature America, vol. 7, No. 5, (2004).

* cited by examiner

*Primary Examiner* — Joseph McKane
*Assistant Examiner* — Jason M Nolan
(74) *Attorney, Agent, or Firm* — Kelly L. Bender

(57) ABSTRACT

Methods for the treatment of a patient suffering from a disease or disorder ameliorated by inhibition of casein kinase Iε activity comprising the administration of a compounds of formula (I) and formula (II)

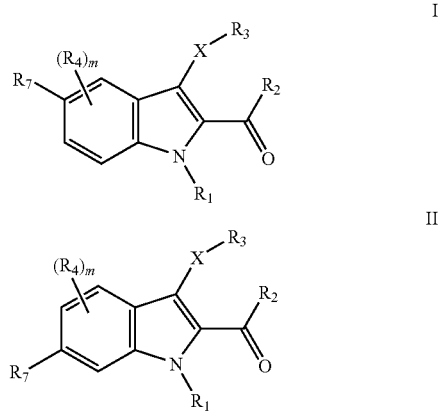

as inhibitors of human casein kinase Iε, and methods of using the compounds of formula (I) and formula (II) for treating central nervous system diseases and disorders including mood disorders and sleep disorders. The R-group substituents are defined herein and pharmaceutical compositions comprising compounds of formula (I) or formula (II) useful in the claimed methods of treatment are also disclosed.

18 Claims, No Drawings

SEQUENCE LISTING

```
<160> NUMBER OF SEQ ID NOS: 1

<210> SEQ ID NO 1
<211> LENGTH: 18
<212> TYPE: PRT
<213> ORGANISM: Artificial
<220> FEATURE:
<223> OTHER INFORMATION: Casein Kinase I substrate
<220> FEATURE:
<221> NAME/KEY: MISC_FEATURE
<222> LOCATION: (1)..(1)
<223> OTHER INFORMATION: Biotinylated

<400> SEQUENCE: 1

Arg Arg Lys Asp Leu His Asp Asp Glu Glu Asp Glu Ala Met Ser Ile
1               5                   10                  15

Thr Ala
```

3-SUBSTITUTED-5- AND 6-AMINOALKYL INDOLE-2-CARBOXYLIC ACID AMIDES AND RELATED ANALOGS AS INHIBITORS OF CASEIN KINASE I

CROSS-REFERENCE TO RELATED APPLICATIONS

This application is a divisional application of U.S. Ser. No. 11/674,385 filed on Feb. 13, 2007 which is a continuation of International Patent Application No. PCT/US2005/029053 filed on Aug. 16, 2005 which is incorporated herein by reference in its entirety which also claims the benefit of priority of U.S. Provisional Appln. Ser. No. 60/603,380 filed on Aug. 19, 2004.

FIELD OF THE INVENTION

This invention relates generally to pharmaceutical agents useful in the treatment and/or prevention of diseases and disorders associated with the central nervous system. More particularly, the present invention comprises compounds for the treatment of a patient suffering from a disease or disorder ameliorated by inhibition of casein kinase Iε activity through the administration of a series of substituted 5-aminoalkyl-1H-indole-2-carboxylic acid amides and 6-aminoalkyl-1H-indole-2-carboxylic acid amides. More specifically the invention relates to 3-arylthio-substituted and 3-heterocyclethio-substituted 5-aminoalkyl-1H-indole-2-carboxylic acid amides and 6-aminoalkyl-1H-indole-2-carboxylic acid amides, and related analogs which are inhibitors of human casein kinase Iε phosphorylation of the human clock protein Period (hPER).

BACKGROUND OF THE INVENTION

Rhythmic variations in behavior are displayed by many organisms, ranging from single cells to man. When the rhythm persists under constant conditions, and has a period of about one day, depending little on temperature, the rhythm is called "circadian" (Konopka, R. J. and Benzer, S. (1971) Proc. Nat. Acad. Sci. USA 68, 2112-2116).

Circadian rhythms are generated by endogenous biological pacemakers (circadian clocks) and are present in most living organisms including humans, fungi, insects and bacteria (Dunlap, J. C. (1999) Cell 96, 271-290; Hastings, J. W. et al. Circadian Rhythms, The Physiology of Biological Timing. In: Prosser, C. L. ed. Neural and Integrative Animal Physiology, New York: Wiley-Liss (1991) 435-546; Allada, R. et al. (1998) Cell 93, 791-804; Kondo et al. (1994) Science 266, 1233-1236; Crosthwaite, S. K. et al. (1997) Science 276, 763-769; Shearman, L. P. et al. (1997) Neuron, 19, 1261-1269). Circadian rhythms are self-sustaining and constant even under conditions of total darkness, but can be synchronized (entrained) to a new day/night regime by environmental signals such as light and temperature cycles (Pittendrigh, C. S. (1993) Annu. Rev. Physiol., 55, 16-54; Takahashi, J. S. (1995) Annu. Rev. Neurosci. 18, 531-553; Albrecht, U. et al. (1997) Cell, 91, 1055-1064). Circadian clocks are essential for maintaining biological rhythms and regulate a variety of circadian behaviors such as daily fluctuations in behavior, food intake and the sleep/wake cycle, as well as physiological changes such as hormone secretion and fluctuations in body temperature (Hastings, M. (1997) Trends Neurosci. 20, 459-464; Reppert, S. M. and Weaver, D. R. (1997) Cell 89, 487-490).

Genetic and molecular studies in the fruit fly *Drosophila melanogaster* led to elucidation of some of the genes involved in circadian rhythmicity. These studies led to recognition of a pathway that is closely auto-regulated and comprised of a transcription/translation-based negative feed back loop (Dunlap, J. C. (1999) Cell, 96, 271-290; Dunlap, J. C. (1996) Annu. Rev. Genet. 30, 579-601; Hall, J. C. (1996) Neuron, 17, 799-802). The core elements of the circadian oscillator in *Drosophila* consists of two stimulatory proteins dCLOCK/dBMAL (CYCLE) and two inhibitory proteins dPERIOD (dPER) and dTIMELESS (dTIM). dCLOCK and dBMAL heterodimerize forming the transcription factor dCLOCK/dBMAL that promotes expression of two genes termed *Drosophila* Period (dper) and *Drosophila* Timeless (dtim). Ultimately the mRNAs from these genes are transcribed to afford the proteins dPER and dTIM, respectively. For several hours the protein products dPER and dTIM are synthesized and phosphorylated in the cytoplasm, reach a critical level, and form heterodimers that are translocated into the nucleus. Once in the nucleus dPER and dTIM function as negative regulators of their own transcription, accumulation of dPER and dTIM declines, and activation of dper and dtim by dCLOCK/dBMAL starts again (Zylka, M. J. et al. (1998) Neuron 20, 1103-1110; Lowrey, P. L. et al. (2000) 288, 483-491). The dper gene has been shown to be a necessary element in controlling circadian rhythms in adult eclosion (the emergence of the adult fly from the pupa) behavior and locomotor activity (Konopka, R. J., & Benzer, S. (1971) Proc. Natl. Acad. Sci. USA, 68, 2112-2116). Mis-sense mutations of the per gene can either shorten (per$^S$) or lengthen (per$^L$) the period of circadian rhythms, while nonsense mutations (per$^O$) cause arrhythmicity in their behaviors (Hall, J. C. (1995) Trends Neurosci. 18, 230-240).

In mammals, the suprachiasmatic nuclei (SCN) of the anterior hypothalamus are the site of a master biological clock (for review see Panda et al, (2002) Nature 417, 329-335; Reppert, S. M. and Weaver, D. R. (1997) Cell, 89, 487-490). The SCN clock is entrained to the 24 hour day by the daily light-dark cycle, with light acting through both direct and indirect retina-to-SCN pathways (Klein, D. C. et al. (1991) Suprachiasmatic Nuclei: The Mind's Clock, Oxford University Press, New York). In the SCN of rodents, three Per genes have been identified and cloned, and are designated as mouse Per1 (mPer1), mPer2 and mPer3. The protein products of these mammalian genes (mPER1, mPER2, mPER3) share several regions of homology to each other, and each mammalian Per gene encodes a protein with a protein dimerization domain designated as PAS (PAS is an acronym for the first three proteins PER, ARNT and SIM found to share this functionally important dimerization domain) that is highly homologous to the PAS domain of insect PER. All Per messenger RNAs (mRNAs) and protein levels oscillate during the circadian day and are intimately involved in both positive and negative regulation of the biological clock, but only mPER1 and mPER2 oscillate in response to light (Zylka, M. J. et al. (1998) Neuron 20, 1103-1110.; Albrecht, U. et al., (1997) Cell 91, 1055-1064; Shearman, L. P. et al. (1997) Neuron 19, 1261-1269). The mammalian homolog of the *Drosophila* tim gene was cloned and designated as mTim. However, there was no evidence for mPER-mTIM interactions analogous to those observed in *Drosophila*, and it was suggested that PER-PER interactions may have replaced the function of PER-TIM dimers in the molecular workings of the mammalian circadian clock (Zylka, M. J. et al., (1998) Neuron 21, 1115-1122). Another possibility is that rhythms in PER1 and PER2 form negative feedback loops that regulate the transcriptional activity of the Clock protein (via their PAS domains), which, in turn, drives expression of either or both Per genes (Shearman, L. P. et al. (1997) Neuron 19, 1261-1269).

Understanding the roles of the three mPer genes in the mammalian clockwork has been the subject of much investigation. The structural homology of the mPER proteins to dPER led to the expectation that the mPER proteins would function as negative elements in the mammalian feedback loop. PER1 is believed to be involved in the negative regulation of its own transcription in the feedback loop, but recent evidence points to it being involved in the input pathway (Hastings, M. H. et al. (1999) Proc. Natl. Acad. Sci. USA 26, 15211-15216). PER2 is the most well characterized protein, and mPER2 mutant mice (mPer2$^{Brdm1}$), lacking 87 residues at the carboxyl portion of the PAS dimerization domain, have a shortened circadian cycle in normal light-dark settings, but show arrhythmicity in complete darkness. The mutation also diminishes the oscillating expression of both mPer1 and mPer2 in the SCN, indicating that mPer2 may regulate mPer1 in vivo (Zheng, B. et al. (1999) Nature 400, 169-173). PER2 has been shown to have a dual function in the regulation of the "gears" of the central clock (Shearman, L. P. et al. (2000) Science 288, 1013-1018). In that study, PER2 was shown to bind to cryptochrome (CRY) proteins and translocate to the nucleus where CRY negatively regulated transcription driven by the CLOCK and BMAL1 positive transcriptional complexes. Upon nuclear entry, PER2 initiated the positive arm of the clock by positively regulating BMAL1 transcription by a yet unidentified mechanism. The function of PER3 is poorly understood; however, in mPer3 knockout mice a subtle effect on circadian activity is observed, and therefore PER3 has been suggested to be involved in the circadian controlled output pathways (Shearman, L. P. et al. (2000) Mol. Cell. Biol. 17, 6269-6275). It has been reported that mPER proteins interact with each other and that mPER3 can serve as a carrier of mPER1 and mPER2 to bring them into the nucleus which is critical for the generation of circadian signals in the SCN (Kume, K. et al. (1999) Cell 98, 193-205; Takano, A. et al. (2000), FEBS Letters, 477, 106-112).

Phosphorylation of the components of the circadian clock has been postulated to regulate the duration of the cycle. The first genetic evidence that a specific protein kinase regulates the *Drosophila* circadian rhythm was the discovery of the novel gene doubletime (dbt), encoding a protein serine/threonine kinase (Price J. L. et al. (1998) Cell 94, 83-95; Kloss B. et al. (1998) Cell 94, 97-107). Missense mutations in the dbt result in an altered circadian rhythm. Null alleles of dbt result in hypophosphorylation of dPER and arrhythmia.

The mammalian kinases most closely related to DBT are casein kinase Iε (CK1ε) and casein kinase 1δ (CK1δ). Both kinases have been shown to bind to mPER1, and several studies have shown that CK1ε phosphorylates both mouse and human PER1 (Price J. L. et al. (1998) Cell 94, 83-95; Kloss B. et al. (1998) Cell 94, 97-107). In a study with human embryonic kidney 293T cells co-transfected with wild-type hCK1ε hPER1 showed a significant increase in phosphorylation (evidenced by a shift in molecular mass). In this study, the phosphorylated hPER1 had a half-life of approximately twelve hours whereas unphosphorylated hPER1 remained stable in the cell for more that 24 hours, suggesting phosphorylation of hPER1 leads to a decrease in protein stability (Kessler, G.A. et al. (2000) NeuroReport, 11, 951-955). Another study also showed the consequence of PER1 phosphorylation by hCK1ε includes both cytoplasmic retention and protein instability (Vielhaber, E. et al. (2000) Mol. Cell. Biol. 13, 4888-4899; Takano, A. et al. (2000) FEBS Letters 477, 106-112).

There has been no biochemical reason to choose between CK1ε or CK1δ as a potential regulator in mammals until Lowery et al. [(2000) Science 288, 483-491] found that in the Syrian Golden hamster, semidominant mutations in CK1ε (tau mutation, Ralph, M. R. and Menaker, M. (1988) Science 241, 1225-1227) caused a shortened circadian day in both heterozygous (22 h) and homozygous (20 h) animals. In this instance, reduced levels of CK1ε activity resulted in less PER phosphorylation with presumably higher levels of cytoplasmic PER protein leading to enhanced nuclear entry and altered circadian cycles. More recently, it has been suggested that CK1δ may also be involved in regulating circadian rhythmicity by post-translation modification of mammalian clock proteins hPER1 and hPER2 [Camacho, F. et al., (2001) FEBS Letters 489(2,3), 159-165]. Thus, inhibitors, including small molecule inhibitors, of mammalian or human CK1ε and/or CK1δ provide a novel means to phase shift or reset the circadian clock. As discussed below, the alteration of circadian rhythm may find utility for the treatment of sleep or mood disorders.

U.S. Pat. No. 6,555,328 B1 discloses screening methods in cells to identify compounds that alter circadian rhythms based on a test compound altering the ability of human casein kinase 1ε and/or human casein kinase 1δ to phosphorylate the human clock proteins hPER1, hPER2 and hPER3. For example, HEK293T cells are co-transfected with hCK1ε and Per1 or Per2. For the purpose of evaluating the relevancy of CK1ε inhibition and CK1ε inhibitors to circadian biology, a high-throughput cellular assay (33$^{rd}$ Annual Meeting, Soc. for Neurosci., Nov. 8-12, 2003, Abstract numbers 284.1, 284.2, and 284.3) was developed in which circadian rhythm could be monitored in a routine manner. The assay consists of Rat-1 fibroblasts stably expressing a Mper1-luc construct, thus enabling the determination of the rhythmic activation of the Mper1 promoter in living cells by repeatedly estimating luciferase activity by monitoring light-output over several days. The repeated measure format of the assay permits accurate and reproducible assessment of the concentration-dependent effects of CK1ε inhibitors on circadian rhythm and provides the nexus for relating CK1ε inhibition to circadian period alteration.

Sleep disorders have been classified into four major categories that include primary sleep disorders (dyssomnias and parasomnias), sleep disorders associated with medical/psychiatric disorders and a category of proposed sleep disorders for sleep disorders that cannot be classified due to insufficient data. Primary sleep disorders are thought to arise from abnormalities in the intrinsic systems responsible for sleep-wake generation (homeostatic system) or timing (circadian system). Dyssomnias are disorders in initiating or maintaining sleep and include primary insomnia, hypersomnia (excessive sleepiness), narcolepsy, breathing-related sleep disorder, circadian rhythm sleep disorder, and dyssomnias not otherwise specified. Primary insomnia is characterized by the persistence (>1 month) in difficulty of initiating and maintaining sleep or of non-restorative sleep. Difficulties in sleeping associated with primary insomnia leads to significant distress or impairment, including daytime irritability, loss of attention and concentration, fatigue and malaise, and deterioration of mood and motivation. Circadian rhythm sleep disorders include jet lag syndrome, shift work sleep disorder, advanced sleep phase syndrome and delayed sleep phase syndrome (J. Wagner, M. L. Wagner and W. A. Hening, Annals of Pharmacotherapy (1998)32, 680-691). Individuals in a forced sleep paradigm demonstrate a greater wakefulness, as a percentage of sleep time, at certain periods of circadian day (Dijk and Lockley, J. Appl. Physiol. (2002) 92, 852-862). It has been generally accepted that with age there is an advance in our circadian rhythm for sleep and often results in less quality sleep (Am J Physiol Endocrinol Metab. (2002) 282, E297-E303). Thus, sleep occurring out of circadian phase may suffer in qualitative and quantitative terms, as further exemplified by alterations in sleep with shift work and jet lag. Disturbance of the human circadian clock can cause sleep disorders and agents that modulate circadian rhythmicity, such as an inhibitor of CK1ε and/or CK1δ, may be useful for the treatment of sleep disorders, and particularly circadian rhythm sleep disorders.

Mood disorders are divided into depressive disorders ("unipolar depression"), bipolar disorders, and two disorders based on etiology that include mood disorder due to a general medical condition and substance-induced mood disorder. Depressive disorders are subclassified as major depressive disorder, dysthymic disorder and depressive disorder not otherwise specified. Bipolar disorders are subclassified as bipolar I disorder and bipolar II disorder. It has been observed that the specifier "seasonal pattern" can be applied to major depressive disorders that are recurrent and to the pattern of major depressive episodes in bipolar I disorder and bipolar II disorder. Prominent anergy, hypersomnia, overeating, weight gain, and a craving for carbohydrates often characterize major depressive episodes that occur in a seasonal pattern. It is unclear whether a seasonal pattern is more likely in major depressive disorder that is recurrent or in bipolar disorders. However, within the bipolar disorders, a seasonal pattern appears to be more likely in bipolar II disorder than in bipolar I disorder. In some individuals the onset of manic or hypomanic episodes may also be linked to a particular season. The winter-type seasonal pattern appears to vary with latitude, age and sex. Prevalence increases with higher latitudes, younger persons are at higher risk for winter depressive episodes, and females comprise 60% to 90% of persons with seasonal pattern. Seasonal affective disorder (SAD), a term commonly used in the literature, is a subtype of mood disorder that in the Diagnostic and Statistical Manual of Mental Disorders IV (DSM-IV) (American Psychiatric Association: "Diagnostic and Statistical Manual of Mental Disorders", Fourth Edition, Text Revision. Washington, D.C., American Psychiatric Association, 2000) is denoted by the term "with seasonal pattern" when describing a seasonal pattern of major depressive episodes in bipolar I disorder, bipolar II disorder or recurrent major depressive disorder (E. M. Tam et al., Can. J. Psychiatry (1995) 40, 457-466). The characteristics and diagnoses of depressive disorders, major depressive disorder, major depressive episode, bipolar I disorder, bipolar II disorder and seasonal effects are described in DSM-IV, Patients suffering from major depressive disorders, including SAD that is characterized by recurrent depressive episodes typically in winter, have been shown to be positively responsive to light therapy (Kripke, Journal of Affective Disorders (1998) 49(2), 109-117). The success of bright light treatment for patients with SAD and major depression resulted in the proposal of several hypotheses to explain the underlying mechanism of action for the therapeutic effect of light. These hypotheses included the "circadian rhythm hypothesis" that suggests the antidepressant effect of bright light could be associated with phase-shifting the circadian pacemaker relative to sleep (E. M. Tam et al., Can. J. Psychiatry (1995) 40, 457-466). In support of the link between light therapy and circadian rhythm, clinically effective light therapy in major depressive disorders causes a concomitant shift in circadian phase and the clinical effectiveness of light therapy appears to depend on the phase-shifting ability of the light therapy (Czeisler et al., The Journal of Physiology (2000) 526 (Part 3), 683-694; Terman et al., Arch. Gen. Psychiatry (2001) 58, 69-75). Additionally, light-therapy has been shown to accelerate and augment the effectiveness of the pharmacological treatment of major depressive disorders (Benedetti et al., J. Clin. Psychiatry (2003) 64, 648-653). Thus, inhibition of casein kinase Iε and/or casein kinase Iδ would be expected to cause a circadian phase shift and such inhibition represents a potential clinically effective mono- or combined therapy for mood disorders.

It should be noted that sleep disturbance is a criterion symptom for many psychiatric disorders (W. V. McCall, J. Clin. Psychiatry (2001) 62 (suppl 10), 27-32). Sleep disturbances are a common feature of depressive disorders and insomnia is the sleep disturbance that is frequently reported in depression, occurring in over 90% of depressed patients (M. E. Thase, J. Clin. Psychiatry (1999) 60 (suppl 17), 28-31). Accumulating evidence supports a common pathogenesis for primary insomnia and major depressive disorder. It has been hypothesized that corticotrophin releasing factor (CRF) hyperactivity (due to genetic predisposition or possibly early stress) and stress induce a process leading to exaggerated and protracted sleep disturbances, and eventually primary insomnia. Circadian rhythmicity in CRF secretion under non-stressed conditions may play a role in the normal sleep-wake expression (G. S. Richardson and T. Roth, J. Clin Psychiatry (2001) 62 (suppl 10), 39-45). Thus, agents that modulate circadian rhythmicity, for example by inhibition of casein kinase Iε and/or casein kinase Iδ, may be useful for treatment of depressive disorders due to effects on CRF secretion.

All of the references referred to hereinabove are incorporated herein by reference in their entirety.

Thus it is an object of this invention to provide a series of substituted 5-aminoalkyl-1H-indole-2-carboxylic acid amides and 6-aminoalkyl-1H-indole-2-carboxylic acid amides and related analogs that are inhibitors of casein kinase Iε. This object and other objects of this invention become apparent from the detailed discussion of the invention that follows.

SUMMARY OF THE INVENTION

The present invention provides substituted 5-aminoalkyl-1H-indole-2-carboxylic acid amides of formula I and substituted 6-aminoalkyl-1H-indole-2-carboxylic acid amides of formula II, and the stereoisomers, enantiomers, racemates and tautomers of said compounds and the pharmaceutically acceptable salts thereof, as inhibitors of human casein kinase Iε activity, and methods of using the compounds of formula I and formula II as pharmaceutical agents for the treatment of diseases and disorders of the central nervous system, such as for example mood disorders including major depressive disorder, bipolar I disorder and bipolar II disorder, and sleep disorders including circadian rhythm sleep disorders such as for example shift work sleep disorder, jet lag syndrome, advanced sleep phase syndrome and delayed sleep phase syndrome.

Accordingly, a broad embodiment of the invention is directed to a compound of formula I or formula II:

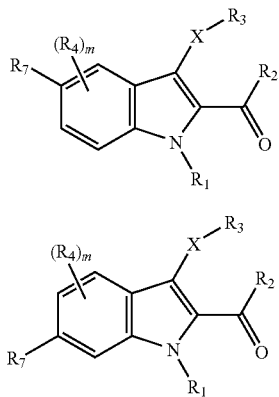

wherein

X is S or S(O)$_n$;

R$_1$ is H or C$_1$-C$_6$alkyl;

R$_2$ is NR$_5$R$_6$;

R$_3$ is aryl or heterocycle;

R$_4$ is C$_1$-C$_6$alkyl or halogen;

R$_5$ is H or C$_1$-C$_6$alkyl;

R$_6$ is H or C$_1$-C$_6$alkyl;

R$_7$ is CH$_2$NR$_8$R$_9$ wherein

R$_8$ is H, C$_1$-C$_{10}$alkyl, C$_3$-C$_8$cycloalkyl, aryl, aryl(C$_1$-C$_6$alkyl), aryl(C$_2$-C$_6$alkenyl), diaryl(C$_2$-C$_6$alkenyl), heterocycle, heterocycle(C$_1$-C$_6$alkyl), heterocycle(C$_2$-C$_6$alkenyl), hydroxy(C$_1$-C$_6$alkyl), dihydroxy(C$_2$-C$_6$alkyl), acyl, C$_1$-C$_6$alkoxycarbonyl, aryl(C$_1$-C$_6$alkoxy)carbonyl, carbamoyl(C$_1$-C$_6$alkyl), or P;

R$_9$ is H, C$_1$-C$_{10}$alkyl, heterocycle(C$_1$-C$_6$alkyl) or heterocycle(C$_2$-C$_6$alkenyl); or R$_8$ and R$_9$ together with the nitrogen to which they are attached form a heterocycle;

P is Gly, or L- or D-Ala, Val, Leu, Ile, Ser, Cys, Thr, Met, Pro, Phe, Tyr, Trp, His, Lys, Arg, Asp, Gly, Asn or Gln;

m is 0, 1 or 2;

n is 1 or 2; or a stereoisomer, an enantiomer, a racemate or a tautomer of said compound; or a pharmaceutically acceptable salt thereof.

A further embodiment of the present invention relates to a method for inhibiting casein kinase Iε activity in a patient comprising administering to said patient a therapeutically effective amount of an inhibitor of casein kinase Iε.

Another embodiment of the present invention relates to a method for inhibiting casein kinase Iε activity in a patient comprising administering to said patient a therapeutically effective amount of a compound of formula I or formula II.

Another embodiment of the present invention relates to a method for treating a patient suffering from a disease or disorder ameliorated by inhibition of casein kinase Iε comprising administering to said patient a therapeutically effective amount of a compound of formula I or formula II.

DETAILED DESCRIPTION OF THE INVENTION

As used herein, "stereoisomer" is a general term used for all isomers of individual molecules that differ only in the orientation of their atoms in space. The term stereoisomer includes mirror image isomers (enantiomers), mixtures of mirror image isomers (racemates, racemic mixtures), geometric (cis/trans or E/Z) isomers, and isomers of compounds with more than one chiral center that are not mirror images of one another (diastereoisomers). The compounds of the present invention may have asymmetric centers and occur as racemates, racemic mixtures, individual diastereoisomers, or enantiomers, or may exist as geometric isomers, with all isomeric forms of said compounds being included in the present invention.

As used herein, "R" and "S" are used as commonly used in organic chemistry to denote specific configuration of a chiral center. The term "R" (rectus) refers to that configuration of a chiral center with a clockwise relationship of group priorities (highest to second lowest) when viewed along the bond toward the lowest priority group. The term "S" (sinister) refers to that configuration of a chiral center with a counter-clockwise relationship of group priorities (highest to second lowest) when viewed along the bond toward the lowest priority group. The priority of groups is based upon sequence rules wherein prioritization is first based on atomic number (in order of decreasing atomic number). A listing and discussion of priorities is contained in "Stereochemistry of Organic Compounds", Ernest L. Eliel, Samuel H. Wilen and Lewis N. Mander, editors, Wiley-Interscience, John Wiley & Sons, Inc., New York, 1994.

In addition to the (R)-(S) system, the older D-L system may also be used herein to denote absolute configuration, especially with reference to amino acids. In this system a Fischer projection formula is oriented so that the number 1 carbon of the main chain is at the top. The prefix "D" is used to represent the absolute configuration of the isomer in which the functional (determining) group is on the right side of the carbon at the chiral center and "L", that of the isomer in which it is on the left.

As used herein, "tautomer" or "tautomerism" refers to the coexistence of two (or more) compounds that differ from each other only in the position of one (or more) mobile atoms and in electron distribution, for example, keto-enol tautomers or tautomerism.

As used herein, "alkyl" refers to a saturated linear or branched chain aliphatic hydrocarbon group having from one to ten carbon atoms wherein said alkyl is optionally substituted by one or more halogen atoms. Included within the meaning of "alkyl" are methyl, ethyl, propyl, isopropyl, butyl, sec-butyl, tert-butyl, trifluoromethyl, pentafluoroethyl, chloromethyl, chlorodifluoromethyl, bromomethyl and the like groups. Also included within the meaning of "alkyl", whether used alone or appearing in combination with another moiety such as for example aryl(C$_1$-C$_6$alkyl) or heterocycle(C$_1$-C$_6$alkyl), are "alkylene" or "alkylenyl" as are defined herein below.

As used herein "alkylene" or "alkylenyl" refers to a linear or branched, divalent, saturated aliphatic chain of one to six carbons and includes methylenyl, ethylenyl, propylenyl, isopropylenyl, butylenyl, isobutylenyl, t-butylenyl, pentylenyl, isopentylenyl, hexylenyl and the like groups.

As used herein "alkenyl" refers to a linear or branched monovalent unsaturated aliphatic chain having from two to six carbon atoms and includes ethenyl (also known as vinyl), 1-methylethenyl, 1-methyl-1-propenyl, 1-butenyl, 1-hexenyl, 2-methyl-2-propenyl, 2,4-hexadienyl, 1-propenyl, 2-propenyl, 2-butenyl, 2-pentenyl, and the like groups.

As used herein "alkynyl" is a linear or branched monovalent unsaturated aliphatic having from two to six carbon atoms with at least one triple bond and includes ethynyl, 1-propynyl, 1-butynyl, 1-hexynyl, 2-propynyl, 2-butynyl, 2-pentynyl and the like groups.

As used herein, "alkoxy" or "alkyloxy" refers to a monovalent substituent which consists of a linear or branched alkyl chain having from one to six carbon atoms linked through an ether oxygen atom and having its free valence bond from the ether oxygen, and includes methoxy, ethoxy, propoxy, isopropoxy, butoxy, sec-butoxy, tert-butoxy and the like groups.

As used herein, "alkylthio" refers to a monovalent substituent which consists of a linear or branched alkyl chain having from one to six carbon atoms linked through a sulfur atom and having its free valence bond from the sulfur, and includes methylthio, ethylthio, propylthio, isopropylthio, butylthio, sec-butylthio, tert-butylthio and the like groups.

As used herein "alkenyloxy" refers to a linear or branched monovalent unsaturated aliphatic chain having from two to six carbon atoms linked through an ether oxygen atom and having its free valence bond from the ether oxygen, and includes ethenyloxy (also known as vinyloxy), 1-methylethenyloxy, 1-methyl-1-propenyloxy, 1-butenyloxy, 1-hexenyloxy, 2-methyl-2-propenyl, 2,4-hexadienyloxy, 1-propenyloxy, 2-propenyloxy, 2-butenyloxy, 2-pentenyloxy, and the like groups.

As used herein "alkynyloxy" refers to a linear or branched monovalent unsaturated aliphatic chain having from two to six carbon atoms with at least one triple bond linked through an ether oxygen atom and having its free valence bond from the ether oxygen, and includes ethynyloxy, 1-propynyloxy, 1-butynyloxy, 1-hexynyloxy, 2-propynyloxy, 2-butynyloxy, 2-pentynyloxy and the like groups.

As used herein the term "$C_3$-$C_8$cycloalkyl" refers to a saturated monocyclic or bicyclic hydrocarbon ring structure containing from three to eight carbon atoms and includes cyclopropyl, cyclobutyl, cyclopentyl, cyclohexyl, cycloheptyl, norbornyl and the like groups.

As used herein the term "hydroxyalkyl" refers to a linear or branched monovalent saturated aliphatic chain having from 1 to 6 carbon atoms wherein one of said carbon atoms is substituted by a hydroxyl group. Included within the meaning of hydroxyalkyl are hydroxymethyl, 1-hydroxyethyl, 2-hydroxyethyl, 1-hydroxypropyl, 2-hydroxypropyl and the like groups.

As used herein the term "dihydroxyalkyl" refers to a liner or branched monovalent saturated aliphatic chain having from 2 to 6 carbon atoms wherein two of said carbon atoms is each substituted by a hydroxyl group. Included within the meaning of dihydroxyalkyl are 1,2-dihydroxyethyl, 1,2-dihydroxypropyl, 1,3-dihydroxypropyl and the like groups.

As used herein the term "carbamoylalkyl" refers to a linear or branched monovalent saturated aliphatic chain having from 1 to 6 carbon atoms wherein one of said carbon atoms is substituted by an aminocarbonyl ($H_2NC(=O)$) group. Included within the meaning of carbamoylalkyl are 1-carbamoylethyl, 2-carbamoylpropyl and the like groups.

As used herein, "aryl" or "Ar" means any stable monocyclic, bicyclic or tricyclic carbon ring of up to seven members in each ring, wherein at least one ring is aromatic and unsubstituted or substituted with from one to three substituents independently selected from the group consisting of methylenedioxy, hydroxy, $C_1$-$C_6$alkoxy, halogen, $C_1$-$C_6$alkyl, $C_2$-$C_6$alkenyl, $C_2$-$C_6$alkynyl, trifluoromethyl, trifluoromethoxy, $NO_2$, $NH_2$, $NH(C_1$-$C_6$alkyl), $-N(C_1$-$C_6$alkyl)$_2$, NH-acyl, $N(C_1$-$C_6$alkyl)acyl, hydroxy($C_1$-$C_6$alkyl), dihydroxy($C_1$-$C_6$alkyl), CN, $C(=O)O(C_1$-$C_6$alkyl), phenyl, phenyl($C_1$-$C_6$alkyl), phenyl($C_1$-$C_6$alkenyl), phenoxy and phenyl ($C_1$-$C_6$alkoxy). Included within the meaning of "aryl" or "Ar" are phenyl, 2-chlorophenyl, 3-chlorophenyl, 4-chlorophenyl, 2-fluorophenyl, 3-fluorophenyl, 4-fluorophenyl, 2-bromophenyl, 3-bromophenyl, 4-bromophenyl, 2-trifluoromethylphenyl, 3-trifluoromethylphenyl, 4-trifluoromethylphenyl, 2-methoxyphenyl, 3-methoxyphenyl, 4-methoxyphenyl, 2-aminophenyl, 3-aminophenyl, 4-aminophenyl, 2-methylaminophenyl, 3-methylaminophenyl, 4-methylaminophenyl, 2-dimethylaminophenyl, 3-dimethylaminophenyl, 4-dimethylaminophenyl, 2-methylphenyl, 3-methylphenyl, 4-methylphenyl, 2-nitrophenyl, 3-nitrophenyl, 4-nitrophenyl, 2,4-dichlorophenyl, 2,3-dichlorophenyl, 3,5-dimethylphenyl, 2-trifluoromethoxyphenyl, 3-trifluoromethoxyphenyl, 4-trifluoromethoxyphenyl, naphthyl, tetrahydronaphthyl, 2-biphenyl, 3-biphenyl, 4-biphenyl, 2-phenoxyphenyl, 3-phenoxyphenyl, 4-phenoxyphenyl, 2-benzyloxyphenyl, 3-benzyloxyphenyl, 4-benzyloxyphenyl, 4-methoxycarbonylphenyl, 2-cyano-4,5-dimethoxyphenyl, 2-fluoro-3-trifluorophenyl, 3-fluoro-5-trifluorophenyl, 2-fluoro-6-trifluoromethylphenyl, 2,4-dimethoxyphenyl, 4-hydroxy-3-methoxyphenyl, 3,5-dichloro-2-hydroxyphenyl, 3-bromo-4,5-dimethoxyphenyl, 4-benzyloxy-3-methylphenyl, 3-benzyloxy-4-methylphenyl, 4-styrylphenyl, 9-anthryl, 10-chloro-9-anthryl and the like groups.

As used herein, the term "aryl($C_1$-$C_6$alkyl)" includes an aryl group as defined above linked by a linear or branched alkylene chain containing one to six carbon atoms and having its free valence bond from one of the alkylene chain carbons. Included within the meaning of aryl-($C_1$-$C_6$alkyl) are phenylmethyl (benzyl), phenylethyl, 4-fluorobenzyl, 4-chlorobenzyl, 4-bromobenzyl, 2-nitrobenzyl, 3-nitrobenzyl, 4-nitrobenzyl, 4-dimethylaminobenzyl, 2-methylbenzyl, 3-methylbenzyl, 4-methylbenzyl, 2-methoxybenzyl, 3-methoxybenzyl, 4-methoxybenzyl, 2-benzyloxybenzyl, 3-benzyloxybenzyl, 4-benzyloxybenzyl, 2-trifluoromethylbenzyl, 3-trifluoromethylbenzyl, 4-trifluorobenzyl, 3-fluoro-5-trifluoromethylbenzyl, 2-fluoro-3-trifluoromethylbenzyl, 2,4-dimethoxybenzyl, 3,5-dichloro-2-hydroxybenzyl, 3-bromo-4,5-dimethoxybenzyl, 4-benzyloxy-3-methylbenzyl, 3-benzyloxy-4-methyl, 4-phenylbenzy and the like groups.

As used herein, the term "aryl($C_2$-$C_6$alkenyl)" refers to an aryl group as defined above linked by a linear or branched monovalent unsaturated aliphatic chain having from two to six carbon atoms and having its free valence bond from one of the alkylene chain carbons. Included within the meaning of aryl($C_2$-$C_6$alkenyl) are 3-phenyl-propen-1-yl, 2-phenylethenyl, 3-(4-hydroxy-3-methoxyphenyl)-2-propen-1-yl, 4-phenyl-3-butenyl, 3-phenyl-3-butenyl and the like groups.

As used herein, the term "diaryl($C_2$-$C_6$alkenyl)" refers to a linear or branched monovalent unsaturated aliphatic chain having from two to six carbon atoms wherein said chain is substituted by two aryl groups, wherein aryl is as defined above, and said aryl groups may be simultaneously bonded to one of said aliphatic chain carbons atoms or said aryl groups may be independently bonded to any two of said two to six aliphatic chain carbon atoms, having its free valence bond from one of the alkylene chain carbons. Included within the meaning of diaryl($C_2$-$C_6$alkenyl) are 3,3-diphenyl-2-propen-1-yl and the like groups.

As used herein, the term "aryl($C_1$-$C_6$alkoxy)" refers to an aryl group, as defined above, linked by a linear or branched alkoxy moiety containing one to six carbon atoms, as defined above, and having its free valence bond from the ether oxygen. Included within the meaning of aryl($C_1$-$C_6$alkoxy) are phenylmethoxy (benzyloxy), phenylethoxy, and the like groups.

As used herein, the term "aryl($C_1$-$C_6$alkylamino)" refers to an aryl group as defined above linked by a linear or branched alkylene chain containing one to six carbon atoms to a nitrogen atom and having its free valence bond from the nitrogen wherein said nitrogen is optionally substituted by hydrogen or $C_1$-$C_6$alkyl. Included within the meaning of aryl($C_1$-

$C_6$alkylamino) are phenylmethylamino (benzylamino), phenylethylamino, N-methyl-N-benzylamino and the like groups.

As used herein, the term "aryl($C_1$-$C_6$alkylthio)" refers to an aryl group, as defined above, linked by a linear or branched alkylene chain containing one to six carbon atoms to a sulfur atom, and having its free valence bond from the sulfur atom. Included within the meaning of aryl($C_1$-$C_6$alkylthio) are phenylmethylthio (benzylthio), phenylethylthio, and the like groups.

As used herein, the term "acyl" refers to a H—(C=O)—, $C_1$-$C_6$alkyl-(C=O)—, aryl-(C=O)—, aryl($C_1$-$C_6$alkyl)-(C=O)—, heterocycle-(C=O)—, or heterocycle($C_1$-$C_6$alkyl)-(C=O)— group, wherein alkyl, aryl and heterocycle are as defined herein, and having its free valence bond from the carbonyl (C=O) moiety. Included within the meaning of acyl are acetyl, propionyl, butyryl, isobutyryl, trifluoroacetyl, trichloroacetyl, benzoyl and the like groups.

As used herein, the term "alkoxycarbonyl" refers to a monovalent substituent comprising a linear or branched alkyl chain having from one to six carbon atoms linked through an ether oxygen atom to a carbonyl moiety and having its free valence bond from the carbonyl moiety. Included within the meaning of alkoxycarbonyl are methoxycarbonyl, ethoxycarbonyl, propyloxycarbonyl, isopropyloxycarbonyl, butoxycarbonyl, sec-butoxycarbonyl, tert-butoxycarbonyl (t-Boc or Boc), and the like groups.

As used herein, the term "aryl($C_1$-$C_6$alkoxy)carbonyl" refers to a monovalent substituent comprising an aryl($C_1$-$C_6$alkoxy) group, as defined above, linked through its ether oxygen atom to a carbonyl moiety and having its free valence bond from the carbonyl moiety. Included within the meaning of aryl($C_1$-$C_6$alkoxy)carbonyl are phenylmethoxycarbonyl (also known as benzyloxycarbonyl or carbobenzyloxy or CBZ), phenylethoxycarbonyl, phenylpropoxycarbonyl and the like groups.

As used herein, "heterocycle" or "heterocyclic" means a stable 5- to 7-membered monocyclic or stable 8- to 11-membered bicyclic heterocyclic ring which is either saturated or unsaturated, and which consists of carbon atoms and from one to three heteroatoms selected from the group consisting of N, O and S, and wherein the nitrogen and sulfur heteroatoms may optionally be oxidized, and the nitrogen heteroatom may optionally be quaternized, and includes any bicyclic group in which any of the above-defined heterocyclic rings is fused to a benzene ring. The heterocyclic ring may be attached at any heteroatom or carbon atom which results in the creation of a stable structure. The heterocyclic ring may be unsubstituted or substituted with from one to three substituents independently selected from the group consisting of $C_1$-$C_6$alkoxy, hydroxy, halogen, $C_1$-$C_6$alkyl, $C_2$-$C_6$alkenyl, $C_2$-$C_6$alkynyl, trifluoromethyl, trifluoromethoxy, $NO_2$, $NH_2$, NH($C_1$-$C_6$alkyl), N($C_1$-$C_6$alkyl)$_2$, NH-acyl, —N($C_1$-$C_6$alkyl)acyl, C(=O)O($C_1$-$C_6$alkyl), C(=O)$NH_2$, C(=O)NH($C_1$-$C_6$alkyl), C(=O)N($C_1$-$C_6$alkyl)$_2$, hydroxy($C_1$-$C_6$alkyl), dihydroxy($C_2$-$C_6$alkyl), aryl, aryl($C_1$-$C_6$alkyl), aryl($C_2$-$C_6$alkenyl), aryl($C_1$-$C_6$alkoxy), arylsulfonyl and pyrimidin-2-yl. Included within the meaning of heterocycle or heterocyclic are piperidinyl, 4-hydroxymethyl-piperidinyl, 3-carbamoylpiperidinyl, 1,4-dioxa-8-azaspiro[4,5]decanyl, piperazinyl, 2-oxopiperazinyl, 4-fluorophenylpiperainyl, 1,4-diazepinyl or homopiperazinyl, 4-t-butoxycarbonyl-1,4-diazepinyl, 4-pyrimidin-2-ylpiperazinyl, 4-(3-phenylpropenyl)-piperazinyl, 2-oxopiperidinyl, 2-oxopyrrolidinyl, 2-oxoazepinyl, azepinyl, pyrrolyl, pyrrolidinyl, 2-hydroxymethyl-pyrrolidinyl, pyrazolyl, pyrazolidinyl, imidazolyl, imidazolinyl, imidazolidinyl, pyridyl, pyrazinyl, pyrimidinyl, pyridazinyl, oxazolyl, oxazolidinyl, isoxazolyl, isoxazolidinyl, morpholinyl, thiazolyl, thiazolidinyl, isothiazolyl, quinuclidinyl, isothiazolidinyl, indolyl, quinolinyl, isoquinolinyl, benzimidazolyl, thiadiazolyl, benzopyranyl, benzothiazolyl, benzoxazolyl, furyl, 2-nitrofuryl, tetrahydrofuryl, 2-(2-chlorophenyl)furyl, benzofuranyl, tetrahydropyranyl, thienyl, 2-nitrothienyl, benzothienyl, thiomorpholinyl, oxadiazolyl and 1-phenylsulfonylpyrrolyl and the like groups.

As used herein, the term "heterocycle($C_1$-$C_6$alkyl)" or "heterocyclic($C_1$-$C_6$alkyl)" refers to a heterocycle or heterocyclic ring as defined above linked by a linear or branched alkylene chain containing one to six carbon atoms to a carbon atom or to a heteroatom selected from the group consisting of O, N and S. Included within the meaning of heterocycle($C_1$-$C_6$alkyl) or heterocyclic($C_1$-$C_6$alkyl) are 2-furanmethyl, 2-thenyl (2-thiophenemethyl), 5-nitro-2-thenyl, 5-(2-chlorophenyl)-2-furanmethyl, 1-(phenylsulfonyl)-1H-pyrrole-2-methyl and the like groups.

As used herein, the term "heterocycle($C_2$-$C_6$alkenyl)" or "heterocyclic($C_2$-$C_6$alkenyl)" refers to a heterocycle or heterocyclic ring as defined above linked by a linear or branched monovalent unsaturated aliphatic chain having from two to six carbon atoms and includes 3-(2-furanyl)-2-propen-1-yl, 3-(3-furanyl)-2-propen-1-yl, 3-(2-thienyl)-2-propen-1-yl, 3-(3-thienyl)-2-propen-1-yl, 3-(4-pyridinyl)-2-propen-1-yl, 3-(3-pyridinyl)-2-propen-1-yl, and the like groups.

As used herein, the term "heterocycle($C_1$-$C_6$alkoxy)" or "heterocyclic($C_1$-$C_6$alkoxy)" includes a heterocycle or heterocyclic ring as defined above linked by a linear or branched alkylene chain containing one to six carbon atoms linked through an ether oxygen atom and having its free valence bond from the ether oxygen. Included within the meaning of heterocycle($C_1$-$C_6$alkoxy) or heterocyclic($C_1$-$C_6$alkoxy) are 2-thienylmethoxy, 3-thienylmethoxy, 2-furanmethoxy, 3-furanmethoxy, 4-pyridinylmethoxy, 3-pyridinylmethoxy, 2-pyridinylmethoxy and the like groups.

As used herein, the term "heterocycle($C_1$-$C_6$alkylamino)" or "heterocyclic($C_1$-$C_6$alkylamino)" refers to a heterocycle or heterocyclic ring as defined above linked by a linear or branched alkylene chain containing one to six carbon atoms linked to a nitrogen atom and having its free valence bond from said nitrogen atom and wherein said nitrogen atom is optionally substituted by hydrogen or $C_1$-$C_6$alkyl. Included within the meaning of heterocycle($C_1$-$C_6$alkylamino) or heterocyclic($C_1$-$C_6$alkylamino) are 2-thienylmethylamino, 3-thienylmethylamino, 2-furanmethylamino, 3-furanmethylamino, 4-pyridinylmethylamino, 3-pyridinylmethylamino, 2-pyridinylmethylamino and the like groups.

As used herein, the term "heterocycle($C_1$-$C_6$alkylthio)" or "heterocyclic($C_1$-$C_6$alkylthio)" refers to a heterocycle or heterocyclic ring as defined above linked by a linear or branched alkylene chain containing one to six carbon atoms linked to a sulfur atom and having its free valence bond from said sulfur atom. Included within the meaning of heterocycle($C_1$-$C_6$alkylthio) or heterocyclic($C_1$-$C_6$alkylthio) are 2-thienylmethylthio, 3-thienylmethylthio, 2-furanmethylthio, 3-furanmethylthio, 4-pyridinylmethylthio, 3-pyridinylmethylthio, 2-pyridinylmethylthio and the like groups.

As used herein, "halogen", "hal" or "halo" refers to a member of the family of fluorine, chlorine, bromine or iodine.

As used herein, "P" refers to an alpha-amino acid in either the L- or D-configuration or mixtures of the L- and D-configuration including the racemic mixture and having its free valence bond from the C-1 carbonyl carbon atom of the amino acid. Alpha-amino acids (and their accepted abbreviations) included within the definition of P are glycine (Gly), alanine (Ala), valine (Val), leucine (Leu), isoleucine (Ile), serine (Ser), cysteine (Cys), threonine (Thr), methionine (Met), proline (Pro), phenylalanine (Phe), tyrosine (Tyr), tryptophan (Trp), histidine (His), lysine (Lys), arginine (Arg), aspartic acid (Asp), glutamic acid (glu), asparagine (Asn) and glutamine (Gln).

When any variable (e.g., aryl, heterocycle, $R_1$, $R_2$, $R_3$, $R_4$, $R_5$, $R_6$, $R_7$, $R_8$, $R_9$, X) occurs more than one time in any constituent or in a compound of formula I or formula II of this invention, its definition on each occurrence is independent of its definition at every other occurrence unless indicated otherwise. Also, combinations of substituents and/or variables are permissible only if such combinations result in stable compounds.

As used herein, "treat", "treating" or "treatment" refers to:
(i) preventing a disease, disorder or condition from occurring in a patient that may be predisposed to the disease, disorder and/or condition, but has not yet been diagnosed as having it;
(ii) inhibiting a disease, disorder or condition, i.e., arresting its development; or
(iii) relieving a disease, disorder or condition, i.e., causing regression of the disease, disorder and/or condition.

As used herein, the term "patient" refers to a warm blooded animal such as a mammal which is afflicted with a particular disease, disorder or condition. It is explicitly understood that guinea pigs, dogs, cats, rats, mice, horses, cattle, sheep, and humans are examples of animals within the scope of the meaning of the term.

As used herein, "disease" refers to an illness, sickness or an interruption, cessation or disorder of body functions, systems or organs.

As used herein, "disorder" refers to a disturbance of function, structure or both resulting from a genetic or embryologic failure in development, or from exogenous factors such as poison, injury or disease.

As used herein, "condition" refers to a state of being, health or physical fitness.

As used herein, "prophylaxis" refers to the prevention of disease.

As used herein, the term "sleep disorder", "sleep disorders" or "sleep disturbance" means insomnia.

As used herein, the term "insomnia" means the inability to sleep in the absence of external impediments, such as noise, bright light, etc., during the period when sleep should normally occur and the inability to sleep may vary in degree from restlessness or disturbed slumber to a curtailment of the normal length of sleep or to absolute wakefulness. The term "insomnia" includes primary insomnia, insomnia related to a mental disorder, substance-induced insomnia and circadian rhythm insomnia that is insomnia due to a change in the normal sleep-wake schedule (shift changes, shift work sleep disorder, jet lag or jet lag syndrome, etc.).

As used herein the term "primary insomnia" means difficulty in initiating sleep, in maintaining sleep or having restorative sleep which is not caused by a mental disorder or due to physiological effects of taking or withdrawing from certain substances (substance-induced insomnia).

As used herein the term "circadian rhythm sleep disorder" includes jet lag or jet lag syndrome, shift work sleep disorder, advanced sleep phase syndrome and delayed sleep phase syndrome.

As used herein the term "effective inhibitory amount of a compound" or "effective casein kinase Iε inhibitory amount of a compound" means enough of a compound that becomes bioavailable through the appropriate route of administration to treat a patient afflicted with a disease, disorder or condition amenable to such treatment.

As used herein the term "a therapeutically effective amount" means an amount of a compound which is effective in treating the named disease, disorder or condition.

As used herein, the term "pharmaceutically acceptable salt" is intended to apply to any salt, whether previously known or future discovered, that is used by one skilled in the art that is a non-toxic organic or inorganic addition salt which is suitable for use as a pharmaceutical. Illustrative bases which form suitable salts include alkali metal or alkaline-earth metal hydroxides such as sodium, potassium, calcium or magnesium hydroxides; ammonia and aliphatic, cyclic or aromatic amines such as methylamine, dimethylamine, triethylamine, diethylamine, isopropyldiethylamine, pyridine and picoline. Illustrative acids which form suitable salts include inorganic acids such as, for example, hydrochloric, hydrobromic, sulfuric, phosphoric and like acids, and organic carboxylic acids such as, for example, acetic, propionic, glycolic, lactic, pyruvic, malonic, succinic, fumaric, malic, tartaric, citric, ascorbic, maleic, hydroxymaleic and dihydroxymaleic, benzoic, phenylacetic, 4-aminobenzoic, 4-hydroxybenzoic, anthranilic, cinnamic, salicylic, 4-aminosalicylic, 2-phenoxybenzoic, 2-acetoxybenzoic, mandelic and like acids, and organic sulfonic acids such as methanesulfonic, benzenesulfonic and p-toluenesulfonic acids.

As used herein, the phrase "lengthening of circadian rhythm period" refers to increasing the interval between seminal events in a process that occurs regularly with a frequency of approximately once every 24 hours.

As used herein, the phrase "shortening of circadian rhythm period" refers to decreasing the interval between seminal events in a process that occurs regularly with a frequency of approximately once every 24 hours.

As used herein, "pharmaceutical carrier" or "pharmaceutically acceptable carrier" refers to known pharmaceutical excipients useful in formulating therapeutically active compounds for administration, and which are substantially non-toxic and non-sensitizing under conditions of use. The exact proportion of these excipients is determined by the solubility and chemical properties of the active compound, the chosen route of administration as well as standard pharmaceutical practice. In practicing the methods of this invention, the active ingredient is preferably incorporated into a composition containing a pharmaceutical carrier, although the compounds are effective and can be administered, in and of themselves. That said, the proportion of active ingredient can vary from about 1% to about 90% by weight.

Further abbreviations that may appear in this application shall have the following meanings:
Me (methyl), Et (ethyl), Ph (phenyl), $Et_3N$ (triethylamine), p-TsOH (para-toluene sulfonic acid), TsCl (para-toluenesulfonyl chloride), hept (heptane), DMF (dimethylformamide), NMP (1-methyl-2-pyrrolidinone or N-methyl-2-pyrrolidinone), IPA (isopropanol or isopropyl alcohol), DBU (1,8-diazabicyclo[5.4.0]undec-7-ene), DBN (1,5-diazabicyclo[4.3.0]non-5-ene), rt or r.t. (room temperature or ambient temperature), min or min. (minutes), h (hour or hours), UV (ultraviolet), LCMS (liquid chromatography mass spectrometry), t-Boc or Boc (tert-butoxycarbonyl), Bn (benzyl), t-Bu (tertiary butyl), i-Pr (isopropyl), TFA (trifluoroacetic acid), HOAc (acetic acid), EtOAc (ethyl acetate), $Et_2O$ (diethylether), EtOH (ethanol), DIEA (diisopropylethylamine), EDC (1-(3-dimethylaminopropyl)-3-ethylcarbodiimide hydrochloride); HOBT (1-hydroxybenzotriazole), g (gram), mg (milligram), µg (microgram), ng (nanogram), mL (milliliter), μL (microliter), L (liter), HPLC (high-performance liquid chromatography), TLC, tlc or Tlc (thin layer chromatography), g/L (grams per liter), $SiO_2$ (silica gel), L/min (liters per minute), mL/min (milliliters per minute), mmol (millimole), M (molar), mM (millimolar), μM (micromolar), nM (nanomolar), μCi (microCurie), CPM (counts per minute), rpm (revolutions per minute), mm (millimeter), μm (micrometer), μ (micron), nm (nanometer), ppm (parts per million), psi (pounds per square inch), eq. or equiv. (equivalent), $R_T$ (retention time), ° C. (degrees Celsius), and K (Kelvin).

Accordingly, a broad embodiment of the invention is directed to a compound of formula I or formula II:

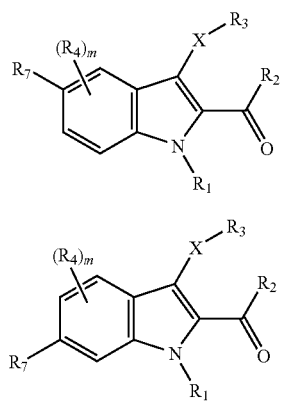

wherein X is S or $S(O)_n$; $R_1$ is H or $C_1$-$C_6$alkyl; $R_2$ is $NR_5R_6$; $R_3$ is aryl or heterocycle; $R_4$ is $C_1$-$C_6$alkyl or halogen; $R_5$ is H or $C_1$-$C_6$alkyl; $R_6$ is H or $C_1$-$C_6$alkyl; $R_7$ is $CH_2NR_8R_9$ wherein $R_8$ is H, $C_1$-$C_{10}$alkyl, $C_3$-$C_8$cycloalkyl, aryl, aryl($C_1$-$C_6$alkyl), aryl($C_2$-$C_6$alkenyl), diaryl($C_2$-$C_6$alkenyl), heterocycle, heterocycle($C_1$-$C_6$alkyl), heterocycle($C_2$-$C_6$alkenyl), hydroxy($C_1$-$C_6$alkyl), dihydroxy($C_2$-$C_6$alkyl), acyl, $C_1$-$C_6$alkoxycarbonyl, aryl($C_1$-$C_6$alkoxy)carbonyl, carbamoyl($C_1$-$C_6$alkyl), or P; $R_9$ is H, $C_1$-$C_{10}$alkyl, heterocycle($C_1$-$C_6$alkyl) or heterocycle($C_2$-$C_6$alkenyl); or $R_8$ and $R_9$ together with the nitrogen to which they are attached form a heterocycle; P is Gly, or L- or D-Ala, Val, Leu, Ile, Ser, Cys, Thr, Met, Pro, Phe, Tyr, Trp, His, Lys, Arg, Asp, Gly, Asn or Gln; m is 0, 1 or 2; and n is 1 or 2; or a stereoisomer, an enantiomer, a racemate or a tautomer of said compound; or a pharmaceutically acceptable salt thereof.

One embodiment of this invention relates to compounds of formula I or formula II wherein X is S.

Another embodiment of this invention relates to compounds of formula I or formula II wherein X is S and $R_2$ is $NH_2$.

A further embodiment of this invention relates to compounds of formula I or formula II wherein X is S, $R_2$ is $NH_2$, m is 0 and $R_7$ is $CH_2NR_8R_9$.

Another embodiment of this invention relates to compounds of formula I or formula II wherein X is S, $R_2$ is $NH_2$, m is 0, $R_7$ is $CH_2NR_8R_9$ and $R_1$ is $C_1$-$C_6$alkyl. The compound 1-methyl-5-methylaminomethyl-3-phenylsulfanyl-1H-indole-2-carboxylic acid amide is a representative example of a compound of formula I within the scope of this embodiment.

A further embodiment of this invention relates to compounds of formula I or formula II wherein X is S, $R_2$ is $NH_2$, m is 0, $R_7$ is $CH_2NR_8R_9$ and $R_1$ is H.

A further embodiment of this invention relates to compounds formula I wherein X is S, $R_1$ is H, $R_2$ is $NH_2$, m is 0, $R_7$ is $CH_2NR_8R_9$, $R_8$ is H, $C_1$-$C_{10}$alkyl, $C_3$-$C_8$cycloalkyl, hydroxy($C_1$-$C_6$alkyl), dihydroxy($C_2$-$C_6$alkyl) or $C_1$-$C_6$alkoxycarbonyl and $R_9$ is H. The following compounds are representative examples within the scope of this embodiment:

5-aminomethyl-3-phenylsulfanyl-1H-indole-2-carboxylic acid amide,
(2-carbamoyl-3-phenylsulfanyl-1H-indol-5-ylmethyl)-carbamic acid tert-butyl ester,
5-methylaminomethyl-3-phenylsulfanyl-1H-indole-2-carboxylic acid amide,
3-(3-chlorophenylsulfanyl)-5-methylaminomethyl-1H-indole-2-carboxylic acid amide,
3-(3-fluorophenylsulfanyl)-5-methylaminomethyl-1H-indole-2-carboxylic acid amide,
3-phenylsulfanyl-5-propylaminomethyl-1H-indole-2-carboxylic acid amide,
5-butylaminomethyl-3-phenylsulfanyl-1H-indole-2-carboxylic acid amide,
5-pentylaminomethyl-3-phenylsulfanyl-1H-indole-2-carboxylic acid amide,
5-heptylaminomethyl-3-phenylsulfanyl-1H-indole-2-carboxylic acid amide,
5-(bicyclo[2.2.1]hept-2-ylaminomethyl-3-phenylsulfanyl-1H-indole-2-carboxylic acid amide,
5-[(2-hydroxy-1-hydroxymethyl-1-methyl-ethylamino)methyl]-3-phenylsulfanyl-1H-indole-2-carboxylic acid amide,
5-[(2-hydroxy-1-methyl-ethylamino)methyl]-3-phenylsulfanyl-1H-indole-2-carboxylic acid amide,
5-[(2,3-dihydroxypropylamino)methyl]-3-phenylsulfanyl-1H-indole-2-carboxylic acid amide,
5-ethylaminomethyl-3-phenylsulfanyl-1H-indole-2-carboxylic acid amide,
3-phenylsulfanyl-5-propylaminomethyl-1H-indole-2-carboxylic acid amide, and
5-(isopropylaminomethyl)-3-phenylsulfanyl-1H-indole-2-carboxylic acid amide.

Another embodiment of this invention relates to compounds formula I wherein X is S, $R_1$ is H, $R_2$ is $NH_2$, m is 0, $R_7$ is $CH_2NR_8R_9$, $R_8$ is aryl, aryl($C_1$-$C_6$alkyl), heterocycle or carbamoyl($C_1$-$C_6$alkyl), and $R_9$ is H. The following compounds are representative examples within the scope of this embodiment:

5-(benzylaminomethyl)-3-phenylsulfanyl-1H-indole-2-carboxylic acid amide,
3-phenylsulfanyl-5-(quinolin-6-ylaminomethyl)-1H-indole-2-carboxylic acid amide,
5-[(2-cyano-4,5-dimethoxyphenylamino)methyl]-3-phenylsulfanyl-1H-indole-2-carboxylic acid amide,
3-phenylsulfanyl-5-[(3-trifluoromethyl-phenylamino)methyl]-1H-indole-2-carboxylic acid amide,
5-[(1-carbamoylethylamino)methyl]-3-phenylsulfanyl-1H-indole-2-carboxylic acid amide,
5-[(3-methoxyphenylamino)methyl]-3-phenylsulfanyl-1H-indole-2-carboxylic acid amide,
5-[(4-butylphenylamino)methyl]-3-phenylsulfanyl-1H-indole-2-carboxylic acid amide, and
5-[(2-fluorophenylamino)methyl]-3-phenylsulfanyl-1H-indole-2-carboxylic acid amide.

Another embodiment of this invention relates to compounds formula I wherein X is S, $R_1$ is H, $R_2$ is $NH_2$, m is 0, $R_7$ is $CH_2NR_8R_9$, and $R_8$ and $R_9$ together with the nitrogen to which they are attached form a heterocycle. The following compounds are representative examples within the scope of this embodiment:

5-(4-hydroxymethylpiperidin-1-ylmethyl)-3-phenylsulfanyl-1H-indole-2-carboxylic acid amide,
5-morpholin-4-ylmethyl-3-phenylsulfanyl-1H-indole-2-carboxylic acid amide,
3-phenylsulfanyl-5-piperidin-1 ylmethyl-1H-indole-2-carboxylic acid amide,
5-(3-carbamoylpiperidin-1-ylmethyl)-3-phenylsulfanyl-1H-indole-2-carboxylic acid amide,
3-phenylsulfanyl-5-(4-pyrimidin-2-yl-piperazin-1-ylmethyl)-1H-indole-2-carboxylic acid amide,
5-[4-(3-phenylpropenyl)piperazin-1-ylmethyl]-3-phenylsulfanyl-1H-indole-2-carboxylic acid amide,
4-(2-carbamoyl-3-phenylsulfanyl-1H-indol-5-ylmethyl)-[1,4]diazepane-1-carboxylic acid tert-butyl ester,
5-[1,4]diazepan-1-ylmethyl-3-phenylsulfanyl-1H-indole-2-carboxylic acid amide,
5-(2-hydroxymethyl-pyrrolidin-1-ylmethyl)-3-phenylsulfanyl-1H-indole-2-carboxylic acid amide,
5-(1,4-dioxa-8-aza-spiro[4,5]dec-8-ylmethyl)-3-phenylsulfanyl-1H-indole-2-carboxylic acid amide, and
5-[4-(4-fluorophenyl)piperazin-1-ylmethyl]-3-phenylsulfanyl-1H-indole-2-carboxylic acid amide.

Another embodiment of this invention relates to compounds formula II wherein X is S, $R_1$ is H, $R_2$ is $NH_2$, m is 0, $R_7$ is $CH_2NR_8R_9$, $R_8$ is H, $C_1$-$C_{10}$alkyl, aryl($C_1$-$C_6$alkyl), heterocycle($C_1$-$C_6$alkyl) or $C_1$-$C_6$alkoxycarbonyl and $R_9$ is H or heterocycle($C_1$-$C_6$alkyl). The following compounds are representative examples within the scope of this embodiment:
6-aminomethyl-3-phenylsulfanyl-1H-indole-2-carboxylic acid amide,
(2-carbamoyl-3-phenylsulfanyl-1H-indole-6-ylmethyl)-carbamic acid tert-butyl ester,
6-(benzylaminomethyl)-3-phenylsulfanyl-1H-indole-2-carboxylic acid amide,
6-[(4-nitrobenzylamino)methyl]-3-phenylsulfanyl-1H-indole-2-carboxylic acid amide,
6-[(4-dimethylaminobenzylamino)methyl]-3-phenylsulfanyl-1H-indole-2-carboxylic acid amide,
6-[(4-methylbenzylamino)methyl]-3-phenylsulfanyl-1H-indole-2-carboxylic acid amide,
6-[(4-methoxybenzylamino)methyl]-3-phenylsulfanyl-1H-indole-2-carboxylic acid amide,
6-[(4-bromobenzylamino)methyl]-3-phenylsulfanyl-1H-indole-2-carboxylic acid amide,
6-[(4-chlorobenzylamino)methyl]-3-phenylsulfanyl-1H-indole-2-carboxylic acid amide,
6-{[(biphenyl-4-ylmethyl)amino]methyl}-3-phenylsulfanyl-1H-indole-2-carboxylic acid amide,
6-[(3-nitrobenzylamino)methyl]-3-phenylsulfanyl-1H-indole-2-carboxylic acid amide,
6-[(2-nitrobenzylamino)methyl]-3-phenylsulfanyl-1H-indole-2-carboxylic acid amide,
3-phenylsulfanyl-6-[(4-trifluoromethylbenzylamino)methyl]-1H-indole-2-carboxylic acid amide,
6-[(3-fluoro-5-trifluoromethylbenzylamino)methyl]-3-phenylsulfanyl-1H-indole-2-carboxylic acid amide,
6-{[(2-methoxynaphthalen-1-ylmethyl)amino]-methyl]}-3-phenylsulfanyl-1H-indole-2-carboxylic acid amide,
6-[(2,4-dimethoxybenzylamino)methyl]-3-phenylsulfanyl-1H-indole-2-carboxylic acid amide,
6-[(3-phenoxybenzylamino)methyl]-3-phenylsulfanyl-1H-indole-2-carboxylic acid amide,
6-[(3-methoxybenzylamino)methyl]-3-phenylsulfanyl-1H-indole-2-carboxylic acid amide,
6-[(2-methylbenzylamino)methyl]-3-phenylsulfanyl-1H-indole-2-carboxylic acid amide,
6-[(3-methylbenzylamino)methyl]-3-phenylsulfanyl-1H-indole-2-carboxylic acid amide,
6-[(2-fluoro-3-trifluoromethylbenzylamino)methyl]-3-phenylsulfanyl-1H-indole-2-carboxylic acid amide,
6-[(2-methoxybenzylamino)methyl]-3-phenylsulfanyl-1H-indole-2-carboxylic acid amide,
6-{[(10-chloro-anthracene-9-ylmethyl)amino]methyl}-3-phenylsulfanyl-1H-indole-2-carboxylic acid amide,
6-[(3,5-dichloro-2-hydroxybenzylamino)methyl]-3-phenylsulfanyl-1H-indole-2-carboxylic acid amide,
6-[(3-bromo-4,5-dimethoxybenzylamino)methyl]-3-phenylsulfanyl-1H-indole-2-carboxylic acid amide,
6-[(4-benzyloxy-3-methoxybenzylamino)methyl]-3-phenylsulfanyl-1H-indole-2-carboxylic acid amide,
6-[(3-benzyloxy-4-methoxybenzylamino)methyl]-3-phenylsulfanyl-1H-indole-2-carboxylic acid amide,
6-{[(5-nitrothiophen-2-ylmethyl)amino]methyl}-3-phenylsulfanyl-1H-indole-2-carboxylic acid amide,
4-{[(2-carbamoyl-3-phenylsulfanyl-1H-indol-6-ylmethyl)amino]methyl}benzoic acid methyl ester,
3-phenylsulfanyl-6-[(4-styrylbenzylamino)methyl]-1H-indole-2-carboxylic acid amide,
6-[(2-fluoro-6-trifluoromethylbenzylamino)methyl]-3-phenylsulfanyl-1H-indole-2-carboxylic acid amide,
6-({[5-(2-chlorophenyl)-furan-2-ylmethyl]amino}methyl)-3-phenylsulfanyl-1H-indole-2-carboxylic acid amide,
6-{[(1-benzenesulfonyl-1H-pyrrol-2-ylmethyl)amino]methyl}-3-phenylsulfanyl-1H-indole-2-carboxylic acid amide,
6-{[bis-(5-nitrofuran-2-ylmethyl)amino]methyl}-3-phenylsulfanyl-1H-indole-2-carboxylic acid amide and
6-{[(5-nitrofuran-2-ylmethyl)amino]methyl}-3-phenylsulfanyl-1H-indole-2-carboxylic acid amide.

Another embodiment of this invention relates to compounds formula II wherein X is S, $R_1$ is H, $R_2$ is $NH_2$, m is 0, $R_7$ is $CH_2NR_8R_9$, $R_8$ is P and $R_9$ is H. The following compounds are representative examples within the scope of this embodiment:
6-[(2-aminopropionylamino)methyl]-3-phenylsulfanyl-1H-indole-2-carboxylic acid amide,
6-[(2-aminoacetylamino)methyl]-3-phenylsulfanyl-1H-indole-2-carboxylic acid amide,
6-[(2-amino-3-methylpentanoylamino)methyl]-3-phenylsulfanyl-1H-indole-2-carboxylic acid amide,
2-aminopentanedioic acid 5-amide 1-[(2-carbamoyl-3-phenylsulfanyl-1H-indol-6-ylmethyl)-amide],
6-{[(2-amino-3-(1H-indol-3-yl)propionylamino]methyl}-3-phenylsulfanyl-1H-indole-2-carboxylic acid amide,
6-[(2-amino-3-phenylpropionylamino)methyl]-3-phenylsulfanyl-1H-indole-2-carboxylic acid amide,
6-[(2-amino-4-methylsulfanylbutyrylamino)methyl]-3-phenylsulfanyl-1H-indole-2-carboxylic acid amide,
6-[(2,6-diaminohexanoylamino)methyl]-3-phenylsulfanyl-1H-indole-2-carboxylic acid amide and
3-amino-N-(2-carbamoyl-3-phenylsulfanyl-1H-indol-6-ylmethyl)succinamic acid.

A further embodiment of this invention relates to compounds formula II wherein X is S, $R_1$ is H, $R_2$ is $NH_2$, m is 0, $R_7$ is $CH_2NR_8R_9$, $R_8$ is aryl($C_2$-$C_6$alkenyl), diaryl($C_2$-$C_6$alkenyl) or heterocycle($C_2$-$C_6$alkenyl) and $R_9$ is H or heterocycle($C_2$-$C_6$alkenyl).

The following compounds are representative examples within the scope of this embodiment:

6-{[(bis-(3-furan-2-yl-allyl)amino]methyl}-3-phenylsulfanyl-1H-indole-2-carboxylic acid amide, 6-{[(3,3-diphenylallylamino)methyl]-3-phenylsulfanyl-1H-indole-2-carboxylic acid amide, and 6-{[3-(4-hydroxy-3-methoxyphenyl)allylamino]methyl}-3-phenylsulfanyl-1H-indole-2-carboxylic acid amide.

The compounds of the present invention can be prepared by processes analogous to those known in the art. Reaction schemes 1, 2, 3, 4 and 5, and the corresponding descriptive text, describe the preparation of the various compounds of the invention. The disclosed methods and examples are provided for illustration purposes and in no way limit the scope of the present invention. Alternative reagents, reaction conditions, and other combinations and permutations of the steps herein described to arrive at individual compounds are readily apparent to one of ordinary skill in the art. Tables 1 and 2 provide summaries of the specific compounds of this invention which are prepared in accordance with the synthetic procedures described herein, and biological data for the compounds of the invention are summarized in Table 3.

Chemical Synthesis

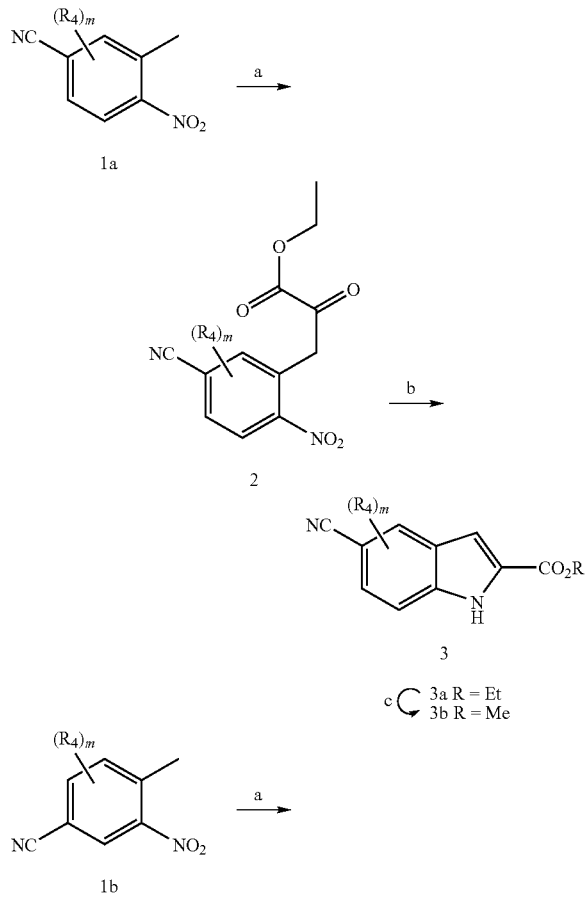

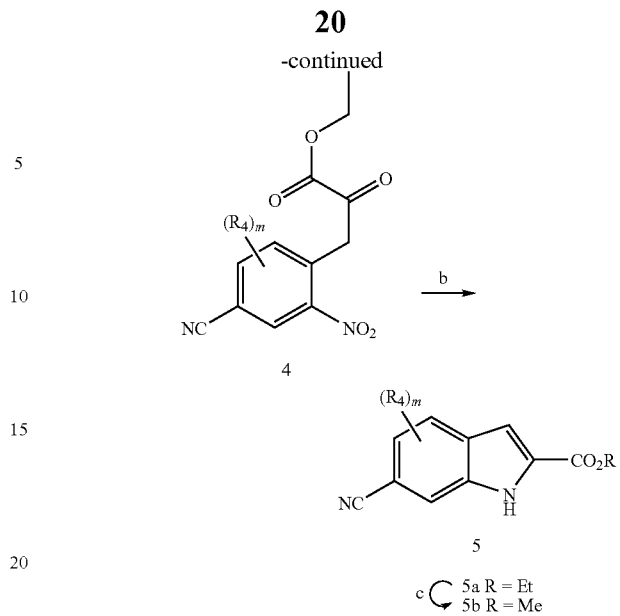

As described in scheme 1, optionally substituted ethyl 5-cyanoindole-2-carboxylate (3) and ethyl 6-cyanoindole-2-carboxylate (5) starting materials are prepared by methods well known to one skilled in the art from known or commercially available optionally substituted 3-methyl-4-nitrobenzonitrile (1a) or 4-methyl-3-nitrobenzonitrile (1b), respectively. As shown in scheme 1, step a, an oxalate diester, such as for example diethyloxalate, is added to a solution of a suitable base, such as for example sodium ethoxide in absolute ethanol, at from about 0° C. to about room temperature followed by addition of starting benzonitrile 1a or 1b at from about 0° C. to about room temperature. After stirring the mixture at about room temperature for about 8 to about 24 hours, the reaction is neutralized by addition of a suitable acid, such as for example hydrochloric acid, sulfuric acid or the like acids, the solvent is removed under reduced pressure and the residue is partitioned between water and a suitable organic solvent, such as for example methylene chloride, chloroform, ethyl acetate and the like solvents. The organic phase is dried, concentrated, and the residue is purified by chromatographic methods well known to one skilled in the art to provide oxopropionic ester 2 or 4, respectively. Oxopropionic esters 2 or 4 are each reduced with hydrogen in the presence of a suitable catalyst, such as for example palladium on carbon, in a suitable solvent, such as for example ethanol, until the theoretical amount of hydrogen is absorbed. The reaction mixture is filtered and the filtrate concentrated to afford the crude indole that is purified by chromatographic methods well known to one skilled in the art to afford optionally substituted ethyl 5-cyanoindole-2-carboxylate (3a) or ethyl 6-cyanoindole-2-carboxylate (5a), respectively. As shown in scheme 1, step c, optionally substituted ethyl 5-cyanoindole-2-carboxylate (3a) or ethyl 6-cyanoindole-2-carboxylate (5a) starting esters may be optionally transesterified to the corresponding methyl ester 3b or 5b, respectively, by methods well known to one skilled in the art, such as for example by stirring mixture of methanol, potassium carbonate and ethyl ester 3a or 5a at from about room temperature to the reflux temperature of the solvent, cooling, and isolating and purifying the product by methods well known to one skilled in the art, provides methyl ester 3b or 5b, respectively. Alternatively, methyl esters 3b and 5b are readily prepared by substituting dimethyloxalate for diethyloxalate and sodium methoxide in methanol for sodium ethoxide in absolute ethanol in the above described synthesis.

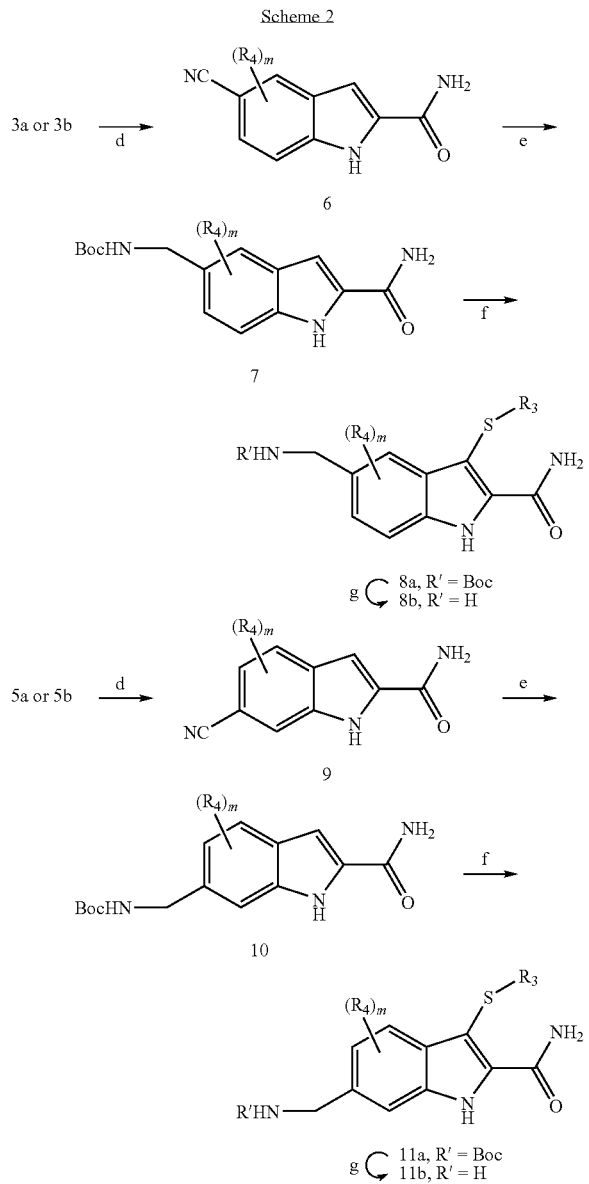

Scheme 2 describes the preparation of optionally substituted intermediate 3-arylthio- or 3-heterocyclethio-5-aminomethylindole-2-carboxamides 8b and 3-arylthio- or 3-heterocyclethio-6-aminomethylindole-2-carboxamides 11b. As shown in scheme 2, 5-cyano esters 3a/3b and 6-cyano esters 5a/5b are each converted to primary amides 6 and 9, respectively, by methods well known to one skilled in the art. Thus, treating a mixture of about 7M ammonia and ester 3a or 3b or ester 5a or 5b in a suitable polar solvent, such as for example methanol or ethanol, with a chip of lithium hydroxide and heating the resultant mixture in a pressure vessel at about 100° C. for about 16 hours provides, after chromatographic purification as is well known to one skilled in the art, primary amide 6 or 9, respectively. Alternatively, other reaction conditions well known to one skilled in the art may be employed, such as treating a solution of the appropriate ester in a suitable polar solvent, such as for example methanol or ethanol, with about 5M to about 7M ammonia solution for about one day to about three days at ambient temperature, or by heating the solution to about 55° C. for about 10 hours, provides primary amide 6 or 9, respectively, after isolation by methods well known to one skilled in the art. Alternatively, the appropriate ester may be suspended in a mixture of concentrated ammonium hydroxide solution and lithium chloride at ambient temperature for about three days to about five days until thin layer chromatographic analysis, or other suitable chromatographic analysis as is well known to one skilled in the art, indicates that the reaction is substantially complete. Primary amides 6 or 9 are isolated from the reaction mixture by methods well known to one skilled in the art.

Other methods to prepare the amides of the invention are readily appreciated by one skilled in the art. For example, carboxylic acids corresponding to scheme 1 compounds 3 or 5 wherein R is H may be prepared by hydrolysis of the corresponding esters 3a and 3b, or 5a and 5b, by methods well known to one skilled in the art. For example, a suitable base, such as for example potassium hydroxide, sodium hydroxide, lithium hydroxide and the like bases, is added to a mixture of ester 3a or 3b, or 5a or 5b, in a suitable solvent such as for example a mixture of tetrahydrofuran and water. The mixture is heated at about 90° C. to about 110° C. for about 0.5 hour to about 2 hours. The product is recovered as a salt by filtration and the filtrate is concentrated to provide additional material as a residue. The filter cake and residue are combined and acidified by methods well known to one skilled in the art, such as for example acidification with a suitable acid such as acetic acid in a suitable solvent such as methanol, ethanol and the like solvents, to provide the corresponding carboxylic acids of compound 3 or 5 respectively, wherein R is H. These carboxylic acids are readily converted to amides of the invention by procedures well known to one skilled in the art, such as for example, a solution of carboxylic acid 3 or 5 in a suitable solvent such as dimethylformamide can be treated with a base such as diisopropylethylamine, a carbodiimide such as for example 1-(3-dimethylaminopropyl)-3-ethylcarbodiimide hydrochloride, 1-hydroxybenzotriazole and ammonium chloride. When the reaction is complete as determined by thin layer chromatography, or other suitable chromatographic analyses as are well known to one skilled in the art, the mixture can be diluted with a suitable solvent, and the product can be isolated and chromatographically purified by methods well known to one skilled in the art to provide primary amides 6 or 9, respectively, wherein $R_2$ is $NH_2$. If primary or secondary $C_1$-$C_6$alkylamines are employed in place of ammonium chloride, one can also prepare the corresponding $C_1$-$C_6$alkyl secondary and tertiary amides corresponding to compounds 6 or 9 wherein $NH_2$ is replaced by $NH(C_1$-$C_6$alkyl) or $N(C_1$-$C_6$alkyl)$_2$, respectively.

As show in scheme 2, step e, the nitrile moiety of optionally substituted 5-cyanoindole-2-carboxamide 6 and 6-cyanoindole-2-carboxamide 9 are each reduced to the corresponding primary amine that is simultaneously Boc-protected to provide intermediate primary amides 7 and 10, respectively, by methods well known to one skilled in the art. For example, a solution of 5-cyanoindole-2-carboxamide 6 or 6-cyanoindole-2-carboxamide 9 in a suitable polar solvent, such as for example, methanol, is treated with nickel chloride and Boc-anhydride. The mixture is then treated at from about 0° C. to about 15° C. with a suitable reducing agent, such as for example sodium borohydride, and then stirred at about room temperature for about 8 hours to about 24 hours. The reaction mixture is concentrated, extracted and the product isolated by methods well known to one skilled in the art to provide the corresponding 5- or 6-Boc-protected-aminomethylindole-2-carboxamides 7 or 10, respectively.

As shown in scheme 2, step f, intermediate amides 7 and 10 are each converted to the corresponding 3-arylthio or 3-heterocyclethio compounds 8a and 11a, respectively, by methods well known to one skilled in the art. For example, a suspension of intermediate amide 7 or 10 in a suitable solvent, such as for example dimethylformamide or NMP, is treated with a suitable base, such as for example sodium hydride or lithium hydride, at ambient temperature, followed by treatment with a suitable diaryldisulfide or diheterocycledisulfide, and then the mixture is stirred at ambient temperature to about 100° C. for about 12 hours to about 20 hours. The course of the reaction is followed by thin layer chromatographic analysis or other chromatographic methods as are well known to one skilled in the art. When complete, the reaction is worked-up by extractive methods as are well known to one skilled in the art. The desired intermediate 5-Boc-protected-aminomethylindole-2-carboxamide 8a and 6-Boc-protected-aminomethylindole-2-carboxamide 11a are each isolated and chromatographically purified by methods as are well known to one skilled in the art to provide compounds 8a and 11a wherein $R_3$ is aryl or heterocycle. As shown in scheme 2, step g, acidic hydrolysis of the Boc-protecting group is performed in a manner well known to one skilled in the art, such as for example treating compound 8a or 11a with excess trifluoroacetic acid at about room temperature for about 5 minutes to about 30 minutes, concentrating the mixture and isolating the corresponding primary amine 8b or 11b, respectively, as the trifluoroacetate salt.

Alternatively, as shown in scheme 2, step f, a mixture of the diaryldisulfide or diheterocycledisulfide and about one equivalent of cesium carbonate in a suitable solvent, such as for example dimethylformamide or NMP, is treated with optionally substituted intermediate amide 7 or 10, and then the mixture is heated at about 80° C. to about 120° C. for about one to about six hours. The reaction is monitored by thin layer chromatography or other chromatographic methods as are well known to one skilled in the art. The desired optionally substituted intermediate 3-arylthio- or 3-heterocyclethio-5-Boc-protected-aminomethylindole-2-carboxamide 8a and 3-arylthio- or 3-heterocyclethio-6-Boc-protected-aminomethylindole-2-carboxamide 11a are each isolated and chromatographically purified by methods as are well to one skilled in the art to provide compounds 8a and 11a wherein $R_3$ is aryl or heterocycle. The Boc-protecting group of compounds 8a and 11a is removed by acid hydrolysis as described above to afford the corresponding primary amine 8b or 11b, respectively, as the trifluoroacetate salt.

Scheme 3

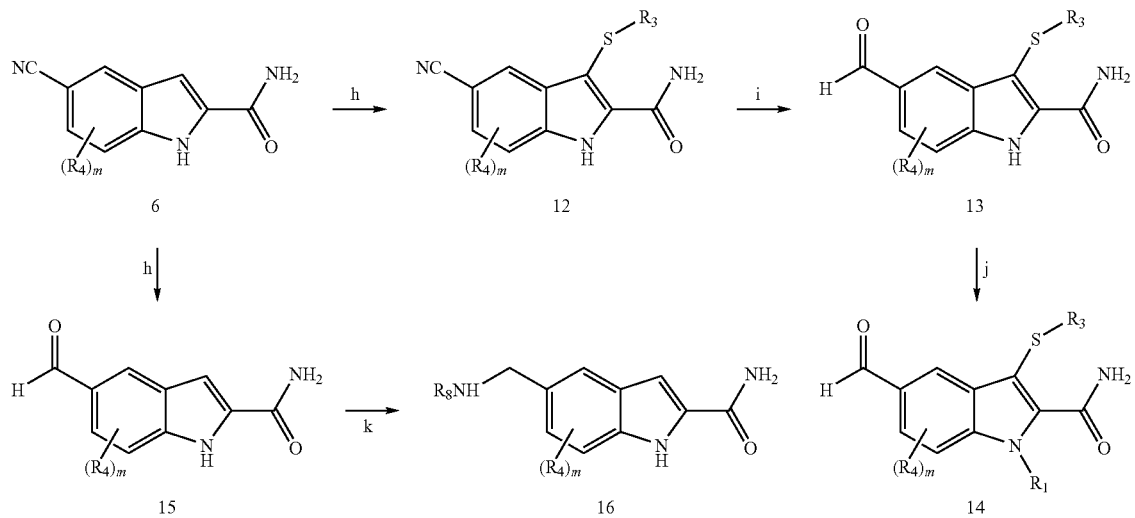

As described in scheme 3, optionally substituted intermediates 13, 14 and 15 are each prepared from optionally substituted 5-cyanoindole-2-carboxylic acid amide 6. As shown in scheme 3, step h, 5-cyanoindole-2-carboxylic acid amide 6 is converted to the corresponding 3-arylthio or 3-heterocyclethio compound 12 as is described above in scheme 2, step f, to provide 3-arylthio- or 3-heterocyclethio-5-cyanoindole-2-carboxylic acid amide 12 after isolation and purification by methods as are well known to one skilled in the art. As show in scheme 3, step i, the nitrile moiety of intermediate 12 is reduced by methods well known to one skilled in the art, such as for example, by treating a suspension of intermediate 12 and $NaH_2PO_2$ in pyridine and water with a slurry of Raney nickel, and heating at about 95° C. for about 4 hours to about 5 hours. The reaction mixture is filtered, and the filtrate is concentrated to a minimum volume and treated with ice water to afford, after isolation and drying by procedures that are well known to one skilled in the art, intermediate 5-formyl-3-substituted-indole-2-carboxylic acid amide 13.

As shown in scheme 3, step j, the indole nitrogen of optionally substituted 3-arylthio- or 3-heterocyclethio-5-formylindole-2-carboxamide 13 is N-alkylated to provide compound 14 wherein $R_1$ is $C_1$-$C_6$alkyl by methods well known to one skilled in the art. Thus, a solution of intermediate 13 in a suitable polar solvent, such as for example dimethylformamide or NMP, is treated at about ambient temperature with a suitable base, such as for example potassium hydroxide, sodium hydroxide or potassium t-butoxide, and then treated with a solution of a $C_1$-$C_6$-alkyl halide in a suitable polar solvent, such as for example dimethylformamide or NMP. The reaction is stirred for about 24 hours to about 72 hours at room temperature and diluted with a suitable solvent such as ethyl acetate. The organic phase is washed with brine, dried and concentrated to afford N-alkylated compound 14 wherein $R_1$ is $C_1$-$C_6$alkyl. One skilled in the art recognizes that other conditions for N-alkylation of the indole nitrogen may be employed, such as for example by treating a solution of the compound of formula 13 and a suitable solvent, such as for example 1,3-dimethyl-3,4,5,6-tetrahydro-2(1H)-pyrimidinone with a $C_1$-$C_6$-dialkylsulfate and a suitable base, such as for example cesium carbonate, at ambient temperature for a suitable period of time. Alternatively, the nitrogen of the indole ring may also be alkylated by treating a pyridine solution of a compound of formula 13 with a $C_1$-$C_6$-alkyl halide in the presence of a suitable base such as for example cesium carbonate with heating for a suitable period of time. Additionally, one skilled in the art recognizes that N-alkylation of the indole nitrogen may be performed at other points in the synthetic steps disclosed in schemes 1 to 4.

As also described in scheme 3, optionally substituted intermediate 6 is also reduced with Raney nickel, under step i conditions as described for the reduction of intermediate 12 to 13, to afford optionally substituted 5-formylindole-2-carboxylic acid amide 15. Aldehyde 15 is converted by reductive amination to optionally substituted 5-alkylaminomethylindole-2-carboxylic acid amides 16 by methods well known to one skilled in the art, such as for example by treating a solution of optionally substituted aldehyde 15 in a suitable solvent, such as a mixture of acetic acid and tetrahydrofuran, with an alkylamine followed by addition of a suitable base, such as for example potassium or sodium carbonate, and a suitable reducing agent, such as for example sodium cyanoborohydride at about room temperature. The reaction is monitored by chromatographic methods as are well known to one skilled in the art, such as thin layer chromatography, and when complete the reaction is diluted with a suitable solvent, washed with sodium bicarbonate or potassium bicarbonate and the dried organic phase is concentrated to afford optionally substituted 5-alkylaminomethylindole-2-carboxylic acid amide 16.

Scheme 4

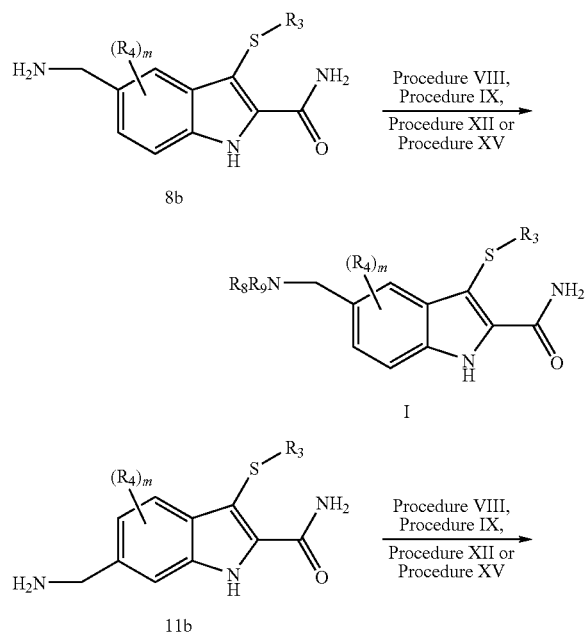

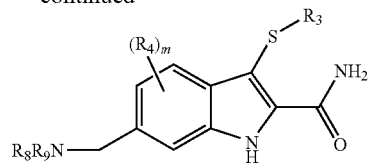

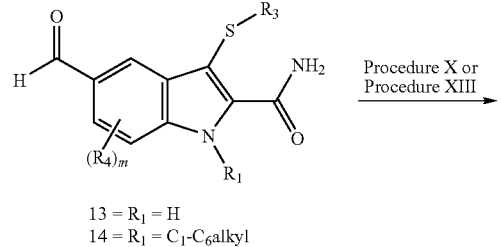

13 = $R_1$ = H
14 = $R_1$ = $C_1$-$C_6$alkyl

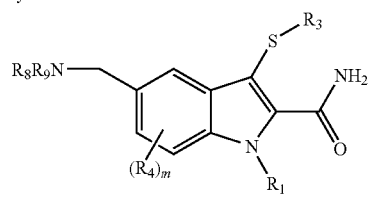

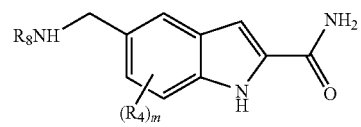

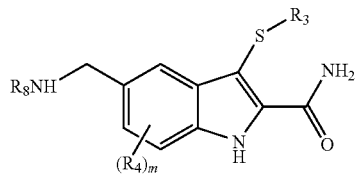

Scheme 4 describes methods for converting optionally substituted intermediates 8b, 11b, 13, 14 and 16 to compounds of formula I and II of the invention by methods well known to one skilled in the art. One skilled in the art readily appreciates that these methods are generally applicable to the preparation of compounds of formula I and II from precursor compounds that are not specifically shown in scheme 4, and that the methods shown are for illustrative purposes and do not limit the scope of the invention. Primary amines 8b and 11b are considered as compounds of formula I and II, respectively, of the invention.

As shown in scheme 4, procedure VIII, a mixture of primary amine 8b or 11b as a salt, such as for example the trifluoroacetate salt from cleavage of the Boc-protecting group of precursor compounds 8a or 11a, respectively, a suitable base such as potassium carbonate or sodium carbonate and a polar solvent such as dimethylformamide is treated with an alkyl halide at about room temperature. The reaction is monitored by chromatographic methods well known to one skilled in the art, such as for example thin layer chromatography, and when complete the mixture is diluted with a suitable solvent such as for example ethyl acetate, and the organic phase is washed with brine, dried and concentrated to afford the alkylaminomethylindole of formula I or II, respectively.

As shown in scheme 4, procedure IX, a solution of optionally substituted primary amine 8b or 11b as a salt, such as for example a trifluoroacetate salt obtained from hydrolysis of the Boc-protecting group of intermediate 8a or 11a, respectively, in a suitable solvent such as for example acetic acid and tetrahydrofuran is neutralized with potassium carbonate, the mixture is treated with the desired aldehyde and stirred at room temperature for about 10 minutes. The mixture is then added to a suitable reducing agent, such as for example MP-CNBH$_3$ resin, at about room temperature and agitated. The reaction is monitored by chromatographic methods as are well known to one skilled in the art, such as for example thin layer chromatography. When the reaction is complete, the mixture is separated from the resin and the resin is washed with a suitable solvent, such as for example tetrahydrofuran. The combined reaction filtrate and washings are concentrated to afford the desired N-substituted-aminomethylindole of formula I or II, respectively.

As shown in scheme 4, procedure XII, a solution of optionally substituted primary amine 8b or 11b as a salt, such as for example a trifluoroacetate salt obtained from hydrolysis of the Boc-protecting group of intermediate 8a or 11a, respectively, in a suitable solvent such as for example acetic acid and tetrahydrofuran, is neutralized with potassium carbonate followed by addition of the desired aldehyde and sodium cyanoborohydride at about room temperature. The reaction is monitored by chromatographic methods as are well known to one skilled in the art, such as for example thin layer chromatography. When the reaction is complete, ethyl acetate is added and the organic phase is washed with brine, dried and concentrated to afford the desired N-substituted-aminomethylindole of formula I or II, respectively.

As shown in scheme 4, procedure XV, a solution of optionally substituted primary amine 8b or 11b in a suitable solvent such as for example dimethylformamide or NMP is treated with an aqueous solution of a suitable base, such as for example potassium carbonate, sodium carbonate or the like bases, and then treated with an N-Boc-protected alpha amino acid N-hydroxysuccinimide ester at about room temperature. The reaction is monitored by chromatographic methods as are well known to one skilled in the art, such as for example thin layer chromatography. When the reaction is complete, ethyl acetate is added and the organic phase is washed with bicarbonate solution and brine, dried and concentrated to afford the aminomethylindole of formula I or II, respectively, wherein R$_8$ is an N-Boc-protected alpha amino acid moiety and R$_9$ is hydrogen. The Boc-protecting group is removed by treatment with trifluoroacetic acid for about 5 to about 15 minutes and then ether is added to precipitate the trifluoroacetate salt of the desired amino acid amide derivative of formula I or II, respectively.

As shown in scheme 4, procedure X, a solution of optionally substituted 3-arylthio- or 3-heterocyclethio-5-formyl-indole-2-carboxylic acid amide 13 or 14 in a suitable solvent such as for example acetic acid and tetrahydrofuran is treated with a primary amine at about room temperature. After about 40 minutes the reaction solution is added to a suitable reducing agent such as for example MP-CNBH$_3$ resin, at about room temperature. The reaction is monitored by chromatographic methods as are well known to one skilled in the art, such as for example thin layer chromatography. When the reaction is complete, the mixture is separated from the resin and the resin is washed with a suitable solvent, such as for example tetrahydrofuran. The combined reaction filtrate and washings are concentrated to afford the desired 3-arylthio- or 3-heterocyclethio-5-N-substituted-aminomethylindole-indole-2-carboxylic acid of formula I.

As shown in scheme 4, procedure XIII, a solution of optionally substituted 3-arylthio- or 3-heterocyclethio-5-formylindole-2-carboxylic acid amide 13 or 14 in a suitable solvent such as for example acetic acid and tetrahydrofuran is treated a suitable base, such as for example triethylamine, a suitable primary or secondary amine and then sodium cyanoborohydride at about room temperature. The reaction is monitored by chromatographic methods well known to one skilled in the art, such as for example thin layer chromatography. When the reaction is complete, ethyl acetate is added and the organic phase is washed with sodium bicarbonate solution, dried and concentrated to afford the desired 5-N-substituted-aminomethylindole of formula I As shown in scheme 4, procedure Ia, optionally substituted 5-N-substituted-aminomethylndole-2-carboxylic acid amide 16 is treated with a diaryldisulfide or a diheterocycledisulfide, as described above in scheme 2, step f using sodium hydride, for the preparation of compounds 8a and 11a from amides 7 or 10, respectively, to provide 3-arylthio- or 3-heterocyclethio-5-substituted-aminomethylindole-2-carboxamide of formula I.

As shown in scheme 4, procedure Ib, optionally substituted 5-N-substituted-aminomethylndole-2-carboxylic acid amide 16 is treated with a diaryldisulfide or a diheterocycledisulfide, as described above in scheme 2, step f using cesium carbonate, for the preparation of compounds 8a and 11a from 7 or 10, respectively, to provide 3-arylthio- or 3-heterocyclethio-5-N-substituted-aminomethylindole-2-carboxamide of formula I.

Additionally compounds of formula I or formula II wherein X is S(O)$_n$ and n is 1 or 2, respectively, can be optionally prepared by methods well known to one skilled in the art, such as for example, treating a solution of Boc protected compound 8a or 11a (scheme 2) with H$_2$O$_2$ and Na$_2$CO$_3$. Alternatively, Boc protected compound 7 or 10 (scheme 2) can be treated with a suitable base such as for example sodium hydride or cesium carbonate followed by treatment with an arylsulfonyl chloride, an arylsulfinyl chloride, a heterocyclesulfonyl chloride or a heterocyclesulfinyl chloride (used in place of the diaryldisulfide or diheterocycledisulfide) as described above for scheme 2 step f. The sulfinyl and sulfonyl intermediates from these reactions can be hydrolyzed to remove the Boc protecting group and then each of the resulting deprotected intermediates can be converted to compounds of formula I or formula II wherein X is S(O)$_n$, n is 1 or 2, and R$_3$ is aryl or heterocycle by methods as disclosed herein.

Scheme 5

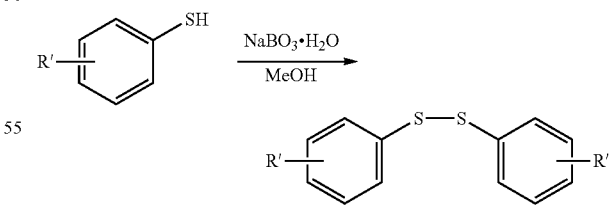

As shown in scheme 5, diaryldisulfides are prepared by treating a solution of an arylsulfide in a suitable organic solvent, such as for example methanol, with an aqueous solution of sodium perborate and allowing the mixture to stand for about 12 hours to about 24 hours at ambient temperature. The diaryldisulfide may be isolated and purified by methods as are well known to one skilled in the art. Diheterocycledisulfides, such as for example bis(2-pyridinyl)disulfide, are prepared in a similar manner. The arylsulfide and heterocyclesulfide are each optionally substituted as is defined above for "aryl" and "heterocycle".

All of the various embodiments of the compounds of this invention as disclosed herein can be used in the methods for treating various diseases and disorders as described herein. As stated herein the compounds used in the methods of this invention are capable of inhibiting the effects of casein kinase Iε.

One embodiment of this invention relates to a method for inhibiting casein kinase Iε activity in a patient by administering to said patient a therapeutically effective amount of an inhibitor of casein kinase Iε wherein said inhibition of casein kinase Iε activity results in a lengthening of circadian rhythm period.

Another embodiment of this invention relates to a method for inhibiting casein kinase Iε activity in a patient resulting in a lengthening of circadian rhythm period comprising administering to said patient a therapeutically effective amount of a compound of formula I or formula II of the invention. Another embodiment of the present invention relates to a method for treating a patient suffering from a disease or disorder ameliorated by inhibition of casein kinase Iε activity that comprises administering to said patient a therapeutically effective amount of a compound of formula (I) or formula (II) that results in a lengthening of circadian rhythm period.

A further embodiment of this invention provides a method for treating a mood disorder or a sleep disorder. Another embodiment of the present invention provides a method for treating mood disorder wherein the mood disorder is a depressive disorder or a bipolar disorder. A further embodiment of the present invention provides a method for treating a depressive disorder wherein the depressive disorder is major depressive disorder. Another embodiment of the present invention provides a method for treating mood disorder wherein the mood disorder is bipolar disorder. A further embodiment of this invention provides a method for treating bipolar disorder wherein the bipolar disorder is selected from the group consisting of bipolar I disorder and bipolar II disorder. Another embodiment of the present invention provides a method for treating a sleep disorder. A further embodiment of the present invention provides a method for treating sleep disorder wherein the sleep disorder is a circadian rhythm sleep disorder. A further embodiment of the present invention provides a method for treating circadian rhythm sleep disorder wherein the circadian rhythm sleep disorder is selected from the group consisting of shift work sleep disorder, jet lag syndrome, advanced sleep phase syndrome and delayed sleep phase syndrome. One skilled in the art readily appreciates that the diseases and disorders expressly stated herein are not intended to be limiting but rather to illustrate the efficacy of the compounds of the present invention. Thus, it is to be understood that the compounds of the invention may be used to treat any disease or disorder ameliorated by the inhibition of casein kinase Iε.

In another embodiment of the invention, pharmaceutical compositions comprising a pharmaceutically acceptable carrier and a compound of formula I or formula II, or a stereoisomer, an enantiomer, a racemate or a tautomer of said compound; or a pharmaceutically acceptable salt thereof, are prepared in a manner well known to one skilled in the pharmaceutical arts. The carrier or excipient may be a solid, semisolid or liquid material which can serve as a vehicle or medium for the active ingredient. Suitable carriers or excipients are well known in the art. The pharmaceutical composition may be adapted for oral, inhalation, parenteral or topical use, and may be administered to the patient in the form of tablets, capsules, suspensions, syrups, aerosols, inhalants, suppositories, salves, powders, solutions and the like. As used herein, the term "pharmaceutical carrier" or "pharmaceutically acceptable carrier" means one or more excipients. As described herein, the pharmaceutical compositions of the invention provide inhibition of casein kinase Iε and are thus useful for the treatment of diseases or disorders ameliorated by inhibition of casein kinase Iε

In preparing pharmaceutical compositions or formulations of the compounds of the present invention, care should be taken to ensure bioavailability of an effective therapeutic amount of the active compound or compounds by the selected route of administration, including oral, parenteral and subcutaneous routes. For example, effective routes of administration include subcutaneous, intravenous, transdermal, intranasal, rectal, vaginal and the like routes including release from implants as well as injection of the active ingredient and/or composition directly into the tissue.

For oral administration, the compounds of the present invention can be formulated into solid or liquid preparations, with or without inert diluents or edible carriers, such as capsules, pills, tablets, troches, powders, solutions, suspensions or emulsions. The capsules, pills, tablets, troches and the like may also contain one or more of the following adjuvants: binders such as microcrystalline cellulose, gum tragacanth; excipients such as starch or lactose, disintegrating agents such as alginic acid, corn starch and the like; lubricants such as stearic acid, magnesium stearate or Sterotex®, (Stokely-Van Camp Inc., Indianapolis, Ind.) glidants such as colloidal silicon dioxide; sweetening agents such as sucrose or saccharin; and flavoring agents such as peppermint, methyl salicylate or fruit flavoring. When the dosage unit form is a capsule, it may also contain a liquid carrier such as polyethylene glycol or a fatty oil. Materials used should be pharmaceutically pure and nontoxic in the amounts used. Alternatively, the pharmaceutical compositions may be prepared in a form suitable for extended release to provide a therapeutic amount of a compound of the present invention in a suitable once daily, once weekly or once monthly form using methods as are will known to one skilled in the art. For example, an erodible polymer containing the active ingredient may be envisaged.

For parenteral administration, the compounds of the present invention may be administered as injectable dosages of a solution or suspension of the compound in a physiologically acceptable diluent with a pharmaceutical carrier which can be a sterile liquid such as water-in-oil or without the addition of a surfactant and other pharmaceutically acceptable excipients. Illustrative oils which can be employed in the preparations are those of petroleum, animal, vegetable or synthetic origin such as, for example, peanut oil, soybean oil and mineral oil. In general, water, saline, aqueous dextrose and related sugar solutions, ethanol and glycols, such as propylene glycol are preferred liquid carriers, particularly for injectable solutions. The parenteral preparation can be enclosed in ampoules, disposable syringes or multiple dose vials made of inert plastic or glass.

The solutions or suspensions described above may also include one or more of the following adjuvants: sterile diluents such as water for injection, saline solution, fixed oils, polyethylene glycols, glycerin, propylene glycol or other synthetic solvents, antibacterial agents such as ascorbic acid or sodium bisulfite; chelating agents such as ethylenediamine-tetra-acetic acid; buffers such as acetates, citrates or phosphates and agents for the adjustment of tonicity such as sodium chloride or dextrose.

The compounds of the present invention can be administered in the form of a cutaneous patch, a depot injection or implant preparation which can be formulated in such a manner as to permit a sustained release of the active ingredient. The active ingredient can be compressed into pellets or small cylinders and implanted subcutaneously or intramuscularly as depot injections or implants. Implants may employ inert materials such as biodegradable polymers and synthetic silicones. Suitable pharmaceutical carriers and formulation techniques are found in standard texts, such as Remington: The Science and Practice of Pharmacy, 19$^{th}$ edition, Volumes 1 and 2, 1995, Mack Publishing Co., Easton, Pa., U.S.A., which is herein incorporated by reference.

In the treatment of various diseases, disorders and conditions as described herein, a suitable dosage level is about 0.01 mg/kg per day to about 250 mg/kg per day, preferably about 0.05 mg/kg per day to about 100 mg/kg per day, and especially about 0.05 mg/kg per day to about 40 mg/kg per day. The compounds of the present invention may be administered on a regimen of 1 to 4 times per day and as dictated by the nature of the disease, disorder or condition to be treated.

EXAMPLES

The following examples are intended to serve for the illustration of the invention in greater detail, without restricting the breadth of the invention in any manner. Tables 1 and 2 provide summaries of the example compounds prepared as described below.

Unless otherwise noted, materials were obtained from commercial suppliers and used without further purification. All reactions were run under inert atmosphere with dry reagents and solvents. Flash chromatography was carried out on an Isco CombiFlash Companion™ using Advantage FlashReady™ prepacked silica cartridges and the solvent systems as described. Thin layer chromatography was performed using 0.25 mm silica gel coated 60F-254 plates (EM) and visualized using iodine vapor, UV light, or a staining reagent such as $KMnO_4$ solution.

Infrared (IR) spectra were recorded on a Nexus 670 FTIR (Nicolet) spectrometer with samples prepared as indicated, and are reported in wave numbers ($cm^{-1}$). $^1H$ NMR spectra were recorded on a Varian Gemini and/or mercury 300, Unity 400, or Unity plus and/or Inova 500 MHz spectrometers with chemical shifts (δ) reported in ppm relative to tetramethylsilane (0.0 ppm) or chloroform ($CDCl_3$, 7.26 ppm) as a reference. $^{13}C$ NMR spectra were recorded on a Varian Unity instrument (100.57 MHz, 13C frequency) with chemical shifts (δ) reported in ppm relative to $CDCl_3$ (77.0 ppm), unless stated otherwise. Mass spectra (MS) were obtained on a Finnegan MAT Model TSQ 700 Mass Spectrometer System by chemical ionization at 120 eV using methane (Cl, 120 eV). Liquid Chromatography Mass Spectrometry (LCMS) was performed on a Micromass LCT interfaced with a Gilson 215 liquid handler. High resolution mass spectrometric analysis (exact mass spectra) was performed in the ESI mode at mass resolution of 10,000 using a Micromass QTOF mass spectrometer. Exact mass values were determined for the protonated molecular ions (M+1) wherein M refers to the molecular ion. Reductive aminations using a resin bound reducing agent were performed using Argonaut Macroporous (MP) polystyrene-co-divinylbenzene. The MP-Cyanoborohydride reagent was Lot No. 01617 with a loading of 2.55 mmol/g.

General Synthetic Procedures

General Synthetic Procedure Ia (Preparation of 3-arylthio- or 3-heterocyclethio-indole-2-carboxylic acid amides using NaH)

To a stirred suspension of NaH (60% oil disp., 1.2 equiv, 9.8 mmol) in DMF (75 mL) under $N_2$ at rt, add the indole-2-carboxyamide (8.18 mmol) as a DMF solution (5 mL). After 5 minutes, add the diaryldisulfide or diheterocycledisulfide (1.0 equiv., 8.18 mmol) in one portion and heat the reaction with stirring to 95° C. for 16 h. Follow the reaction by partitioning an aliquot between $EtOAc/H_2O$ and monitor the aliquot by tlc (10% $MeOH/CH_2Cl_2$). Concentrate the reaction in vacuo, dilute with $H_2O$ and stir for 30 min, filter and air-dry. Chromatograph the crude solid on $SiO_2$ and elute with 9:1 $CH_2Cl_2/MeOH$ to provide the 3-arylthio or 3-heterocyclethio-indole-2-carboxylic acid amide. (reference: Atkinson et al. Syn. Comm. 1988, 480.)

General Synthetic Procedure Ib (Preparation of 3-arylthio- or 3-heterocyclethio-indole-2-carboxylic acid amides using $Cs_2CO_3$)

To the indole-2-carboxyamide (1.06 mmol) dissolved in dry DMF (10 mL), add $Cs_2CO_3$ (100 mg, 0.31 mmol) and then add the diaryldisulfide or diheterocycledisulfide (0.64 mmol). Heat the reaction under $N_2$ at 100° C. for 2.5 h (monitor by tlc/LC-MS for completion). Allow reaction to cool to rt, concentrate to minimum volume and partition between brine (6 mL) and EtOAc (3 mL). Extract with EtOAc, dry the combined extracts ($MgSO_4$) and concentrate to provide the crude is product. Purify the crude product on an ISCO (4.0 g $SiO_2$) column to afford the 3-arylthio or 3-heterocyclethio-indole-2-carboxylic acid amide.

General Synthetic Procedure II (Transesterification)

Add $K_2CO_3$ (1.20 equiv, 50.7 mmol) to the ethyl indole-2-carboxylate (42.3 mmol) in MeOH (50 mL) and stir the suspension with heating to 55° C. for 1 h. Monitor by tlc ($Et_2O$/hept) and upon completion concentrate in vacuo, dilute with $H_2O$ and stir for 15 min. Collect the solid by filtration and dry in a vacuum oven at 65° C. for 3 h to provide the methyl indole-2-carboxylic acid ester.

General Synthetic Procedure III (Amidation Using $NH_4OH$)

Stir the ethyl or methyl indole-2-carboxylic acid ester (40.0 mmol) as a suspension in $NH_4OH$ (100 mL) and LiCl (1.0 equiv) at rt for 16 h. Collect the solid by filtration from the reaction, wash with $H_2O$ and air dry to give the indole-2-carboxylic acid amide.

General Synthetic Procedure IV (Amidation Using $NH_3/MeOH$)

Stir the ethyl or methyl indole-2-carboxylic acid ester (4.67 mmol) in 7N $NH_3/MeOH$ (20 mL) and add LiCl (1.0 equiv, 4.67 mmol). Stir the reaction at rt for 5 days and monitor by tlc (10% $MeOH/CH_2Cl_2$). A precipitate may form during this period. Concentrate the mixture to minimum volume, dilute with $H_2O$ and filter off the solid. Wash the solid with additional $H_2O$ and dry under vacuum at 60° C. to afford the indole-2-carboxylic acid amide as a solid.

General Synthetic Procedure V (the 2-indole carboxylic acid from the ethyl or methyl ester)

To ethyl or methyl indole-2-carboxylic acid ester (27.0 mmol) as a suspension in MeOH/H$_2$O (3:1, 160 mL) add NaOH (82.0 mmol). Stir at rt for 16 h, concentrate the reaction, acidify with HCl and collect the precipitate by filtration. Wash the filter cake with additional H$_2$O and dry in a vacuum oven to afford the 2-indole carboxylic acid.

General Synthetic Procedure VI (Amidation of the 2-indole carboxylic acid)

Add to the 2-indole carboxylic acid (31.0 mmol) dissolved in anhydrous THF (50 ml), carbonyldiimidazole (1.10 equiv, 5.5 g, 34.0 mmol) and stir 1 h. Then add concentrated NH$_4$OH (50 mL) in one portion and stir the reaction at rt. After 16 hours collect the solid that separates by filtration, wash with H$_2$O and dry under vacuum at 40° C. to afford the desired 2-indole carboxamide.

General Synthetic Procedure VII (Amidation Using Primary and Secondary Amines from the 2-indole carboxylic acid)

Add to the 2-indole carboxylic acid (12.4 mmol) in anhydrous THF (30 ml), carbonyldiimidazole (1.5 equiv, 18.6 mmol) and stir for 1 h. Add the desired amine [for example, methylamine, ethylamine, dimethylamine, pyrrolidine, piperidine, piperazine, or morpholine, (3.0 equiv, 37.2 mmol)] in one portion and stir the reaction at rt. After 16 hours, quench the reaction with H$_2$O, collect the resulting precipitate by filtration and dry under vacuum to afford the desired 2-indole carboxamide.

General Synthetic Procedure VIII (N-alkylation of the aminomethylindole)

Treat the 5- or 6-Boc-aminomethylindole, (0.5 mmol) with trifluoroacetic acid (TFA, 5 mL) and H$_2$O (0.25 mL) and stir at rt for ten minutes (monitor by lc/ms). Precipitate the trifluoroacetate salt by addition of Et$_2$O, collect the salt by filtration and dry under vacuum at 70° C. Dissolve the TFA salt (0.24 mmol) in DMF (3.0 mL), treat with K$_2$CO$_3$ (0.48 mmol) then add the desired alkyl halide (0.50 mmol). After 4 h or when the reaction is complete by tlc (10% MeOH/CH$_2$Cl$_2$– 0.25% NH$_3$), dilute the reaction with EtOAc, wash with H$_2$O, dry (MgSO$_4$) and concentrate. Purify the crude product by chromatography to afford the desired 5- or 6-alkylaminomethylindole.

General Synthetic Procedure IX (Reductive Amination of the 5- or 6-Aminomethylindole with MP-CNBH$_3$)

Neutralize a solution of the 5- or 6-aminomethylindole TFA salt (0.061 mmol) and AcOH/THF (1:4, 2.5 mL) by addition of K$_2$CO$_3$ (1.0 equiv, 0.061 mmol). To this mixture add the desired aldehyde (1.0 equiv, 0.061 mmol) and stir the reaction at rt for 10 min. Syringe the reaction mixture into a polypropylene disposable syringe (5 mL, HSW) equipped with a polypropylene septum and cap and charged with MP-CNBH$_3$ resin (2.5 equiv). Place the syringe on an LabQuake Shaker and rotate for 16 h. Monitor the reaction by tlc (10% MeOH/CH$_2$Cl$_2$) and when complete syringe the reaction mixture into a dram vial, combine with a THF wash of the resin and concentrate under vacuum. In some cases to obtain crystalline material, treat the amorphous solid with HCl (1.0 mL) and precipitate with EtO$_2$ (1.0 mL) to give the HCl salt.

General Synthetic Procedure X (Reductive Amination of 5- and 6-formyl-3-phenylsulfanyl-1H-indole-2-carboxylic acid amide with MP-CNBH$_3$)

Add to the 5- or 6-indole aldehyde (0.077 mmol) in AcOH/THF (1:4, 2.5 mL), the desired primary or secondary amine (2 equiv., 0.152 mmol) and allow the reaction to stand at rt. After 40 minutes, syringe the reaction mixture into a polypropylene disposable syringe (5 mL, HSW) equipped with a polypropylene septum and cap and charged with MP-CNBH$_3$ resin (2.0 equiv). Place the syringe on an LabQuake Shaker and rotate for 16 hours. Where an amine HCl salt is used, add Et$_3$N (1.1 equiv) to neutralize the salt. Monitor the reaction by tlc (10% MeOH/CH$_2$Cl$_2$) and when complete syringe the reaction mixture into a dram vial, combine with a THF wash of the resin and concentrate under vacuum to afford the product.

General Synthetic Procedure XI (Reduction of Nitrile with Raney Nickel)

Reduce the 5- or 6-indole nitrile as described by Sundberg, R. J.; Dalhausen, D. J.; Manikumar, G.; Mavunkel, B.; Biswas, A. et al. J. Heterocyclic Chem. 1988, 25, 129-137. Thus, suspend the 5- or 6-cyano-3-phenylsulfanyl-1H-indole-2-carboxylic acid amide (4.59 mmol) and NaH$_2$PO$_2$ (3.0 equiv, 13.7 mmol) in a solution of pyridine (20 mL), AcOH (10 mL) and H$_2$O (10 mL). Add to this mixture a water slurry of Raney Ni (1.0 mL) and heat the reaction to 95° C. for 4.5 h. Cool the reaction mixture, filter through Celite® (diatomaceous earth) (Celite Corporation, 137 West Central Avenue, Lompor, Calif. 93436) under N$_2$ and wash sparingly with pyridine and H$_2$O. Concentrate the filtrate under vacuum to a minimum volume, dilute the dark green oil with ice-H$_2$O and stir for 5 min at which time a precipitate forms. Collect the precipitate by filtration, wash with Et$_2$O and air dry to afford the 5- or 6-formyl product, respectively.

General Synthetic Procedure XII (Reductive Amination of the 5- or 6-aminomethyl indole with NaBH$_3$CN)

Add to a solution of the 5- or 6-aminomethylindole TFA salt (0.12 mmol) and AcOH/THF (1:4, 5.0 mL), the desired aldehyde (0.108 mmol) and then add K$_2$CO$_3$ (1.0 equiv, 0.12 mmol) and NaCNBH$_3$ (2.5 equiv, 0.3 mmol). Stir the reaction at rt and monitor by tlc (10% MeOH/CH$_2$Cl$_2$). When complete, dilute the reaction with EtOAc, wash with sat. NaHCO$_3$ and brine, dry (MgSO$_4$) and concentrate in vacuo to give the crude product. Purify the crude product by chromatography to afford the desired compound.

General Synthetic Procedure XIII (Reductive Amination of the 5-formyl-3-phenylsulfanyl-1H-indole-2-carboxylic acid amide Using NaBH$_3$CN)

To a solution of aldehyde 13 or the N-alkylated aldehyde 14 (0.26 mmol) and AcOH/THF (1:4, 5.0 mL), add the desired amine (0.52 mmol) and then add Et$_3$N(1.0 equiv, 0.26 mmol) followed by NaCNBH$_3$ (2.5 equiv, 0.65 mmol). Stir the reaction at rt and monitor by tlc (10% MeOH/CH$_2$Cl$_2$). When complete, dilute the reaction mixture with EtOAc, wash with sat. NaHCO$_3$ and brine, dry (MgSO$_4$) and concentrate in vacuo to give the crude product. Purify the crude product to afford the desired compound. A small amount of the bis-alkylation product occurs as a by-product.

General Synthetic Procedure XIV (N-methylation of 5-formyl-3-phenylsulfanyl-1H-indole-2-carboxylic acid amide)

To the indole aldehyde 13 (400 mg, 1.35 mmol) dissolved in DMF (20 mL) add KOH (1.2 equiv, 91.0 mg) as a aqueous solution (3.0 mL, $H_2O$). Add to the reaction a solution of MeI (101 µL) and DMF (1.0 mL), dropwise. Stir the reaction at rt for 48 h. Dilute the reaction with EtOAc (200 mL), and wash the organic phase with sat. $NaHCO_3$ and dry ($MgSO_4$). Concentrate the organic phase to give the crude product 14.

General Synthetic Procedure XV (Coupling of Amino Acids with the 5- or 6-aminomethylindole)

Dissolve the 5- or 6-aminomethylindole (0.242 mmol, 8b or 11b as the trifluoroacetate salt) in DMF (10 mL), add 10% aqueous $K_2CO_3$ (1.0 mL) and then add the N-Boc-protected amino acid N-hydroxysuccinimide ester (1.10 equiv, 0.266 mmol). Stir at rt and monitor the reaction by LC/MS. Upon completion, dilute the reaction with EtOAc (200 mL) and wash the organic phase with sat. $NaHCO_3$ (3×) and brine (1×), dry ($MgSO_4$) and concentrate in vacuo. Deprotect the crude amino acid analog by treating with 99% TFA for 10 min, concentrate and then precipitate the product as the TFA salt by addition of $Et_2O$.

Preparation of 5- and 6-cyano-1H-indole-2-carboxylic acid ethyl and methyl esters Scheme 1

3-(5-Cyano-2-nitrophenyl)-2-oxo-propionic acid ethyl ester, 2 (m=0)

Dissolve sodium metal (0.345 g) in absolute EtOH (25 mL), add diethyloxalate (10 mL) and then add 3-methyl-4-nitrobenzonitrile (1a, m=0, 1.6 g, Aldrich) as an EtOH solution (25 mL). Stir reaction mixture at rt for 16 h, neutralize the reaction by addition of 5N HCl (3 mL) and remove the EtOH under reduced pressure. Partition the residue between $CH_2Cl_2$ (100 mL) and $H_2O$ (50 mL). Wash the organic layer successively with $H_2O$ (50 mL) and brine (50 mL), dry ($MgSO_4$) and concentrate to give a crude oil. Purify the oil by chromatography on $SiO_2$ (cyclohexane-EtOAc, 70-30 v/v) to give after drying (40° C., house vacuum), the title compound (1.2 g) as yellow crystals.

5-Cyano-1H-indole-2-carboxylic acid ethyl ester, 3a (m=0)

Add to 1.2 g 3-(5-cyano-2-nitrophenyl)-2-oxopropionic acid ethyl ester 2 (m=0) in EtOH (40 mL), 10% Pd/C (0.40 g) and stir under a hydrogen atmosphere until the theoretical amount of hydrogen is absorbed. Filter the mixture and concentrate the filtrate to afford 1.1 g of crude product. Purify by chromatography on $SiO_2$ eluting with $CH_2Cl_2$. Concentrate the desired fractions and vacuum dry the residue over night (40° C.) to provide the title compound (0.5 g) as white crystals, Rf=0.9 (silica gel, 10% MeOH/$CH_2Cl_2$).

3-(4-Cyano-2-nitrophenyl)-2-oxo-propionic acid ethyl ester, 4 (m=0)

Dissolve sodium metal (0.345 g) in absolute EtOH (25 mL), add diethyloxalate (10 mL) and then add 4-methyl-3-nitrobenzonitrile (1b, m=0, 1.6 g, Aldrich) as an EtOH solution (25 mL). Stir the reaction mixture at rt for 16 hours, neutralize the reaction by addition of 5N HCl (3 mL) and remove the EtOH under reduced pressure. Partition the residue between $CH_2Cl_2$ (100 mL) and $H_2O$ (50 mL). Wash the organic layer successively with $H_2O$ (50 mL) and brine (50 mL), dry ($MgSO_4$) and concentrate to give a crude oil. Purify the oil by chromatography on $SiO_2$ eluting with cyclohexane-EtOAc, 70-30 v/v, to afford gave after drying (40° C., house vacuum), the title compound (1.5 g) as yellow crystals, mp 118° C.

6-Cyano-1H-indole-2-carboxylic acid ethyl ester, 5a (m=0)

Add to 1.5 g of 3-(4-cyano-2-nitrophenyl)-2-oxopropionic acid ethyl ester, in EtOH (40 mL) 10% Pd/C (0.45 g) and stir under a hydrogen atmosphere until the theoretical amount of hydrogen is absorbed. Filter the mixture and concentrate the filtrate to afford 1.1 g of crude product. Purify by chromatography on $SiO_2$ and elute with $CH_2Cl_2$. Concentrate the desired fractions and vacuum dry the residue over night (40° C.) to afford the title compound (0.8 g) as white crystals, mp 176° C.

5-Cyano-1H-indole-2-carboxylic acid methyl ester, 3b (m=0) and 6-Cyano-1H-indole-2-carboxylic acid methyl ester, 5b (m=0)

The title esters 3b and 5b can each be prepared from the corresponding ethyl esters 3a and 5a, respectively, by transesterification as described in General Synthetic Procedure II.

Preparation of 3-arylthio- or 3-heterocyclethio-5-aminomethylindole-2-carboxylic acid amides 8b and 3-arylthio- or 3-heterocyclethio-6-aminomethylindole-2-carboxylic acid amides 11b Scheme 2

5-Cyano-1H-indole-2-carboxylic acid amide, 6 (m=0)

Treat 5-cyano-1H-indole-2-carboxylic acid ethyl ester, 3a (m=0, 1.0 g, 4.67 mmol) with 7 N $NH_3$/MeOH as described in General Procedure IV to afford the title compound as an ivory colored solid (720 mg, 83.3%): mp>300° C.; $^1$H NMR (DMSO-$d_6$) δ 12.0 (brs, 1H), 8.21 (s, 1H), 8.14 (brs, 1H), 7.51 (m, 3H), 7.25 (s, 1H); tlc (10% MeOH/$CH_2Cl_2$) Rf=0.40, m/z obs=186 (M+1).

(2-Carbamoyl-1H-indol-5-ylmethyl)-carbamic acid tert-butyl ester, 7 (m=0)

Dissolve indole 6 (m=0, 9.5 g, 51.3 mmol) in MeOH (500 mL) and add $NiCl_2$ (7.3 g, 1.1 equiv, 56.4 mmol) and $Boc_2O$ (22.4 g, 2.0 equiv, 102.6 mmol). Cool the mixture to ice bath temperature and then add $NaBH_4$ (13.6 g, 7.0 equiv, 0.36 mol). Stir the reaction at rt under $N_2$. After 16 h, concentrate the reaction, dissolve the residue in EtOAc, wash with sat. $NaHCO_3$ and extract several times with EtOAc. Combine the extracts, dry ($MgSO_4$) and concentrate to give the title compound 7 (m=0) that is used without further purification. Rf=0.30, m/z obs=290 (M+1). (reference: Caddick, S, et al. Tet. Lett. 2000, 41, 3513-16).

(2-Carbamoyl-3-phenylsulfanyl-1H-indol-5-ylmethyl)-carbamic acid tert-butyl ester, 8a (m=0, $R_3$=Ph)

Treat amide 7 (m=0, 4.0 g, 13.8 mmol) with phenyldisulfide (1.0 equiv, 3.02 g, 13.8 mmol) as described in General Procedure I to give the title compound 8a (compound Ib wherein m=0) as a pale yellow solid (2.36 g, 42.9%); $^1$H NMR (DMSO-$d_6$) δ 12.2 (brs, 1H), 7.94 (brs, 1H), 7.71 (brs, 1H), 7.5-6.9 (m, 9H), 4.17 (d, 2H, J=6.0 Hz), 1.40 (s, 9H). tlc (5% MeOH/$CH_2Cl_2$) Rf=0.25, m/z obs=398 (M+1).

5-Aminomethyl-3-phenylsulfanyl-1H-indole-2-carboxylic acid amide, 8b (m=0, $R_3$=Ph)

Treat the 5-Boc-aminomethyl compound 8a (m=0, $R_3$=Ph; Ib) (1.6 g) with TFA (99%, 10 mL) and stir at rt for 10 min. Concentrate the reaction and precipitate the product by addition of $Et_2O$ to provide the TFA salt of the title compound 8b (compound Ia wherein (m=0, $R_3$=Ph)) as a white solid (1.6 g): $^1$H NMR (DMSO-$d_6$) δ 12.5 (brs, 1H), 7.92 (brs, 1H), 7.70 (brs, 1H), 7.5-6.9 (m, 10H), 4.17 (d, 2H, J=6.2 Hz).

6-Cyano-1H-indole-2-carboxylic acid amide, 9 (m=0)

Treat 6-cyano-1H-indole-2-carboxylic acid ethyl ester 5a (m=0, 1.0 g, 4.67 mmol) with 7 N $NH_3$/MeOH as described in General Procedure IV to afford the title compound as an ivory colored solid (766 mg, 88.6%), mp 241-242° C.; $^1$H NMR (DMSO-$d_6$) δ 11.5 (brs, 1H), 8.16 (brs, 1H), 7.83 (s, 1H), 7.80 (d, 1H, J=8.0 Hz), 7.58 (brs, 1H), 7.35 (d, 1H, J=8.0 Hz), 7.23 (s, 1H).

(2-Carbamoyl-1H-indol-6-ylmethyl)-carbamic acid tert-butyl ester, 10 (m=0)

Dissolve indole 9 (m=0, 0.56 g, 3 mmol) in MeOH (25 mL), stir at rt under $N_2$, and add $NiCl_2$ (0.36 g, 1.0 equiv, 3.0 mmol) and $Boc_2O$ (1.31 g, 2.0 equiv, 6.0 mmol). Cool the mixture to ice bath temperature and then add $NaBH_4$ (0.79 g, 21 mmol). Stir the reaction at rt under $N_2$. After 16 h, concentrate the reaction, dissolve the residue in EtOAc, wash with sat $NaHCO_3$ and extract several times with EtOAc. Combine the extracts, dry ($MgSO_4$) and concentrate to give the title compound (433 mg, 49.5%) as a yellow crystalline solid which is used without further purification, mp 209-209.5° C.; $^1$H NMR (DMSO-$d_6$) δ 11.4 (brs, 1H), 7.87 (brs, 1H), 7.49 (d, 1H, J=8.0 Hz), 7.27 (s overlapping a brs, 3H), 7.06 (s, 1H), 6.92 (d, 1H, J=8.1 Hz), 4.18 (d, 2H, J=5.9 Hz), 1.40 (s, 9H). tlc (10% MeOH/$CH_2Cl_2$) Rf=0.35, m/z obs=290 (M+1).

(2-Carbamoyl-3-phenylsulfanyl-1H-indol-6-ylmethyl)-carbamic acid tert-butyl ester, Ia (m=0, $R_3$=Ph)

Treat amide 10 (m=0, $R_3$=Ph; 411 mg, 1.42 mmol) with phenyldisulfide (310 mg, 1.42 mmol) as described in General Procedure I to give the title compound 11a (compound IIb wherein m=0 and $R_3$ is Ph) as a tan solid (60 mg, 10.6%), mp 118-121° C.; $^1$H NMR (DMSO-$d_6$) δ 12.25 (brs, 1H), 7.90 (brs, 1H), 7.70 (brs, 1H), 7.52 (m, 2H), 7.40 (m, 3H), 7.37-7.0 (m, 4H), 4.19 (d, 2H, J=6.4 Hz), 1.40 (s, 9H). tlc (10% MeOH/$CH_2Cl_2$) Rf=0.55, m/z obs=398 (M+1).

6-Aminomethyl-3-phenylsulfanyl-1H-indole-2-carboxylic acid amide-TFA salt, 11b (m=0, $R_3$=Ph)

Treat the 6-Boc-aminomethyl compound 11a (m=0, $R_3$=Ph; 1.6 g) with TFA (99%, 10 mL) and stir at rt for 10 min. Concentrate the reaction and precipitate the product by addition of $Et_2O$ to provide the title compound 11b (compound IIa wherein m=0 and $R_3$ is Ph) as a white solid (1.6 g): $^1$H NMR (DMSO-$d_6$) δ 12.55 (s, 1H), 8.14 (brs, 1H), 8.05 (s, 1H), 7.75 (brs, 1H), 7.64 (s, 1H), 7.51 (d, 1H), 7.3-7.0 (m, 6H), 4.15 (d, 2H, J=5.8 Hz). tlc (10% MeOH/$CH_2Cl_2$) Rf=0.55, m/z obs=398 (M+1).

Preparation of 3-arylthio- and 3-heterocyclethio-5-formylindole-2-carboxylic acid amides 13 and 14, and 5-N-substituted-aminomethylindole-2-carboxylic acid amides 16

Scheme 3

5-Cyano-3-phenylsulfanyl-1H-indole-2-carboxylic acid amide. 12 (m=0, $R_3$=Ph)

Treat compound 6 (m=0, 6.0 g, 32.4 mmol) with diphenyldisulfide (1.10 equiv, 7.78 g) as described in General Synthetic Procedure I to give the crude title compound 12 (6.5 g, 68.4%) as an ivory colored solid which is used without purification, Rf=0.5 (5% MeOH/$CH_2Cl_2$).

5-Formyl-3-phenylsulfanyl-1H-indole-2-carboxylic acid amide, 13 (m=0, $R_3$=Ph)

Reduce compound 12 (m=0, $R_3$=Ph; 1.13 g, 3.86 mmol) with Raney nickel (90.7 g) as described in General Synthetic Procedure XI to give, after chromatography on $SiO_2$ (2% MeOH/$CH_2Cl_2$), the title compound 13 (0.69 g, 60%) as pale a yellow solid, Rf=0.45 (5% MeOH/$CH_2Cl_2$).

5-Formyl-1-methyl-3-phenylsulfanyl-1H-indole-2-carboxylic acid amide, 14 (m=0, $R_1$=$CH_3$, $R_3$=Ph)

Treat 5-formyl-3-phenylsulfanyl-1H-indole-2-carboxylic acid amide 13 (m=0, $R_3$=Ph; 400 mg, 1.35 mmol) with MeI (101 μl) as described in General Procedure XIV to provide the 5-formyl-1-methylindole the title compound 14 (280 mg, 67%), Rf (5% MeOH/$CH_2Cl_2$)=0.75.

5-Formyl-1H-indole-2-carboxylic acid amide, 15 (m=0)

Treat 5-cyano-1H-indole-2-carboxylic acid amide 6 (m=0, 500 mg, 2.7 mmol) with Raney nickel (0.6 g) as described in General Procedure XI to afford the title compound 15 (230 mg, 45.4%) as a yellow solid, tlc (10% MeOH/$CH_2Cl_2$), Rf=0.75.

5-Methylaminomethyl-1H-indole-2-carboxylic acid amide, 16 (m=0, $R_8$=$CH_3$)

Treat aldehyde 15 (m=0, 230 mg, 1.22 mmol) with methylamine hydrochloride (2.0 equiv, 165 mg, 2.44 mmol) and $NaBH_3CN$ (3 equiv, 239 mg, 3.7 mmol) as described in General Procedure XII to afford the title compound 16 (230 mg, 92.7%) as a tan solid; tlc (10% MeOH/$CH_2Cl_2$–0.2% $Et_3N$) Rf=0.25, m/z obs=204 (M+1).

Preparation of 5-substituted-3-arylthioindole-2-carboxylic acid amides I from 8b, 13, 14 and 16

Schemes 2 and 4

5-Aminomethyl-3-phenylsulfanyl-1H-indole-2-carboxylic acid amide, Ia and (2-Carbamoyl-3-phenylsulfanyl-1H-indol-5-ylmethyl)-carbamic acid tert-butyl ester, Ib Title compounds Ia and Ib are prepared as is described above for the synthesis of compounds 8a and 8b according to scheme 2.

5-Methyaminomethyl-3-phenylsulfanyl-1H-indole-2-carboxylic acid amide, Ic

Treat 5-formyl-3-phenylsulfanyl-1H-indole-2-carboxylic acid amide 13 (m=0, $R_3$=Ph) (50 mg, 0.17 mmol) with methylamine HCl (2.0 equiv, 23 mg, 0.34 mmol) as described in General Procedure X to afford 5-methylaminomethyl-3-phenylsulfanyl-1H-indole-2-carboxylic acid amide, Ic (18 mg, 34.6%) as a yellow solid, tlc Rf=0.2 (15% MeOH/$CH_2Cl_2$), m/z obs=312 (M+1).

3-(3-Chlorophenylsulfanyl)-5-methylaminomethyl-1H-indole-2-carboxylic acid amide, Id Treat 5-methylamino-1H-indole-2-carboxylic acid amide 16 (m=0, $R_8$=$CH_3$) (50 mg, 0.25 mmol) with 3-chlorophenyl disulfide (77.8 mg, 0.27 mmol) as described in General Procedure Ib to afford Id as an ivory colored solid (22 mg, 25.8%), tlc Rf=0.15 (50% MeOH/$CH_2Cl_2$–0.5% $Et_3N$).

3-(3-Fluorophenylsulfanyl)-5-methylaminomethyl-1H-indole-2-carboxylic acid amide, Ie Treat 5-methylamino-1H-indole-2-carboxylic acid amide 16 (m=0, $R_8$=$CH_3$) (65 mg, 0.32 mmol) with 3-fluorophenyl disulfide (89.5 mg, 0.352 mmol) as described in General Procedure Ib to afford Ie as an ivory colored solid (42 mg, 40%), tlc Rf=0.15 (50% MeOH/$CH_2Cl_2$–0.5% $Et_3N$).

5-(Benzylaminomethyl)-3-phenylsulfanyl-1H-indole-2-carboxylic acid amide, If

Treat 5-formyl-3-phenylsulfanyl-1H-indole-2-carboxylic acid amide 13 (m=0, $R_3$=Ph) (60 mg, 0.203 mmol) with benzylamine (43.5 mg, 0.406 mmol) as described in General Procedure X to afford If (45 mg, 52.9%) isolated as the HCl salt, m/z obs=388 (M+1).

1-Methyl-5-methylaminomethyl-3-phenylsulfanyl-1H-indole-2-carboxylic acid amide, Ig Treat 5-formyl-1-methyl-3-phenylsulfanyl-1H-indole-2-carboxylic acid amide 14 (m=0, $R_1$=$CH_3$, $R_3$=Ph) (80 mg, 0.26 mmol) with methyl amine hydrochloride as described in General Procedure XIII to afford Ig (37 mg, 44.2%) isolated as the HCl salt, m/z obs=326 (M+1).

5-(4-Hydroxymethylpiperidin-1-ylmethyl)-3-phenylsulfanyl-1H-indole-2-carboxylic acid amide, Ih Treat 5-formyl-3-phenylsulfanyl-1H-indole-2-carboxylic acid amide 13 (m=0, $R_3$=Ph) (50 mg, 0.169 mmol) with 4-piperidine methanol (43.6 mg, 0.338 mmol) as described in General Procedure X to afford Ih (32 mg, 43.9%) isolated as the HCl salt, tlc Rf (free base)=0.25 (10% MeOH/$CH_2Cl_2$–0.5% $Et_3N$), m/z obs=396 (M+1).

5-Morpholin-4-ylmethyl-3-phenylsulfanyl-1H-indole-2-carboxylic acid amide, Ii

Treat 5-formyl-3-phenylsulfanyl-1H-indole-2-carboxylic acid amide 13 (m=0, $R_3$=Ph) (50 mg, 0.169 mmol) with morpholine (29.45 mg, 0.338 mmol) as described in General Procedure X to afford Ii (34 mg, 50.0%) isolated as the HCl salt, tlc Rf (free base)=0.80 (10% MeOH/$CH_2Cl_2$–0.5% $Et_3N$), m/z obs=368 (M+1).

3-Phenylsulfanyl-5-propylaminomethyl-1H-indole-2-carboxylic acid amide, Ij

Treat 5-formyl-3-phenylsulfanyl-1H-indole-2-carboxylic acid amide 13 (m=0, $R_3$=Ph) (50 mg, 0.169 mmol) with propylamine hydrochloride (32.3 mg, 0.338 mmol) as described in General Procedure X to afford Ij (27 mg, 47.3%) isolated as the HCl salt, tlc Rf (free base)=0.40 (10% MeOH/$CH_2Cl_2$–0.5% $Et_3N$), m/z obs=362 [M+23 (Na)].

5-Butylaminomethyl-3-phenylsulfanyl-1H-indole-2-carboxylic acid amide, Ik

Treat 5-formyl-3-phenylsulfanyl-1H-indole-2-carboxylic acid amide 13 (m=0, $R_3$=Ph) (50 mg, 0.169 mmol) with butylamine (15.9 µL, 0.161 mmol) as described in General Procedure X to afford Ik (24 mg, 40.3%) isolated as the HCl salt, tlc Rf (free base)=0.20 (10% MeOH/$CH_2Cl_2$–0.5%$Et_3N$), m/z obs=376 [M+23 (Na)], 354 (M+1).

3-Phenylsulfanyl-5-piperidin-1ylmethyl-1H-indole-2-carboxylic acid amide, Il

Treat 5-formyl-3-phenylsulfanyl-1H-indole-2-carboxylic acid amide 13 (m=0, $R_3$=Ph) (50 mg, 0.169 mmol) with piperidine (33.5 µL, 0.338 mmol) as described in General Procedure X to afford Il (30.0 mg, 48.7%) isolated as the HCl salt, tlc Rf (free base)=0.20 (10% 7 N $NH_3$ in MeOH/$CH_2Cl_2$), m/z obs=366.2 (M+1).

5-Pentylaminomethyl-3-phenylsulfanyl-1H-indole-2-carboxylic acid amide, Im,

Treat 5-formyl-3-phenylsulfanyl-1H-indole-2-carboxylic acid amide 13 (m=0, $R_3$=Ph) (50 mg, 0.169 mmol) with pentyl amine (19.6 µL, 0.338 mmol) as described in General Procedure X to afford Im (20.0 mg, 32.2%) isolated as the HCl salt, tlc Rf (free base)=0.20 (10% MeOH/$CH_2Cl_2$–0.5%$Et_3N$), m/z obs=368 (M+1).

5-Heptylaminomethyl-3-phenylsulfanyl-1H-indole-2-carboxylic acid amide, In

Treat 5-formyl-3-phenylsulfanyl-1H-indole-2-carboxylic acid amide 13 (m=0, $R_3$=Ph) (50 mg, 0.169 mmol) with heptyl amine (22.3 µL, 0.338 mmol) as described in General Procedure X to afford In (20.0 mg, 31.1%) isolated as the HCl salt, tlc Rf (free base)=0.20 (10% MeOH/$CH_2Cl_2$–0.5%$Et_3N$), m/z obs=382 (M+1).

5-(3-Carbamoylpiperidin-1-ylmethyl)-3-phenylsulfanyl-1H-indole-2-carboxylic acid amide, Io Treat 5-formyl-3-phenylsulfanyl-1H-indole-2-carboxylic acid amide 13 (m=0, $R_3$=Ph) (50 mg, 0.169 mmol) with piperidine-3-carboxamide (64.1 mg, 0.338 mmol) as described in General Procedure X to afford Io (32.0 mg, 46.4%) isolated as the HCl salt, tlc Rf (free base)=0.10 (10% MeOH/CH$_2$Cl$_2$–0.5% Et$_3$N), m/z obs=409 (M+1).

3-Phenylsulfanyl-5-(4-pyrimidin-2-yl-piperazin-1-ylmethyl)-1H-indole-2-carboxylic acid amide, Ip Treat 5-formyl-3-phenylsulfanyl-1H-indole-2-carboxylic acid amide 13 (m=0, R$_3$=Ph) (50 mg, 0.169 mmol) with 2-piperazin-1-yl-pyrimidine (101 mg, 0.5 mmol) as described in General Procedure X to afford Ip (17.0 mg, 22.6%) isolated as the HCl salt, tlc Rf (free base)=0.40 (10% MeOH/CH$_2$Cl$_2$–0.5% Et$_3$N), m/z obs=445 (M+1).

5-[4-(3-Phenylpropenyl)piperazin-1-ylmethyl]-3-phenylsulfanyl-1H-indole-2-carboxylic acid amide, Iq Treat 5-formyl-3-phenylsulfanyl-1H-indole-2-carboxylic acid amide 13 (m=0, R$_3$=Ph) (50 mg, 0.169 mmol) with 1-(3-phenyl-propenyl)piperazine (118.6 mg, 0.5 mmol) as described in General Procedure X to afford Iq (16.0 mg, 19.7%) isolated as the HCl salt, tlc Rf (free base)=0.35 (10% MeOH/CH$_2$Cl$_2$–0.25% Et$_3$N), m/z obs=483 (M+1).

4-(2-Carbamoyl-3-phenylsulfanyl-1H-indol-5-ylmethyl)-[1,4]diazepane-1-carboxylic acid tert-butyl ester, Ir Treat 5-formyl-3-phenylsulfanyl-1H-indole-2-carboxylic acid amide 13 (m=0, R$_3$=Ph) (100 mg, 0.338 mmol) with Boc-1,4-diazepine (93 mg, 0.5 mmol) as described in General Procedure X to afford Ir (96 mg, 59.3%), tlc Rf (free base)=0.45 (10% MeOH/CH$_2$Cl$_2$–0.25% Et$_3$N), m/z obs=481 (M+1).

5-[1,4]Diazepan-1-ylmethyl-3-phenylsulfanyl-1H-indole-2-carboxylic acid amide, Is Treat the Boc-protected indole Ir (62 mg, 0.129 mmol) with TFA (2.0 mL) at rt for 10 min. to afford Is (53 mg) as the TFA salt, m/z obs=381 (M+1).

5-(Bicyclo[2.2.1]hept-2-ylaminomethyl-3-phenylsulfanyl-1H-indole-2-carboxylic acid amide, It Treat 5-formyl-3-phenylsulfanyl-1H-indole-2-carboxylic acid amide 13 (m=0, R$_3$=Ph) (50 mg, 0.169 mmol) with 2-aminonorbornane hydrochloride (18.8 mg, 0.169 mmol) as described in General Procedure X to afford It (27 mg, 40.9%) isolated as the HCl salt, tlc Rf (free base)=0.8 (10% MeOH/CH$_2$Cl$_2$–0.25% Et$_3$N), m/z obs=392 (M+1), 414 (M+Na).

3-Phenylsulfanyl-5-(quinolin-6-ylaminomethyl)-1H-indole-2-carboxylic acid amide, Iu Treat 5-formyl-3-phenylsulfanyl-1H-indole-2-carboxylic acid amide 13 (m=0, R$_3$=Ph) (50 mg, 0.169 mmol) with 6-aminoquinoline (24.4 mg, 0.169 mmol) as described in General Procedure X to afford Iu (6.0 mg, 8.4%) isolated as the HCl salt, tlc Rf (free base)=0.5 (10% MeOH/CH$_2$Cl$_2$–0.25% Et$_3$N), m/z obs=425 (M+1).

5-[(2-Hydroxy-1-hydroxymethyl-1-methyl-ethylamino)methyl]-3-phenylsulfanyl-1H-indole-2-carboxylic acid amide, Iv Treat 5-formyl-3-phenylsulfanyl-1H-indole-2-carboxylic acid amide 13 (m=0, R$_3$=Ph) (50 mg, 0.169 mmol) with 2-amino-2-methyl-1,3-propanediol (50 mg, 0.47 mmol) as described in General Procedure X to afford Iv (21.0 mg, 32.3%) as a tan solid, tlc Rf=0.15 (10% MeOH/CH$_2$Cl$_2$–0.25% Et$_3$N), m/z obs=386 (M+1).

5-(2-Hydroxymethyl-pyrrolidin-1-ylmethyl)-3-phenylsulfanyl-1H-indole-2-carboxylic acid amide, Iw Treat 5-formyl-3-phenylsulfanyl-1H-indole-2-carboxylic acid amide 13 (m=0, R$_3$=Ph) (50 mg, 0.169 mmol) with 2-hydroxymethylpyrrolidine (46 mg, 0.45 mmol) as described in General Procedure X to afford Iw (42.0 mg, 65.6%) as a tan solid, tlc Rf=0.15 (10% MeOH/CH$_2$Cl$_2$–0.25% Et$_3$N), m/z obs=382 (M+1).

5-[(2-Hydroxy-1-methyl-ethylamino)methyl]-3-phenylsulfanyl-1H-indole-2-carboxylic acid amide, Ix Treat 5-formyl-3-phenylsulfanyl-1H-indole-2-carboxylic acid amide 13 (m=0, R$_3$=Ph) (80 mg, 0.27 mmol) with 2-amino-2-propanol (22.3 mg, 0.297 mmol) as described in General Procedure X to afford Ix (31.0 mg, 32.3%) as a ivory colored solid, mp=192.7-193.6° C., tlc Rf=0.10 (10% MeOH/CH$_2$Cl$_2$–0.20% Et$_3$N), m/z obs=356 (M+1).

5-[(2,3-Dihydroxypropylamino)methyl]-3-phenylsulfanyl-1H-indole-2-carboxylic acid amide, Iy Treat 5-formyl-3-phenylsulfanyl-1H-indole-2-carboxylic acid amide 13 (m=0, R$_3$=Ph) (80 mg, 0.27 mmol) with 1-amino-2,3-propylenediol (27.1 mg, 0.297 mmol) as described in General Procedure X to afford Iy (31.0 mg, 32.3%) as colorless needles, tlc Rf=0.30 (50% MeOH/CH$_2$Cl$_2$–0.20% Et$_3$N), m/z obs=372 (M+1), 394 (M+Na).

5-(1,4-Dioxa-8-aza-spiro[4,5]dec-8-ylmethyl)-3-phenylsulfanyl-1H-indole-2 carboxylic acid amide, Iz Treat 5-formyl-3-phenylsulfanyl-1H-indole-2-carboxylic acid amide 13 (m=0, R$_3$=Ph) (80 mg, 0.27 mmol) with 1,4-dioxa-8-aza-spiro[4,5]decane (71.6 mg, 0.50 mmol) as described in General Procedure X to afford Iz (51.0 mg, 44.7%) as a tan solid, tlc Rf=0.35 (10% MeOH/CH$_2$Cl$_2$–0.20% Et$_3$N), m/z obs=424 (M+1).

5-[4-(4-Fluorophenyl)piperazin-1-ylmethyl]-3-phenylsulfanyl-1H-indole-2-carboxylic acid amide, Iaa Treat 5-formyl-3-phenylsulfanyl-1H-indole-2-carboxylic acid amide 13 (m=0, R$_3$=Ph) (80 mg, 0.27 mmol) with 1-(4-fluorophenyl)piperazine (90 mg, 0.50 mmol) as described in General Procedure X to afford Iaa (69.0 mg, 55.6%) as an ivory colored solid, tlc Rf=0.4 (10% MeOH/CH$_2$Cl$_2$–0.20% Et$_3$N), m/z obs=461 (M+1).

5-[(2-Cyano-4,5-dimethoxyphenylamino)methyl]-3-phenylsulfanyl-1H-indole-2-carboxylic acid amide, Iab Treat 5-formyl-3-phenylsulfanyl-1H-indole-2-carboxylic acid amide 13 (m=0, R$_3$=Ph) (50 mg, 0.17 mmol) with 2-amino-4,5-dimethoxybenzonitrile (89 mg, 0.50 mmol) as described in the General Procedure X to afford Iab (28 mg, 36.4%) as an ivory colored solid, tlc Rf=0.1 (2% 7 N NH$_3$-MeOH/CH$_2$Cl$_2$), m/z obs=481 (M+Na).

3-Phenylsulfanyl-5-[(3-trifluoromethyl-phenylamino)methyl]-1H-indole-2-carboxylic acid amide, Iac Treat 5-formyl-3-phenylsulfanyl-1H-indole-2-carboxylic acid amide 13 (m=0, $R_3$=Ph) (50 mg, 0.17 mmol) with 3-trifluoromethylaniline (80 mg, 0.50 mmol) as described in General Procedure X to afford Iac (36 mg, 48.3%) as an ivory colored solid, tlc Rf=0.5 (5% MeOH/$CH_2Cl_2$), m/z obs=442 (M+1).

5-Ethylaminomethyl-3-phenylsulfanyl-1H-indole-2-carboxylic acid amide, Iad

Treat 5-formyl-3-phenylsulfanyl-1H-indole-2-carboxylic acid amide 13 (m=0, $R_3$=Ph) (80 mg, 0.27 mmol) with ethylamine hydrochloride (23.9 mg, 0.30 mmol) as described in General Procedure X to afford Iad (53.0 mg, 60.4%) as an ivory colored solid, tlc Rf=0.1 (10% MeOH/$CH_2Cl_2$–0.2% $Et_3N$), m/z obs=326 (M+1).

3-Phenylsulfanyl-5-propylaminomethyl-1H-indole-2-carboxylic acid amide, Iae

Treat 5-formyl-3-phenylsulfanyl-1H-indole-2-carboxylic acid amide 13 (m=0, $R_3$=Ph) (80 mg, 0.27 mmol) with propylamine hydrochloride (28 mg, 0.30 mmol) as described in General Procedure X to afford Iae (41.0 mg, 44.8%) as an ivory colored solid, tlc Rf=0.1 (10% MeOH/$CH_2Cl_2$–0.2% $Et_3N$), m/z obs=340 (M+1).

5-[(1-Carbamoylethylamino)methyl]-3-phenylsulfanyl-1H-indole-2-carboxylic acid amide, Iaf Treat 5-formyl-3-phenylsulfanyl-1H-indole-2-carboxylic acid amide 13 (m=0, $R_3$=Ph) (50 mg, 0.17 mmol) with 2-aminopropionamide (62.3 mg, 0.50 mmol) as described in General Procedure X to afford Iaf (39 mg, 62.9%) as an ivory colored solid, tlc Rf=0.5 (10% MeOH/$CH_2Cl_2$–0.2% $Et_3N$), m/z obs=369 (M+1).

5-[(3-Methoxyphenylamino)methyl]-3-phenylsulfanyl-1H-indole-2-carboxylic acid amide, Iag Treat 5-formyl-3-phenylsulfanyl-1H-indole-2-carboxylic acid amide 13 (m=0, $R_3$=Ph) (50 mg, 0.17 mmol) with 3-methoxyaniline (61.6 mg, 0.50 mmol) as described in General Procedure X to afford Iag (26 mg, 37.7%) as an ivory colored solid, tlc Rf=0.6 (5% MeOH/$CH_2Cl_2$–0.2% $Et_3N$), m/z obs=404 (M+1).

5-[(4-Butylphenylamino)methyl]-3-phenylsulfanyl-1H-indole-2-carboxylic acid amide, Iah Treat 5-formyl-3-phenylsulfanyl-1H-indole-2-carboxylic acid amide 13 (m=0, $R_3$=Ph) (50 mg, 0.17 mmol) with 4-butylaniline (74 mg, 0.50 mmol) as described in General Procedure X to afford Iah (17 mg, 23.4%) as an ivory colored solid, tlc Rf=0.8 (5% MeOH/$CH_2Cl_2$–0.2% $Et_3N$), m/z obs=430 (M+1).

5-[(2-Fluorophenylamino)methyl]-3-phenylsulfanyl-1H-indole-2-carboxylic acid amide, Iai Treat 5-formyl-3-phenylsulfanyl-1H-indole-2-carboxylic acid amide 13 (m=0, $R_3$=Ph) (50 mg, 0.17 mmol) with 2-fluoroaniline (55 mg, 0.50 mmol) as described in General Procedure X to afford Iai (12 mg, 18.2%) as an ivory colored solid, tlc Rf=0.8 (5% MeOH/$CH_2Cl_2$–0.2% $Et_3N$), m/z obs=392 (M+1).

5-(Isopropylaminomethyl)-3-phenylsulfanyl-1H-indole-2-carboxylic acid amide, Iaj Treat 5-formyl-3-phenylsulfanyl-1H-indole-2-carboxylic acid amide 13 (m=0, $R_3$=Ph) (80 mg, 0.27 mmol) with isopropylamine (19.2 mg, 0.32 mmol) as described in General Procedure X to afford Iaj (17 mg, 18.6%) as an ivory colored solid, tlc Rf=0.3 (10% 7 N $NH_3$-MeOH/$CH_2Cl_2$), m/z obs=362 (M+Na).

TABLE 1

Compounds of Formula I

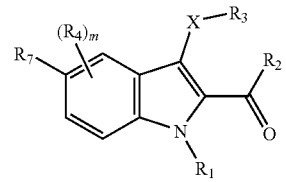

wherein m is 0, $R_2$ is $NH_2$, $R_7$ is $CH_2NR_8R_9$ and X is S.

| Example No. | $R_1$ | $R_3$ | $NR_8R_9$ |
|---|---|---|---|
| Ia | H | $C_6H_5$ | $NH_2$ |
| Ib | H | $C_6H_5$ | Boc-NH |
| Ic | H | $C_6H_5$ | $CH_3NH$ |
| Id | H | 3-F—$C_6H_4$ | $CH_3NH$ |
| Ie | H | 3-Cl—$C_6H_4$ | $CH_3NH$ |
| If | H | $C_6H_5$ | $C_6H_5CH_2NH$ |
| Ig | $CH_3$ | $C_6H_5$ | $CH_3NH$ |
| Ih | H | $C_6H_5$ | ![HOH2C-piperidine] |
| Ii | H | $C_6H_5$ | ![morpholine] |
| Ij | H | $C_6H_5$ | $CH_3(CH_2)_2NH$ |
| Ik | H | $C_6H_5$ | $CH_3(CH_2)_3NH$ |
| Il | H | $C_6H_5$ | ![piperidine] |
| Im | H | $C_6H_5$ | $CH_3(CH_2)_4NH$ |
| In | H | $C_6H_5$ | $CH_3(CH_2)_6NH$ |
| Io | H | $C_6H_5$ | ![H2N-C(O)-piperidine] |
| Ip | H | $C_6H_5$ | ![pyrimidinyl-piperazine] |
| Iq | H | $C_6H_5$ | $C_6H_5CH_2CH=CH$—![piperazine] |

TABLE 1-continued

Compounds of Formula I

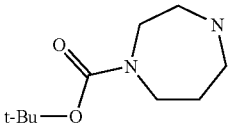

wherein m is 0, $R_2$ is $NH_2$, $R_7$ is $CH_2NR_8R_9$ and X is S.

| Example No. | $R_1$ | $R_3$ | $NR_8R_9$ |
|---|---|---|---|
| Ir | H | $C_6H_5$ | 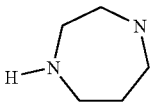 |
| Is | H | $C_6H_5$ | 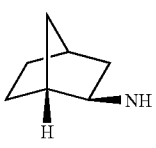 |
| It | H | $C_6H_5$ | 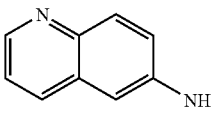 |
| Iu | H | $C_6H_5$ | 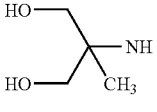 |
| Iv | H | $C_6H_5$ | 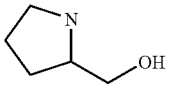 |
| Iw | H | $C_6H_5$ | 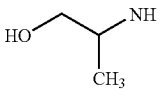 |
| Ix | H | $C_6H_5$ | 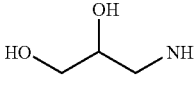 |
| Iy | H | $C_6H_5$ | 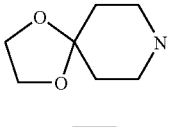 |
| Iz | H | $C_6H_5$ | 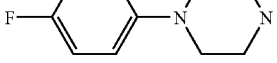 |
| Iaa | H | $C_6H_5$ | 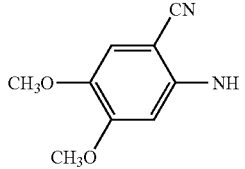 |

TABLE 1-continued

Compounds of Formula I

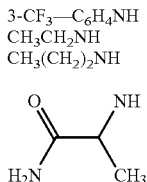

wherein m is 0, $R_2$ is $NH_2$, $R_7$ is $CH_2NR_8R_9$ and X is S.

| Example No. | $R_1$ | $R_3$ | $NR_8R_9$ |
|---|---|---|---|
| Iab | H | $C_6H_5$ | 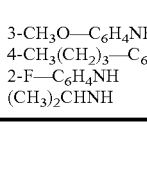 |
| Iac | H | $C_6H_5$ | 3-$CF_3$—$C_6H_4NH$ |
| Iad | H | $C_6H_5$ | $CH_3CH_2NH$ |
| Iae | H | $C_6H_5$ | $CH_3(CH_2)_2NH$ |
| Iaf | H | $C_6H_5$ | 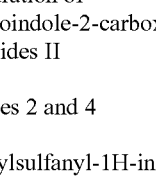 |
| Iag | H | $C_6H_5$ | 3-$CH_3O$—$C_6H_4NH$ |
| Iah | H | $C_6H_5$ | 4-$CH_3(CH_2)_3$—$C_6H_4NH$ |
| Iai | H | $C_6H_5$ | 2-F—$C_6H_4NH$ |
| Iaj | H | $C_6H_5$ | $(CH_3)_2CHNH$ |

Preparation of
6-substituted-3-arylthioindole-2-carboxylic acid
amides II

Schemes 2 and 4

6-Aminomethyl-3-phenylsulfanyl-1H-indole-2-carboxylic acid amide, IIa and (2-Carbamoyl-3-phenylsulfanyl-1H-indol-6-ylmethyl)-carbamic acid tert-butyl ester, IIb Title compounds IIa and IIb are prepared as is described above for the synthesis of compounds 11a and 11b according to scheme 2.

6-(Benzylaminomethyl)-3-phenylsulfanyl-1H-indole-2-carboxylic acid amide, IIc

Treat indole 11b (scheme 4, m=0, $R_3$=Ph) (100 mg, 0.24 mmol) with benzaldehyde (0.8 equiv, 20.4 mg, 0.198 mmol) as described in procedure IX to afford IIc (80 mg, 56.3%) as the TFA salt, tlc of the free base (12% MeOH/$CH_2Cl_2$–1.0% $NH_3$) Rf=0.40, m/z obs=388 (M+1).

6-[(4-Nitrobenzylamino)methyl]-3-phenylsulfanyl-1H-indole-2-carboxylic acid amide, IId Treat 11b (scheme 4, m=0, $R_3$=Ph) (175 mg, 0.42 mmol) with 4-nitrobenzaldehyde (0.8 equiv, 50.8 mg, 0.336 mmol) as described in procedure IX to afford IId ((79 mg, 28.7%)

6-[(4-Dimethylaminobenzylamino)methyl]-3-phenylsulfanyl-1H-indole-2-carboxylic acid amide, IIe Treat 11b (scheme 4, m=0, $R_3$=Ph) (75 mg, 0.18 mmol) with 4-dimethylamino-benzaldehyde (0.8 equiv, 21.5 mg, 0.144 mmol) as described in procedure IX to afford IIe (35 mg, 27.6%) isolated as the HCl salt, tlc of the free base (12% MeOH/$CH_2Cl_2$–1.0% $NH_3$) Rf=0.45, m/z obs=431 (M+1).

6-[(4-Methylbenzylamino)methyl]-3-phenylsulfanyl-1H-indole-2-carboxylic acid amide, IIf Treat 11b (scheme 4, m=0, $R_3$=Ph) (100 mg, 0.24 mmol) with tolualdehyde (0.8 equiv, 23.8 mg, 0.192 mmol) as described in procedure IX to afford IIf (44 mg, 29.9%) isolated as the HCl salt, tlc of the free base (10% MeOH/$CH_2Cl_2$–1.0% $NH_3$) Rf=0.40, m/z obs=402 (M+1).

6-[(4-Methoxybenzylamino)methyl]-3-phenylsulfanyl-1H-indole-2-carboxylic acid amide, IIg Treat 11b (scheme 4, m=0, $R_3$=Ph) (100 mg, 0.24 mmol) with p-anisaldehyde (0.8 equiv, 26.7 mg, 0.192 mmol) as described in procedure IX to afford IIg (42 mg, 27.5%) isolated as the HCl salt, m/z obs=418 (M+1).

6-[(4-Bromobenzylamino)methyl]-3-phenylsulfanyl-1H-indole-2-carboxylic acid amide, IIh Treat 11b (scheme 4, m=0, $R_3$=Ph) (100 mg, 0.24 mmol) with 4-bromobenzaldehyde (0.8 equiv, 35.9 mg, 0.192 mmol) as described in procedure IX to afford IIh (54 mg, 34.5%) isolated as the HCl salt as a yellow powder, tlc of the free base (10% MeOH/$CH_2Cl_2$–0.25% $NH_3$) Rf=0.50, m/z obs=466 (M+1).

6-[(4-Chlorobenzylamino)methyl]-3-phenylsulfanyl-1H-indole-2-carboxylic acid amide, IIi Treat 11b (scheme 4, m=0, $R_3$=Ph) (110 mg, 0.266 mmol) with 4-chlorobenzaldehyde (0.8 equiv, 30.4 mg, 0.213 mmol) as described in procedure IX to afford IIi (47 mg, 27.7%) isolated as the HCl salt, tlc of the free base (10% MeOH/$CH_2Cl_2$–0.25% $NH_3$) Rf=0.60, m/z obs=422 (M+1).

6-{[(Biphenyl-4-ylmethyl)amino]methyl}-3-phenylsulfanyl-1H-indole-2-carboxylic acid amide, IIj Treat 11b (scheme 4, m=0, $R_3$=Ph) (110 mg, 0.266 mmol) with 4-phenylbenzaldehyde (0.8 equiv, 39.2 mg, 0.213 mmol) as described in procedure IX to afford IIj (40 mg, 21.6%) isolated as the HCl salt, tlc of the free base (5% MeOH/$CH_2Cl_2$–0.25% $NH_3$) Rf=0.20, m/z obs=464 (M+1).

6-[(3-Nitrobenzylamino)methyl]-3-phenylsulfanyl-1H-indole-2-carboxylic acid amide, IIk Treat 11b (scheme 4, m=0, $R_3$=Ph) (110 mg, 0.266 mmol) with 3-nitrobenzaldehyde (0.8 equiv, 32.5 mg, 0.213 mmol) as described in procedure IX to afford IIk (48 mg, 27.7%) isolated as the HCl salt, tlc of the free base (10% MeOH/$CH_2Cl_2$–0.25% $NH_3$) Rf=0.55, m/z obs=433 (M+1).

6-[(2-Nitrobenzylamino)methyl]-3-phenylsulfanyl-1H-indole-2-carboxylic acid amide, IIl Treat 11b (scheme 4, m=0, $R_3$=Ph) (110 mg, 0.266 mmol) with 2-nitrobenzaldehyde (0.8 equiv, 32.5 mg, 0.213 mmol) as described in procedure IX to afford IIl (36 mg, 20.8%) as the HCl salt, tlc of the free base (10% MeOH/$CH_2Cl_2$–0.25% $NH_3$) Rf=0.55, m/z obs=433 (M+1).

3-Phenylsulfanyl-6-[(4-trifluoromethylbenzylamino)methyl]-1H-indole-2-carboxylic acid amide, IIm Treat 11b (scheme 4, m=0, $R_3$=Ph) (110 mg, 0.266 mmol) with 4-trifluoromethyl-benzaldehyde (0.8 equiv, 37.8 mg, 0.213 mmol) as described in procedure IX to afford IIm (50 mg, 27.5%) isolated as the HCl salt, tlc of the free base (10% MeOH/$CH_2Cl_2$–0.25% $NH_3$) Rf=0.40, m/z obs=456 (M+1).

6-[(3-Fluoro-5-trifluoromethylbenzylamino)methyl]-3-phenylsulfanyl-1H-indole-2-carboxylic acid amide, IIn Treat 11b (scheme 4, m=0, $R_3$=Ph) (110 mg, 0.266 mmol) with 3-fluoro-5-trifluoromethylbenzaldehyde (0.8 equiv, 42.2 mg, 0.213 mmol) as described in procedure IX to afford IIn (38 mg, 20.2%) isolated as the HCl salt, tlc of the free base (10% MeOH/$CH_2Cl_2$–0.25% $NH_3$) Rf=0.25, m/z obs=474 (M+1).

6-[(2-Aminopropionylamino)methyl]-3-phenylsulfanyl-1H-indole-2-carboxylic acid amide, IIo Treat 11b (scheme 4, m=0, $R_3$=Ph) (100 mg, 0.24 mmol) with Boc-Ala-OSu (1.10 equiv, 76.2 mg, 0.266 mmol) as described in procedure XV to afford the Boc protected product and then treat with TFA (5.0 mL, 99%) to provide IIo (78 mg, 48.2%) as the TFA salt, m/z obs=369 (M+1), 391 (M+Na).

6-[(2-Aminoacetylamino)methyl]-3-phenylsulfanyl-1H-indole-2-carboxylic acid amide, IIp Treat 11b (scheme 4, m=0, $R_3$=Ph) (60 mg, 0.145 mmol) with Boc-Gly-OSu (1.10 equiv, 43.5 mg, 0.16 mmol) as described in procedure XV to afford the Boc protected product and then treat with TFA (5.0 mL, 99%) to provide IIp (56 mg, 82.3%) as the TFA salt, tlc of the free base (10% MeOH/$CH_2Cl_2$–0.25% $NH_3$) Rf=0.20, m/z obs=355 (M+1).

6-[(2-Amino-3-methylpentanoylamino)methyl]-3-phenylsulfanyl-1H-indole-2-carboxylic acid amide, IIq Treat 11b (scheme 4, m=0, $R_3$=Ph) (60 mg, 0.145 mmol) with Boc-Ile-OSu (1.10 equiv, 52.5 mg, 0.16 mmol) as described in procedure VIII to afford the Boc protected product and then treat with TFA (5.0 mL, 99%) to provide IIq (41 mg, 53.9%) as the TFA salt, tlc of the free base (10% MeOH/$CH_2Cl_2$–0.25% $NH_3$) Rf=0.25, m/z obs=411 (M+1).

2-Aminopentanedioic acid 5-amide 1-[(2-carbamoyl-3-phenylsulfanyl-1H-indol-6-ylmethyl)-amide], IIr Treat 11b (scheme 4, m=0, $R_3$=Ph) (60 mg, 0.145 mmol) with Boc-Gln-OSu (1.10 equiv, 54.9 mg, 0.16 mmol) as described in procedure XV to afford the Boc protected product and then treat with TFA (5.0 mL, 99%) to provide IIr (42 mg, 53.8%) as the TFA salt, m/z obs=426 (M+1).

6-{[(2-Amino-3-(1H-indol-3-yl)propionylamino]methyl}-3-phenylsulfanyl-1H-indole-2-carboxylic acid amide, IIs Treat 11b (scheme 4, m=0, $R_3$=Ph) (60 mg, 0.145 mmol) with Boc-Trp-OSu (1.10 equiv, 64.2 mg, 0.16 mmol) as described in procedure VIII to afford the Boc protected product and then treat with TFA (5.0 mL, 99%) to provide IIs (64 mg, 73.8%) as the TFA salt, tlc of the free base (10% MeOH/CH$_2$Cl$_2$–0.25% NH$_3$) Rf=0.15, m/z obs=484 (M+1).

6-[(2-Amino-3-phenylpropionylamino)methyl]-3-phenylsulfanyl-1H-indole-2-carboxylic acid amide, IIt Treat 11b (scheme 4, m=0, $R_3$=Ph) (60 mg, 0.145 mmol) with Boc-Phe-OSu (1.10 equiv, 58 mg, 0.16 mmol) as described in procedure XV to afford the Boc protected product and then treat with TFA (5.0 mL, 99%) to provide IIt (59 mg, 72.8%) as the TFA salt, tlc of the free base (10% MeOH/CH$_2$Cl$_2$–0.25% NH$_3$) Rf=0.20, m/z obs=445 (M+1).

6-[(2-Amino-4-methylsulfanylbutyrylamino)methyl]-3-phenylsulfanyl-1H-indole-2-carboxylic acid amide, IIu Treat 11b (scheme 4, m=0, $R_3$=Ph) (60 mg, 0.145 mmol) with Boc-Met-OSu (1.10 equiv, 55.4 mg, 0.16 mmol) as described in procedure XV to afford the Boc protected product and then treat with TFA (5.0 mL, 99%) to provide IIu (58 mg, 73.7%) as the TFA salt, tlc of the free base (10% MeOH/CH$_2$Cl$_2$–0.25% NH$_3$) Rf=0.55, m/z obs=429 (M+1).

6-{[(2-Methoxynaphthalen-1-ylmethyl)amino]-methyl]}-3-phenylsulfanyl-1H-indole-2-carboxylic acid amide, IIv Treat 11b (scheme 4, m=0, $R_3$=Ph) (110 mg, 0.266 mmol) with 2-methoxy-1-naphtaldehyde (0.8 equiv, 40.0 mg, 0.213 mmol) as described in procedure IX to afford IIv (48 mg, 35.8%) isolated as the HCl salt, tlc of the free base (15% MeOH/CH$_2$Cl$_2$–0.25% NH$_3$) Rf=0.15, m/z obs=468 (M+1).

6-[(2,4-Dimethoxybenzylamino)methyl]-3-phenylsulfanyl-1H-indole-2-carboxylic acid amide, IIw Treat 11b (scheme 4, m=0, $R_3$=Ph) (110 mg, 0.266 mmol) with 2,4-dimethoxy-benzaldehyde (0.8 equiv, 36.1 mg, 0.213 mmol) as described in procedure IX to afford IIw (58 mg, 45%) isolated as the HCl salt, tlc of the free base (15% MeOH/CH$_2$Cl$_2$–0.25% NH$_3$) Rf=0.15, m/z obs=448 (M+1).

6-[(3-Phenoxybenzylamino)methyl]-3-phenylsulfanyl-1H-indole-2-carboxylic acid amide, IIx Treat 11b (scheme 4, m=0, $R_3$=Ph) (110 mg, 0.266 mmol) with 3-phenoxy-benzaldehyde (0.8 equiv, 44.4 mg, 0.213 mmol) as described in procedure IX to afford IIx (46 mg, 33.6%) isolated as the HCl salt, tlc of the free base (10% MeOH/CH$_2$Cl$_2$–0.25% NH$_3$) Rf=0.4, m/z obs=480 (M+1).

6-[(3-Methoxybenzylamino)methyl]-3-phenylsulfanyl-1H-indole-2-carboxylic acid amide, IIy Treat 11b (scheme 4, m=0, $R_3$=Ph) (110 mg, 0.266 mmol) with 3-methoxybenzaldehyde (0.8 equiv, 29.9 mg, 0.213 mmol) as described in procedure IX to afford IIy (42 mg, 34.8%) isolated as the HCl salt, tlc of the free base (10% MeOH/CH$_2$Cl$_2$–0.25% NH$_3$) Rf=0.25, m/z obs=418 (M+1).

6-[(2-Methylbenzylamino)methyl]-3-phenylsulfanyl-1H-indole-2-carboxylic acid amide, IIz Treat 11b (scheme 4, m=0, $R_3$=Ph) (110 mg, 0.266 mmol) with 2-methyl-benzaldehyde (0.8 equiv, 27.7 mg, 0.213 mmol) as described in procedure IX to afford IIz (32 mg, 27.6%) isolated as the HCl salt, tlc of the free base (10% MeOH/CH$_2$Cl$_2$–0.25% NH$_3$) Rf=0.35, m/z obs=402 (M+1).

6-[(3-Methylbenzylamino)methyl]-3-phenylsulfanyl-1H-indole-2-carboxylic acid amide, IIaa Treat 11b (scheme 4, m=0, $R_3$=Ph) (110 mg, 0.266 mmol) with 3-methyl-benzaldehyde (0.8 equiv, 27.7 mg, 0.213 mmol) as described in procedure IX to afford IIaa (53 mg, 45.7%) isolated as the HCl salt, tlc of the free base (10% MeOH/CH$_2$Cl$_2$–0.25% NH$_3$) Rf=0.4, m/z obs=402 (M+1).

6-[(2-Fluoro-3-trifluoromethylbenzylamino)methyl]-3-phenylsulfanyl-1H-indole-2-carboxylic acid amide, IIab Treat 11b (scheme 4, m=0, $R_3$=Ph) (100 mg, 0.24 mmol) with 2-fluoro-3-trifluoromethylbenzaldehyde (1.0 equiv, 48.5 mg, 0.24 mmol) as described in procedure IX to afford IIab (74 mg, 60.2%) isolated as the HCl salt, tlc of the free base (2% MeOH/CH$_2$Cl$_2$–0.25% NH$_3$) Rf=0.3, m/z obs=474 (M+1).

6-[(2-Methoxybenzylamino)methyl]-3-phenylsulfanyl-1H-indole-2-carboxylic acid amide, IIac Treat 11b (scheme 4, m=0, $R_3$=Ph) (100 mg, 0.24 mmol) with 2-methoxy-benzaldehyde (1.0 equiv, 33.4 mg, 0.24 mmol) as described in procedure IX to afford IIac (48 mg, 43.8%) isolated as the HCl salt, tlc of the free base (10% MeOH/CH$_2$Cl$_2$–0.25% NH$_3$) Rf=0.40, m/z obs=418 (M+1).

6-[(2,6-Diaminohexanoylamino)methyl]-3-phenylsulfanyl-1H-indole-2-carboxylic acid amide, IIad Treat 11b (scheme 4, m=0, $R_3$=Ph) (100 mg, 0.242 mmol) with Boc-Lys(Boc)-OSu (that is, the doubly N-Boc-protected lysine N-hydroxysuccinimide ester) (1.10 equiv, 118 mg, 0.266 mmol) as described in procedure XV to afford the Boc protected product and then treat with TFA (5.0 mL, 99%) to provide IIad (72 mg, 45.6%) as the TFA salt, tlc of the free base (10% MeOH/CH$_2$Cl$_2$–0.25% NH$_3$) Rf=0.35, m/z obs=426 (M+1).

3-Amino-N-(2-carbamoyl-3-phenylsulfanyl-1H-indol-6-ylmethyl)succinamic acid, IIae Treat 11b (scheme 4, m=0, $R_3$=Ph) (60 mg, 0.145 mmol) with Boc-Asp(OtBu)-OSu (1.10 equiv, 61.8 mg, 0.16 mmol) as described in procedure XV to afford the Boc protected product and then treat with TFA (5.0 mL, 99%) to provide IIae (52 mg, 68.1%) as the TFA salt, tlc of the free base (10% MeOH/CH$_2$Cl$_2$–0.25% NH$_3$) Rf=0.55, m/z obs=413 (M+1).

6-{[(10-Chloro-anthracen-9-ylmethyl)amino]methyl}-3-phenylsulfanyl-1H-indole-2-carboxylic acid amide, IIaf Treat 11b (scheme 4, m=0, $R_3$=Ph) (90 mg, 0.218 mmol) with 10-chloro-9-anthraldehyde (1.0 equiv, 52.5 mg, 0.218 mmol) as described in procedure IX to afford IIaf (53 mg, 43.6%) isolated as the HCl salt, tlc of the free base (10% MeOH/CH$_2$Cl$_2$–0.25% NH$_3$) Rf=0.40, m/z obs=522 (M+1).

6-{[(Bis-(3-furan-2-yl-allyl)amino]methyl}-3-phenylsulfanyl-1H-indole-2-carboxylic acid amide, IIag Treat 11b (scheme 4, m=0, R$_3$=Ph) (90 mg, 0.218 mmol) with trans-3-(2-furyl)acrolein (2.0 equiv, 53.2 mg, 0.436 mmol) as described in procedure IX to afford IIag (28 mg, 23.5%) isolated as the HCl salt, tlc of the free base (10% MeOH/CH$_2$Cl$_2$–0.25% NH$_3$) Rf=0.65, m/z obs=510 (M+1).

6-[(3,5-Dichloro-2-hydroxybenzylamino)methyl]-3-phenylsulfanyl-1H-indole-2-carboxylic acid amide, IIah Treat 11b (scheme 4, m=0, R$_3$=Ph) (90 mg, 0.218 mmol) with 2-hydroxy-3,5-dichlorobenzaldehyde (1.0 equiv, 41.6 mg, 0.218 mmol) as described in procedure IX to afford IIah (37 mg, 33.4%) isolated as the HCl salt, tlc of the free base (10% MeOH/CH$_2$Cl$_2$–0.25% NH$_3$) Rf=0.5, m/z obs=509 (M+1).

6-[(3-Bromo-4,5-dimethoxybenzylamino)methyl]-3-phenylsulfanyl-1H-indole-2-carboxylic acid amide, IIai Treat 11b (scheme 4, m=0, R$_3$=Ph) (90 mg, 0.218 mmol) with 3,4-dimethoxy-5-bromobenzaldehyde (1.0 equiv, 54 mg, 0.218 mmol) as described in procedure IX to afford IIai (63 mg, 51.4%) isolated as the HCl salt, tlc of the free base (10% MeOH/CH$_2$Cl$_2$–0.25% NH$_3$) Rf=0.5, m/z obs=526 (M+1).

6-[(4-Benzyloxy-3-methoxybenzylamino)methyl]-3-phenylsulfanyl-1H-indole-2-carboxylic acid amide, IIaj Treat 11b (scheme 4, m=0, R$_3$=Ph) (90 mg, 0.218 mmol) with 3-methoxy-4-phenoxybenzaldehyde (1.0 equiv, 53 mg, 0.218 mmol) as described in procedure IX to afford IIaj (60 mg, 49.2%) isolated as the HCl salt, tlc of the free base (10% MeOH/CH$_2$Cl$_2$–0.25% NH$_3$) Rf=0.5, m/z obs=524 (M+1).

6-[(3-Benzyloxy-4-methoxybenzylamino)methyl]-3-phenylsulfanyl-1H-indole-2-carboxylic acid amide, IIak Treat 11b (scheme 4, m=0, R$_3$=Ph) (90 mg, 0.218 mmol) with 3-benzyloxy-4-methoxybenzaldehyde (1.0 equiv, 53 mg, 0.218 mmol) as described in procedure IX to afford IIak (62 mg, 50.8%) isolated as the HCl salt, tlc of the free base (10% MeOH/CH$_2$Cl$_2$–0.25% NH$_3$) Rf=0.5, m/z obs=524 (M+1).

6-{[(5-Nitrothiophen-2-ylmethyl)amino]methyl}-3-phenylsulfanyl-1H-indole-2-carboxylic acid amide, IIal Treat 11b (scheme 4, m=0, R$_3$=Ph) (90 mg, 0.218 mmol) with 5-nitro-2-thiophenecarboxaldehyde (1.0 equiv, 34.3 mg, 0.218 mmol) as described in procedure IX to afford IIal (36 mg, 35%) isolated as the HCl salt, tlc of the free base (10% MeOH/CH$_2$Cl$_2$–0.25% NH$_3$) Rf=0.55, m/z obs=439 (M+1).

4-{[(2-Carbamoyl-3-phenylsulfanyl-1H-indol-6-ylmethyl)amino]methyl}benzoic acid methyl ester, IIam Treat 11b (scheme 4, m=0, R$_3$=Ph) (80 mg, 0.194 mmol) with methyl 4-formyl benzoate (1.0 equiv, 31.85 mg, 0.194 mmol) as described in procedure IX to afford IIam (39 mg, 41.9%) isolated as the HCl salt, tlc of the free base (10% MeOH/CH$_2$Cl$_2$–0.25% NH$_3$) Rf=0.50, m/z obs=446 (M+1).

6-{[(3,3-Diphenylallylamino)methyl]-3-phenylsulfanyl-1H-indole-2-carboxylic acid amide, IIan Treat 11b (scheme 4, m=0, R$_3$=Ph) (80 mg, 0.194 mmol) with β-phenyl-cinnamaldehyde (1.0 equiv, 40.4 mg, 0.194 mmol) as described in procedure IX to afford IIan (28 mg, 27.5%) isolated as the HCl salt, tlc of the free base (10% MeOH/CH$_2$Cl$_2$–0.25% NH$_3$) Rf=0.50, m/z obs=490 (M+1).

3-Phenylsulfanyl-6-[(4-styrylbenzylamino)methyl]-1H-indole-2-carboxylic acid amide, IIao Treat 11b (scheme 4, m=0, R$_3$=Ph) (90 mg, 0.218 mmol) with trans-4-stilbene-carboxyaldehyde (1.0 equiv, 45.4 mg, 0.218 mmol) as described in procedure IX to afford IIao (25 mg, 21.8%) isolated as the HCl salt, tlc of the free base (10% MeOH/CH$_2$Cl$_2$–0.25% NH$_3$) Rf=0.6, m/z obs=490 (M+1).

6-[(2-Fluoro-6-trifluoromethylbenzylamino)methyl]-3-phenylsulfanyl-1H-indole-2-carboxylic acid amide, IIap Treat 11b (scheme 4, m=0, R$_3$=Ph) (90 mg, 0.218 mmol) with 2-trifluoromethyl-6-fluorobenzaldehyde (1.0 equiv, 41.0 mg, 0.218 mmol) as described in procedure IX to afford IIap (22 mg, 19.8%) isolated as the HCl salt, tlc of the free base (10% MeOH/CH$_2$Cl$_2$–0.25% NH$_3$) Rf=0.6, m/z obs=474 (M+1).

6-{[3-(4-Hydroxy-3-methoxyphenyl)allylamino]methyl}-3-phenylsulfanyl-1H-indole-2-carboxylic acid amide, IIaq Treat 11b (scheme 4, m=0, R$_3$=Ph) (90 mg, 0.218 mmol) with 4-hydroxy-3-methoxycinnamaldehyde (1.0 equiv, 38.8 mg, 0.218 mmol) as described in procedure IX to afford IIaq (20 mg, 18.5%) isolated as the HCl salt, m/z obs=490 (M+1).

6-({[5-(2-Chlorophenyl)-furan-2-ylmethyl]amino}methyl)-3-phenylsulfanyl-1H-indole-2-carboxylic acid amide, IIar Treat 11b (scheme 4, m=0, R$_3$=Ph) (90 mg, 0.218 mmol) with 5-(2-chloro-phenyl)furfural (1.0 equiv, 45 mg, 0.218 mmol) as described in procedure IX to afford IIar (28 mg, 24.6%) isolated as the HCl salt, m/z obs=488 (M+1).

6-{[(1-Benzenesulfonyl-1H-pyrrol-2-ylmethyl)amino]methyl}-3-phenylsulfanyl-1H-indole-2-carboxylic acid amide, IIas Treat 11b (scheme 4, m=0, R$_3$=Ph) (90 mg, 0.218 mmol) with 1-(phenylsulfonyl)-2-pyrrolecarboxaldehyde (1.0 equiv, 51.3 mg, 0.218 mmol) as described in procedure IX to afford IIas (53 mg, 44%) isolated as the HCl salt, m/z obs=517 (M+1).

6-{[Bis-(5-nitrofuran-2-ylmethyl)amino]methyl}-3-phenylsulfanyl-1H-indole-2-carboxylic acid amide, IIat Treat 11b (scheme 4, m=0, $R_3$=Ph) (90 mg, 0.218 mmol) with 5-nitro-2-furaldehyde (2.0 equiv, 61.5 mg, 0.436 mmol) as described in procedure IX to afford IIat (22 mg, 17.3%) isolated as the HCl salt, m/z obs=548 (M+1).

6-{[(5-Nitrofuran-2-ylmethyl)amino]methyl}-3-phenylsulfanyl-1H-indole-2-carboxylic acid amide, IIau Treat 11b (scheme 4, m=0, $R_3$=Ph) (90 mg, 0.218 mmol) with 5-nitro-2-furaldehyde (1.0 equiv, 31 mg, 0.218 mmol) as described in procedure IX to afford IIau (43 mg, 43.1%) isolated as the HCl salt, tlc of the free base (10% MeOH/$CH_2Cl_2$–0.25% $NH_3$) Rf=0.5 m/z obs=423 (M+1).

TABLE 2

Compounds of Formula II wherein m is 0, $R_2$ is $NH_2$, $R_7$ is $CH_2NR_8R_9$ and X is S.

| Example No. | $R_1$ | $R_3$ | $NR_8R_9$ |
|---|---|---|---|
| IIa | H | $C_6H_5$ | $NH_2$ |
| IIb | H | $C_6H_4$ | Boc-NH |
| IIc | H | $C_6H_4$ | $C_6H_5CH_2NH$ |
| IId | H | $C_6H_5$ | 4-$O_2N$—$C_6H_4CH_2NH$ |
| IIe | H | $C_6H_5$ | 4-$(CH_2)_3N$—$C_6H_4CH_2NH$ |
| IIf | H | $C_6H_5$ | 4-$CH_3$—$C_6H_4CH_2NH$ |
| IIg | H | $C_6H_5$ | 4-$CH_3O$—$C_6H_4CH_2NH$ |
| IIh | H | $C_6H_5$ | 4-Br—$C_6H_4CH_2NH$ |
| IIi | H | $C_6H_5$ | 4-Cl—$C_6H_4CH_2NH$ |
| IIj | H | $C_6H_5$ | 4-$C_6H_5$—$C_6H_4CH_2NH$ |
| IIk | H | $C_6H_5$ | 3-$O_2N$—$C_6H_4CH_2NH$ |
| IIl | H | $C_6H_5$ | 2-$O_2N$—$C_6H_4CH_2NH$ |
| IIm | H | $C_6H_5$ | 4-$CF_3$—$C_6H_4CH_2NH$ |
| IIn | H | $C_6H_5$ | 3-F-5-$CF_3$—$C_6H_4CH_2NH$ |
| IIo | H | $C_6H_5$ | $CH_3CH(NH_2)C(=O)NH$ |
| IIp | H | $C_6H_5$ | $H_2NCH_2C(=O)NH$ |
| IIq | H | $C_6H_5$ | (leucinamide structure) |
| IIr | H | $C_6H_5$ | (glutaminamide structure) |
| IIs | H | $C_6H_5$ | (tryptophanamide structure) |
| IIt | H | $C_6H_5$ | (phenylalaninamide structure) |
| IIu | H | $C_6H_5$ | (methioninamide structure) |
| IIv | H | $C_6H_5$ | (2-methoxynaphthalen-1-ylmethyl)NH |
| IIw | H | $C_6H_5$ | 2,4-$(CH_3O)_2$—$C_6H_3CH_2NH$ |
| IIx | H | $C_6H_5$ | 3-$C_6H_5O$—$C_6H_4CH_2NH$ |
| IIy | H | $C_6H_5$ | 3-$CH_3O$—$C_6H_4CH_2NH$ |
| IIz | H | $C_6H_5$ | 2-$CH_3$—$C_6H_4CH_2NH$ |
| IIaa | H | $C_6H_5$ | 3-$CH_3$—$C_6H_4CH_2NH$ |
| IIab | H | $C_6H_5$ | 2-F-3-$CF_3$—$C_6H_4CH_2NH$ |
| IIac | H | $C_6H_5$ | 2-$CH_3O$—$C_6H_4CH_2NH$ |
| IIad | H | $C_6H_5$ | (lysinamide structure) |
| IIae | H | $C_6H_5$ | (aspartamide structure) |
| IIaf | H | $C_6H_5$ | (10-chloroanthracen-9-ylmethyl)NH |

TABLE 2-continued

Compounds of Formula II

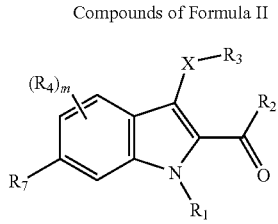

wherein m is 0, R₂ is NH₂, R₇ is CH₂NR₈R₉ and X is S.

| Example No. | R₁ | R₃ | NR₈R₉ |
|---|---|---|---|
| IIag | H | C₆H₅ | (bis-furanyl-propenyl-amine structure) |
| IIah | H | C₆H₅ | 3,5-(Cl)₂-2-OH—C₆H₄CH₂NH |
| IIai | H | C₆H₅ | 3-Br-4,5-(CH₃O)₂-C₆H₄CH₂NH |
| IIaj | H | C₆H₅ | 4-C₆H₅CH₂O-3-CH₃—C₆H₄CH₂NH |
| IIak | H | C₆H₅ | 3-C₆H₅CH₂O-4-CH₃—C₆H₄CH₂NH |
| IIal | H | C₆H₅ | O₂N-thienyl-CH₂NH |
| IIam | H | C₆H₅ | CH₃O₂C—C₆H₄—CH₂NH |
| IIan | H | C₆H₅ | (C₆H₅)₂C=CCH₂NH |
| IIao | H | C₆H₅ | stilbenyl-CH₂NH |
| IIap | H | C₆H₅ | 2-F-6-CF₃—C₆H₄CH₂NH |
| IIaq | H | C₆H₅ | 3-CH₃O-4-HO-C₆H₃-CH=CH-CH₂NH |
| IIar | H | C₆H₅ | 2-Cl-C₆H₄-furanyl-CH₂NH |
| IIas | H | C₆H₅ | (N-phenylsulfonyl-pyrrolyl)-CH₂NH |

TABLE 2-continued

Compounds of Formula II

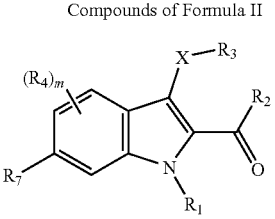

wherein m is 0, R₂ is NH₂, R₇ is CH₂NR₈R₉ and X is S.

| Example No. | R₁ | R₃ | NR₈R₉ |
|---|---|---|---|
| IIat | H | C₆H₅ | (O₂N-furanyl-CH₂)₂N |
| IIau | H | C₆H₅ | O₂N-furanyl-CH₂NH |

Biological Examples

Casein Kinase Epsilon ³³P-ATP Filter Plate Assay for Screening CK1ε Inhibitors

Purpose: This assay measures the ability of compounds to inhibit the phosphorylation of the substrate casein by the enzyme casein kinase 1ε using an in vitro $^{33}$P-ATP filtration assay. Compounds are tested at five concentrations in duplicate in order to generate IC$_{50}$ values or % inhibition at a 10 micromolar concentration that are summarized in Table 3.

Materials:
Equipment:
Beckman Biomek 2000 Liquid Handling Robot
Beckman Multimek 96 Automated 96 Channel Pipettor
Millipore Vacuum Manifold Basic Kit # MAVM0960R
Titertek Multidrop Liquid Dispenser
Packard TopCount NXT Liquid Scintillation Counter
Plates:
Costar EIA/RIA Plate #9018
Falcon 96 well U bottom Polystyrene Plate #353910
Millipore Multiscreen 96 well Filtration Plates #MAPH-NOB50
Millipore Multiscreen TopCount Adapter Plates #SE3M203V6
Chemicals:
EGTA from SIGMA #E-3889
Casein (dephosphorylated) from SIGMA #C-4032
ATP from SIGMA #A-7699
DTT from Fisher Biotech #BP1725
Trichloroacetic Acid from SIGMA #T-6399
γ-$^{33}$P-ATP 1 mCi/37 MBq from Perkin Elmer Life Sciences #NEG-602H
Enzyme:
Casein Kinase 1ε final concentration 0.58 mg/ml obtained from fermentation and purification processes well known to one skilled in the art. The above are stored as 100 μL aliquots at minus 80° C.
Compounds:
Supply compounds for testing as frozen 10 mM compound stock dissolved in 100% DMSO.

Assay Conditions:

Final total assay volume per well is equal to 50 μL that one prepares as follows:
- 5 μL of diluted compound stock (10, 1, 0.1, 0.01 or 0.001 μM),
- 5 μL of dephosphorylated casein final concentration 0.2 μg/μL,
- 20 μL of CK1ε final concentration 3 ng/μL, and
- 20 μL of γ-$^{33}$P-ATP final concentration 0.02 μCi/μL mixed with cold ATP (10 μM final).

Methodology:
1. Prepare 500 mL of fresh assay buffer: 50 mM Tris pH 7.5, 10 mM MgCl$_2$, 2 mM DTT and 1 mM EGTA
2. Obtain compounds to be evaluated as 10 μL of 10 mM stock dissolved in 100% DMSO. Use a Biomek 2000 liquid handling robot, make serial dilutions to yield 10, 1, 0.1, 0.01 and 0.001 μM final compound dilutions added as 5 μL additions to Falcon U bottom plates. Typically test 8 compounds per 96 well plate with column 1 and 12 serving as control wells. A routine screening assay will consist of 32 compounds, which equals 4 assay plates.
3. Assay plate maps are set up according to the following pattern CK1 ePlateMap.xls
7. At the end of 2 hours, stop the reaction by the addition of 65 μL of ice cold 2 mM cold ATP (made up in assay buffer) to the assay plates using a Beckman Multimek.
8. At the same time add 25 μL 100% ice cold TCA made up in distilled H$_2$0 to a matching number of Millipore MAPH filter plates.
9. Using a handheld 8-channel pipettor, transfer 100 μL of the reaction mixture from the Falcon U-Bottom Plate to the Millipore MAPH filter plates presoaked with TCA.
10. Mix the Millipore MAPH filter plates gently and allow to sit at room temperature for at least 30 minutes to precipitate the proteins.
11. After 30 minutes, place the filter plates on a Millipore vacuum manifold and filter at no more than 8 mm Hg as the MAPH filters tend to "air lock" at higher vacuum settings.
12. Wash the filter plates sequentially and filter with 2×150 μL 20% TCA, 2×150 μL 10% TCA and 2×150 μL 5% TCA (total of 6 washes per plate/900 μL per well).
13. Allow the plates to dry overnight at room temperature. The next day add 40 μL Packard Microscint-20 Scintillation Fluid per well using a Titertek Multidrop dispenser; seal the plates and count for 2 minutes/well in a Packard Topcount NXT Scintillation Counter (to provide CPM values/well).

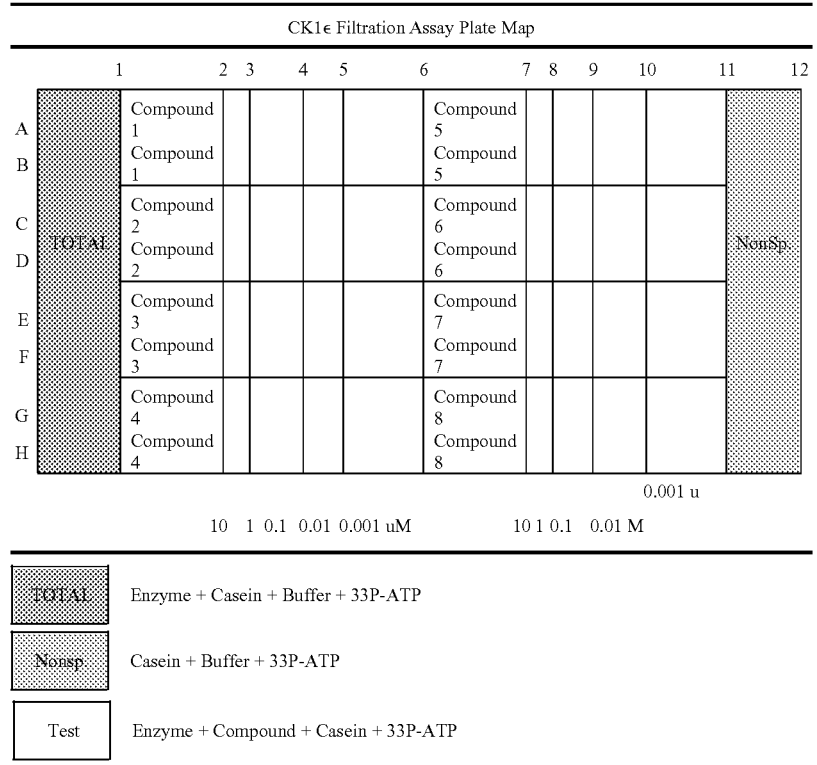

4. Add 5 μL of compound as indicated, then add 5 μL of dephosphorylated casein (dissolved in distilled H$_2$0)(0.2 μg/μL) and 20 μL CK1ε (3 ng/μL) to the appropriate wells.
5. Finally add 20 μL γ-$^{33}$P-ATP (0.02 μCi/μL)/10 μM cold ATP (equals approximately 2×10$^6$ CPM per well).
6. Vortes the Falcon U-Bottom assay plate containing the above 50 μL reaction volume and then incubate at room temperature for 2 hours.

Calculation:
1. Import Counts Per Minute (CPM) data into a proprietary data calculation and archiving database (Activity Base by IDBS version 5.0).
2. Column 1 for each plate reflects total phosphorylation activity of the enzyme in the absence of any inhibiting compound and thus represents 100%. Column 12 reflects any nonspecific phosphorylation/retained radioactivity activity in the absence of inhibiting compound and enzyme. Typically one observes approximately 1% of Total CPMs that are "nonspecific".
3. By determining the "total" and "nonspecific" CPMs for each plate, one is able to determine the % inhibition of the enzyme's ability to phosphorylate the substrate for each concentration of test compound. Use this % inhibition data to calculate an $IC_{50}$ value (concentration at which a compound is able to inhibit the enzyme activity by 50%) for a compound using a non-linear curve fit program contained with the Activitybase calculation protocol (DG0027-CK1-D-BL).
4. Kinetic studies have determined the $K_m$ value for ATP to be 21 µM in this assay system.

Casein Kinase 1δ Streptavidin Affinity Membrane Plate Assay for CK1δ Inhibitors

Purpose: To evaluate test compounds for CK1δ activity in Streptavidin Affinity Membrane (SAM) Biotin Capture Plate (Promega V7542)
Supplies and Reagents
HEPES Sigma # H3375 MW=238.3; β-Glycerol phosphate Sigma # G-9891 MW=216.0; EDTA 0.5M, pH 8.0 Gibco-BRL; Sodium orthovanadate ACROS # 205330500 MW=183.9; DTT (DL-dithiothreitol) Sigma # D-5545 MW=154.2; Magnesium Chloride ACROS # 41341-5000 MW=203.3; ATP Sigma #A-7699 MW=551.1; $\gamma^{33}P$ ATP NEN # NEG602H; Casein Kinase 1δ Sigma #C4455; Casein Kinase 1 substrate New England Peptide Biotin-RRKDLH-DDEEDEAMSITA MW=2470
Prepare Kinase Buffer (KB, 100 mL) as follows:

| | |
|---|---|
| 50 mM HEPES, pH 8.0 | 5 mL of 1M stock |
| 10 mM MgCl | 1 mL of 1M stock |
| 10 mM β-glycerophosphate | 1 mL of 1M stock |
| 2.5 mM EDTA | 500 µL of 500 mM stock |
| 1 mM sodium orthovanadate | 100 µL of 1M stock |
| 1 mM DTT | 100 µL of 1M stock |
| water | 92.3 mL |

Prepare ATP Master Mix as follows:
Prepare 1 mL of a 1 M ATP solution in water (1 M ATP stock).
To 12 mL KB:
  Add 12 µL of 1 M ATP solution, then
  Add 12 µL of $^{33}P$ ATP (10 µCi/ul), NEG602H, Perkin Elmer
Prepare the reaction plate and conduct the assay as follows:
1. Add 10 µL of KB per well with or without the test compound inhibitor to reaction plate wells
2. Add 60 µL of KB per well
3. Add 10 µL of 500 µM Peptide Substrate per well
4. Bring plate up to 37° C.
5. Add 10 µL of 1:10 dilution of CK1δ per well=0.42 µg or 0.68 units
6. Initiate the reaction with 10 µL of ATP Master Mix per well
7. Place the reaction plate in 37° C. incubator for 10 min.
8. Stop the reaction with 10 µL of 1 M ATP. Transfer 20 µL to the SAM Plate and let stand 10 min at room temperature.
9. Wash three times with 100 µL of 2M NaCl solution, then three times with 100 µL of 2M NaCl and 1% $H_3PO_4$ solutions and then three times with 100 µL of water on a vacuum manifold.
10. Dry the filter plate under a lamp for 30 min.
11. Seal bottom of plate and add 20 µL of MicroScint 20
12. Read in TOPCOUNT Cellular Circadian Assay Experimental Procedures Cell culture: Split Mper1-luc Rat-1 fibroblasts (P2C4) cultures every 3-4 days (~10-20% confluence) onto 150 $cm^2$ vented polystyrene tissue culture flasks (Falcon # 35-5001) and maintain in growth media [EMEM (Cellgro #10-010-CV); 10% fetal bovine serum (FBS; Gibco #16000-044); and 50 I.U./mL penicillin-streptomycin (Cellgro #30-001-C1)] at 37° C. and 5% $CO_2$. Data is presented in Table 3.
Stable transfection: Co-transfect Rat-1 fibroblast cultures at 30-50% confluence with vectors containing the Zeocin resistance selectable marker for stable transfection and an mPer-1 promoter-driven luciferase reporter gene. After 24-48 hours, split the cultures onto 96 well plates and maintain in growth media supplemented with 50-100 µg/mL Zeocin (Invitrogen #45-0430) for 10-14 days. Assess Zeocin-resistant stable transfectants for reporter expression by supplementing growth media with 100 µM luciferin (Promega #E1603) and assaying luciferase activity on a TopCount scintillation counter (Packard Model #C384V00). Synchronize Rat-1 clones expressing both Zeocin-resistance and mPer1-driven luciferase activity by 50% horse serum [HS (Gibco #16050-122)] serum shock and assess for circadian reporter activity. Select Mper1-luc Rat-1 fibroblasts clone P2C4 for compound testing.
Synchronization protocol: Plate Mper1-luc Rat-1 fibroblasts (P2C4) (40-50% confluence) onto opaque 96-well tissue culture plates (PerkinElmer #6005680) and maintain in growth media supplemented with 100 µg/mL Zeocin (Invitrogen #45-0430) until cultures reach 100% confluence (48-72 h). Synchronize cultures with 100 µL synchronization media [EMEM (Cellgro #10-010-CV); 100 I.U./mL penicillin-streptomycin (Cellgro #30-001-C1); 50% HS (Gibco #16050-122)] for 2 hours at 37° C. and 5% CO2. After synchronization, rinse cultures with 100 µL EMEM (Cellgro #10-010-CV) for 10 minutes at room temperature. After rinse, replace media with 300 µL CO2-independent media [CO2I (Gibco #18045-088); 2 mM L-glutamine (Cellgro #25-005-C1); 100 I.U./mL penicillin-streptomycin (Cellgro #30-001-C1); 100 µM luciferin (Promega #E1603)]. Add compounds to be tested for circadian effects to $CO_2$-independent media in 0.3% DMSO (final concentration). Seal cultures immediately with TopSeal-A film (Packard #6005185) and transfer for luciferase activity measurement.
Automated Circadian Reporter Measurement: After synchronization, maintain assay plates at 37° C. in a tissue culture incubator (Form a Scientific Model #3914). Estimate in vivo luciferase activity by measuring relative light output on a TopCount scintillation counter (Packard Model #C384V00). Transfer plates from incubator to reader using an ORCA robotic arm (Beckman Instruments) and SAMI-NT automated scheduling software (Version 3.3; SAGIAN/Beckman Instruments).
Data Analysis: Use Microsoft Excel and XLfit (Version 2.0.9; IDBS) to import, manipulate and graph data. Perform period analysis either by determining the interval between relative light output minima over several days or by Fourier Transform. Both methods produce nearly identical period estimation over a range of circadian periods. Report potency as $EC_{\Delta t+1h}$, which is the effective micromolar concentration that induces a 1 hour lengthening of period. Analyze the data by fitting a hyperbolic curve to the data expressed as period change (y-axis) versus the concentration of test compound (x-axis) in XLfit and interpolate the $EC_{\Delta\tau+1h}$ from this curve.

Rat Circadian Cycle Assay

This assay provides a means for assessing the effect of a test compound on circadian cycle in vivo. Use male Wistar rats (Charles River) with a starting body mass of 200-250 g. House each animal individually prior to testing in a controlled environment and maintain a thermoneutral ambient temperature of 24-28° C. under a 12/12 hour (h) light/dark cycle (lights on at 06:00 h), and give standard laboratory chow and water ad libitum. Implant each rat with an intra-abdominal biotelimetry transmitter (Minnimitter-VMFH, series 4000, Sunriver, Oreg.) to monitor core body temperature and general activity. Implant each transmitter as per the manufacturer's recommendations under ketamine/xylazine (78/13 mg kg$^{-1}$, ip) general anesthesia and allow the animals to recover for 7-10 days. After the recovery period, to establish each animal's internal circadian cycle, place the animals in a constant dark cycle (0/24 h light/dark cycle) and allow the animals to go into free run for 7-10 days prior to test compound administration. During the dosing regimen, animals receive either vehicle or compound (ip, sc, or po) at specific CTs (Circadian Times) over a 48 hour period. Monitor the animals for 5 to 7 days in a constant dark cycle (0/24 h light/dark cycle) after completion of the dosing regimen. For each experiment, sample abdominal temperature and general activity data at 5-minute intervals. For analysis, use the Vital-View and Actiview software supplied by Minimitter. Plot observed abdominal temperatures obtained for each rat on the first day on a horizontal line. Align the line of observed abdominal temperatures below an abscissa line with circadian time (x-axis). Plot observed abdominal temperatures for each successive day as individual lines in a similar manner to provide the ordinate (y-axis, in days). Connect the initial rise of core body temperature that occurs each day with a straight line, which allows the use of multiple days to estimate the circadian phase on any given day for each individual rat. Determine the effect of treatment on phase by using the straight line multi-day estimation of phase before and after dosing. Treatment with an active compound will cause a greater displacement between the straight line connecting the daily initial rise of core body temperature before compound treatment and the straight line connecting the initial rise of core body temperature after compound treatment versus the vehicle control before and after treatment lines. Calculate the difference between those phases projected onto the day prior to dosing for the treated animals. Use ANOVA, together with Students t test, to compare mean body temperature circadian shifts in minutes between groups.

TABLE 3

Biological Data

| Cmpd No. | Casein Kinase Iε $^{33}$P-ATP Filter Plate Assay $K_i$ (μM) (* denotes average of 2 or more determinations) | Cell Assay $EC_{\Delta\tau+1h}$ (μM) |
|---|---|---|
| Ia | 0.07 | 0.44 |
| Ib | | |
| Ic | 0.14* | |
| Id | 0.14 | 5.67 |
| Ie | 0.34 | 3.34 |
| If | 0.71 | |
| Ig | 4.45 | |

TABLE 3-continued

Biological Data

| Cmpd No. | Casein Kinase Iε $^{33}$P-ATP Filter Plate Assay $K_i$ (μM) (* denotes average of 2 or more determinations) | Cell Assay $EC_{\Delta\tau+1h}$ (μM) |
|---|---|---|
| Ih | 1.74 | |
| Ii | 0.24 | |
| Ij | 0.20* | |
| Ik | 0.093 | |
| Il | 0.88 | |
| Im | 0.064 | 4.55 |
| In | 0.11 | 5.11 |
| Io | ≈10 | |
| Ip | 0.074 | 1.87 |
| Iq | 0.31 | >3 |
| Ir | 0.13 | >10 |
| Is | 0.12* | 7.85 |
| It | 0.45 | 2.70 |
| Iu | 0.60 | |
| Iv | 0.36* | |
| Iw | 0.065 | |
| Ix | 0.13 | |
| Iy | 0.34 | |
| Iz | 0.32 | |
| Iaa | >10 | |
| Iab | >10 | |
| Iac | ≈10 | |
| Iad | 0.09 | |
| Iae | 0.58 | |
| Iaf | 0.39 | |
| Iag | 2.23 | |
| Iah | 4.28* | |
| Iai | 6.85 | 6.91 |
| Iaj | 0.54 | |
| IIa | 0.097 | |
| IIb | 2.33 | |
| IIc | 0.72 | |
| IId | 0.47 | |
| IIe | 0.73 | |
| IIf | 0.81 | |
| IIg | 0.52 | |
| IIh | 0.74 | |
| IIi | 0.39 | |
| IIj | 1.39 | |
| IIk | 1.19 | |
| IIl | 1.77 | |
| IIm | 4.88 | |
| IIn | 4.99 | |
| IIo | 0.17 | |
| IIp | 0.12 | |
| IIq | 0.15 | |
| IIr | 0.27 | |
| IIs | 0.1 | |
| IIt | 1.28 | |
| IIu | | |
| IIv | 1.01 | |
| IIw | 0.29 | |
| IIx | 1.19 | |
| IIy | 0.38 | |
| IIz | 0.57 | |
| IIaa | 0.46 | |
| IIab | 4.04 | |
| IIac | 0.24 | |
| IIad | 0.11* | |
| IIae | 0.78 | |
| IIaf | 4.83 | |
| IIag | 6.92 | |
| IIah | 3.50 | |
| IIai | 0.60 | |
| IIaj | 2.10 | |
| IIak | 0.64 | |
| IIal | 1.21 | |
| IIam | 2.42 | |
| IIan | >10.0 | |
| IIao | >10.0 | |
| IIap | >10.0 | |
| IIaq | 0.14 | |

TABLE 3-continued

Biological Data

| Cmpd No. | Casein Kinase Iε $^{33}$P-ATP Filter Plate Assay $K_i$ (μM) (* denotes average of 2 or more determinations) | Cell Assay $EC_{\Delta\tau+1h}$ (μM) |
|---|---|---|
| IIar | 2.54 | |
| IIas | 6.25 | |
| IIat | >10.0 | |
| IIau | 0.70 | |

What is claimed is:

1. A method for the treatment of a patient suffering from a disease or disorder ameliorated by the inhibition of casein kinase Iε activity wherein said disease or disorder is selected from the group consisting of mood disorders and sleep disorders, comprising the administration of a compound of formula I or formula II, an enantiomer, or a pharmaceutically acceptable salt thereof, optionally in combination with one or more pharmaceutically acceptable carriers, diluents or excipients,

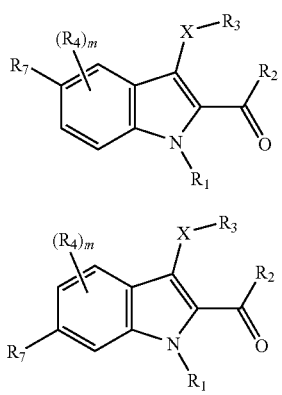

wherein
X is S or $S(O)_n$;
$R_1$ is H or $C_1$-$C_6$alkyl;
$R_2$ is $NR_5R_6$;
$R_3$ is aryl or heterocycle;
$R_4$ is $C_1$-$C_6$alkyl or halogen;
$R_5$ is H or $C_1$-$C_6$alkyl;
$R_6$ is H or $C_1$-$C_6$alkyl;
$R_7$ is $CH_2NR_8R_9$ wherein
  $R_8$ is H, $C_1$-$C_{10}$alkyl, $C_3$-$C_8$cycloalkyl, aryl, aryl($C_1$-$C_6$alkyl), aryl($C_2$-$C_6$alkenyl), diaryl($C_2$-$C_6$alkenyl), heterocycle, heterocycle($C_1$-$C_6$alkyl), heterocycle($C_2$-$C_6$alkenyl), hydroxy($C_1$-$C_6$alkyl), dihydroxy($C_2$-$C_6$alkyl), acyl, $C_1$-$C_6$alkoxycarbonyl, aryl($C_1$-$C_6$alkoxy)carbonyl, carbamoyl($C_1$-$C_6$ alkyl), or P;
  $R_9$ is H, $C_1$-$C_{10}$alkyl, heterocycle($C_1$-$C_6$alkyl) or heterocycle($C_2$-$C_6$alkenyl); or
  $R_8$ and $R_9$ together with the nitrogen to which they are attached form a heterocycle;
  and wherein P is Gly, or L- or D-Ala, Val, Leu, Ile, Ser, Cys, Thr, Met, Pro, Phe, Tyr, Trp, His, Lys, Arg, Asp, Gly, Asn or Gln;
m is 0, 1 or 2; and
n is 1 or 2.

2. The method of claim 1 wherein said compound is selected from the group consisting of formula I and formula II wherein X is S.

3. The method of claim 2 wherein said compound is selected from the group consisting of formula I and formula II wherein $R_2$ is $NH_2$.

4. The method of claim 3 wherein said compound is selected from the group consisting of formula I and formula II wherein m is 0 and $R_7$ is $CH_2NR_8R_9$.

5. The method of claim 4 wherein said compound is selected from the group consisting of formula I and formula II wherein $R_1$ is $C_1$-$C_6$alkyl.

6. The method of claim 5 wherein said compound is 1-methyl-5-methylaminomethyl-3-phenylsulfanyl-1H-indole-2-carboxylic acid amide.

7. The method of claim 3 wherein said compound is selected from the group consisting of formula I and formula II wherein $R_1$ is H.

8. The method as recited in claim 7 wherein $R_8$ is H, $C_1$-$C_{10}$alkyl, $C_3$-$C_8$cycloalkyl, hydroxy($C_1$-$C_6$alkyl), dihydroxy($C_2$-$C_6$alkyl) or $C_1$-$C_6$alkoxycarbonyl and $R_9$ is H.

9. The method as recited in claim 8 wherein said compound is:

5-aminomethyl-3-phenylsulfanyl-1H-indole-2-carboxylic acid amide.

10. The method of claim 9 wherein said inhibition of casein kinase Iε activity results in a lengthening of circadian rhythm period.

11. The method of claim 1 wherein the disorder is mood disorder.

12. The method according to claim 11 wherein the mood disorder is selected from the group consisting of a depressive disorder and a bipolar disorder.

13. The method according to claim 12 wherein the depressive disorder is major depressive disorder.

14. The method of claim 12 wherein the mood disorder is a bipolar disorder.

15. The method of claim 14 wherein the bipolar disorder is selected from the group consisting of bipolar I disorder and bipolar II disorder.

16. The method of claim 1 wherein the disorder is a sleep disorder.

17. The method of claim 16 wherein the sleep disorder is a circadian rhythm sleep disorder.

18. The method of claim 17 wherein the circadian rhythm sleep disorder is selected from the group consisting of shift work sleep disorder, jet lag syndrome, advanced sleep phase syndrome and delayed sleep phase syndrome.

* * * * *

UNITED STATES PATENT AND TRADEMARK OFFICE
CERTIFICATE OF CORRECTION

PATENT NO. : 7,923,466 B2  Page 1 of 1
APPLICATION NO. : 12/269216
DATED : April 12, 2011
INVENTOR(S) : William Arthur Metz, Jr. et al.

It is certified that error appears in the above-identified patent and that said Letters Patent is hereby corrected as shown below:

In column 32, line 34, delete "crude is" and insert -- crude --, therefor.

In column 37, line 57, delete "la" and insert -- 11a --, therefor.

In column 39, line 16, delete "Methyaminomethyl" and insert -- Methylaminomethyl --, therefor.

In column 53, line 37, delete " $4\text{-}(CH_2)_3N\text{---}C_6H_4CH_2NH$ " and insert -- $4\text{-}(CH_3)_2N\text{-}C_6H_4CH_2NH$ --, therefor.

In column 64, line 60, in claim 6, delete "5- methylaminomethyl" and insert -- 5-methylaminomethyl --, therefor.

Signed and Sealed this
Thirteenth Day of September, 2011

David J. Kappos
*Director of the United States Patent and Trademark Office*